United States Patent
Gardberg et al.

(10) Patent No.: US 12,172,990 B2
(45) Date of Patent: Dec. 24, 2024

(54) MODULATORS OF TREX1

(71) Applicant: Constellation Pharmaceuticals, Inc., Boston, MA (US)

(72) Inventors: Anna Gardberg, Boston, MA (US); Victor S. Gehling, Somerville, MA (US); Avinash Khanna, Cambridge, MA (US); Julian R. Levell, Arlington, MA (US); Jonathan E. Wilson, Arlington, MA (US); Kennedy Taveras, Lynn, MA (US)

(73) Assignee: Constellation Pharmaceuticals, Inc., Boston, MA (US)

( * ) Notice: Subject to any disclaimer, the term of this patent is extended or adjusted under 35 U.S.C. 154(b) by 821 days.

(21) Appl. No.: 17/311,526

(22) PCT Filed: Dec. 6, 2019

(86) PCT No.: PCT/US2019/064825
§ 371 (c)(1),
(2) Date: Jun. 7, 2021

(87) PCT Pub. No.: WO2020/118133
PCT Pub. Date: Jun. 11, 2020

(65) Prior Publication Data
US 2022/0017502 A1  Jan. 20, 2022

Related U.S. Application Data

(60) Provisional application No. 62/776,031, filed on Dec. 6, 2018.

(51) Int. Cl.
C07D 413/12 (2006.01)
A61P 35/00 (2006.01)
C07D 413/14 (2006.01)

(52) U.S. Cl.
CPC ............ *C07D 413/12* (2013.01); *A61P 35/00* (2018.01); *C07D 413/14* (2013.01)

(58) Field of Classification Search
CPC .......................... C07D 413/12; C07D 413/14
See application file for complete search history.

(56) References Cited

U.S. PATENT DOCUMENTS

| | | |
|---|---|---|
| 2007/0037974 A1 | 2/2007 | Brotherton-Pleiss et al. |
| 2022/0289728 A1 | 9/2022 | Khanna et al. |
| 2022/0313701 A1 | 10/2022 | Khanna et al. |

FOREIGN PATENT DOCUMENTS

| | | |
|---|---|---|
| CN | 101355946 A | 1/2009 |
| CN | 102046608 A | 5/2011 |
| CN | 102753184 A | 10/2012 |
| EP | 3061754 A1 | 8/2016 |
| WO | 2003/035077 A1 | 5/2003 |
| WO | 2005/014573 A1 | 2/2005 |
| WO | 2007/056124 A2 | 5/2007 |
| WO | 2008/033564 A1 | 3/2008 |
| WO | 2008/113006 A1 | 9/2008 |
| WO | 2009/106561 A1 | 9/2009 |
| WO | 2010/017355 A2 | 2/2010 |
| WO | 2011/107494 A1 | 9/2011 |
| WO | 2012/016133 A2 | 2/2012 |
| WO | 2012/125887 A1 | 9/2012 |
| WO | 2012/151567 A1 | 11/2012 |
| WO | 2013/047144 A1 | 4/2013 |
| WO | 2014/023691 A1 | 2/2014 |
| WO | 2015/095128 A1 | 6/2015 |
| WO | 2016/183741 A1 | 11/2016 |
| WO | 2017/192961 A1 | 11/2017 |
| WO | 2018/237084 A1 | 12/2018 |
| WO | 2019/245910 A1 | 12/2019 |
| WO | 2020/118133 A1 | 6/2020 |
| WO | 2021/016317 A1 | 1/2021 |

OTHER PUBLICATIONS

Lala, et al. Cancer and Metastasis Reviews (1998), 17(1), 91-106.*
Golub, et al. Science 286, 531 (1999).*
Cancer [online], [retrieved on Aug. 11,2023]. Retrieved from the internet, URL https://medlineplus.gov/cancer.html#>.*
Cid et al, Discovery of 1-butyl-3-chloro-4-(4-phenyl-1-piperidinyl)-(1H)-pyridone (JNJ-40411813): a novel positive allosteric modulator of the metabotropic glutamate 2 receptor. J Med Chem. Aug. 14, 2014;57(15):6495-512.
Vanpouille-Box et al., DNA exonuclease Trex1 regulates radiotherapy-induced tumour immunogenicity. Nat Commun. Jun. 9, 2017;8:15618, 15 pages.
Vanpouille-Box et al., Synthesis and in vitro characterization of cinnoline and benzimidazole analogues as phosphodiesterase 10A inhibitors. Bioorg Med Chem Lett. Feb. 15, 2015;25(4):919-24, 15 pages.

(Continued)

*Primary Examiner* — Shawquia Jackson
(74) *Attorney, Agent, or Firm* — McCarter & English, LLP; Michael J. DeGrazia

(57) ABSTRACT

Provided are compounds of Formula (I): and pharmaceutically acceptable salts and compositions thereof, which are useful for treating a variety of conditions associated with TREX1.

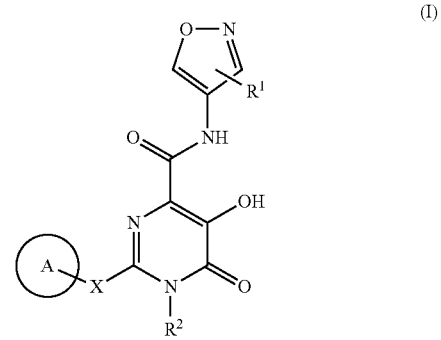

19 Claims, 4 Drawing Sheets

(56) References Cited

OTHER PUBLICATIONS

Yang et al., Synthesis and in vitro characterization of cinnoline and benzimidazole analogues as phosphodiesterase 10A inhibitors. Bioorg Med Chem Lett. Feb. 15, 2015;25(4):919-24.
Copending U.S. Appl. No. 17/607,940, filed Nov. 1, 2021.
Copending U.S. Appl. No. 17/628,946, filed Jan. 21, 2022.
U.S. Appl. No. 17/607,940, filed Nov. 1, 2021, 2022/0313701, Published.
U.S. Appl. No. 17/628,946, filed Jan. 21, 2022, 2022/0289728, Published.
U.S. Appl. No. 17/922,388, filed Oct. 31, 2022, Pending.
U.S. Appl. No. 17/926,849, filed Nov. 21, 2022, Pending.
Brucet et al., Structural and biochemical studies of TREX1 inhibition by metals. Identification of a new active histidine conserved in DEDDh exonucleases. Protein Science 17(12): 2059-2069, 2008.

\* cited by examiner

MODULATORS OF TREX1

RELATED APPLICATIONS

This application is a 35 U.S.C. § 371 national stage filing of International Application No. PCT/US2019/064825, filed on Dec. 6, 2019, which claims priority to U.S. Provisional Application No. 62/776,301, filed Dec. 6, 2018, the entire contents of each of which are incorporated herein by reference.

BACKGROUND

A potential immune therapy is needed for cancers related to the innate immune system recognition of non-self, and to detect and protect against potential danger. Cancer cells differ antigenically from their normal counterparts and emit danger signals to alert the immune system similar to viral infection. These signals, which include damage-associated molecular patterns (DAMPs) and pathogen-associated molecular patterns (PAMPs), further activate the innate immune system resulting in the protection of the host from a variety of threats (*Front. Cell Infect. Microbiol.* 2012, 2, 168).

Ectopically expressed single stranded DNA (ssDNA) and double stranded DNA (dsDNA) are known PAMPs and/or DAMPs, which are being recognized by the cyclic GMP-AMP synthase (cGAS), a nucleic acid sensor (*Nature* 2011, 478, 515-518). Upon sensing of cytosolic DNA, cGAS catalyzes the generation of the cyclic dinucleotide 2',3'-cGAMP, a potent second messenger and activator of the ER transmembrane adapter protein stimulator of interferon genes (STING) (*Cell Rep.* 2013, 3, 1355-1361). STING activation triggers phosphorylation of IRF3 via TBK1 which in turn leads to type I interferon production and activation of interferon stimulated genes (ISGs); a pre-requisite to the activation of innate immunity and initiation of adaptive immunity. Production of type I interferons thus constitutes a key bridge between the innate and adaptive immunity (*Science* 2013, 341, 903-906).

Excess type I IFN can be harmful to the host and induce autoimmunity, therefore, negative feedback mechanisms exist that keep type I IFN-mediated immune activation in check. Three prime repair exonuclease I (TREX1) is a 3'-5' DNA exonuclease responsible for the removal of ectopically expressed ssDNA and dsDNA and is therefore a key repressor of the cGAS/STING pathway (*PNAS* 2015, 112, 5117-5122).

Type I interferons and downstream pro-inflammatory cytokine responses are critical to the development of immune responses and their effectiveness. Type I interferons enhance both the ability of dendritic cells and macrophages to take up, process, present, and cross-present antigens to T cells, and their potency to stimulate T cells by eliciting the up-regulation of the co-stimulatory molecules such as CD40, CD80 and CD86 (*J. Exp. Med.* 2011, 208, 2005-2016). Type I interferons also bind their own receptors and activate interferon responsive genes that contribute to activation of cells involved in adaptive immunity (*EMBO Rep.* 2015, 16, 202-212).

From a therapeutic perspective, type I interferons and compounds that can induce type I interferon production have potential for use in the treatment of human cancers (*Nat. Rev Immunol.* 2015, 15, 405-414). Interferons can inhibit human tumor cell proliferation directly. In addition, type I interferons can enhance anti-tumor immunity by triggering the activation of cells from both the innate and adaptive immune system. Importantly, the anti-tumor activity of PD-1 blockade requires pre-existing intratumoral T cells. By turning cold tumors into hot and thereby eliciting a spontaneous anti-tumor immunity, type I IFN-inducing therapies have the potential to expand the pool of patients responding to anti-PD-1 therapy as well as enhance the effectiveness of anti-PD1 therapy.

Therapies that are currently in development that induce a potent type I interferon response require focal or intratumoral administration to achieve an acceptable therapeutic index. Thus, there remains a need for new agents with systemic delivery and lower toxicity to expand the benefit of type I IFN-inducing therapies to patients without peripherally treatment accessible lesions. Human and mouse genetic studies suggest that TREX1 inhibition might be amenable to a systemic delivery route and therefore TREX1 inhibitory compounds could play an important role in the anti-tumor therapy landscape. TREX1 is a key determinant for the limited immunogenicity of cancer cells responding to radiation treatment [*Trends in Cell Biol.*, 2017, 27 (8), 543-4; *Nature Commun.*, 2017, 8, 15618]. TREX1 is induced by genotoxic stress and involved in protection of glioma and melanoma cells to anticancer drugs [*Biochim. Biophys. Acta*, 2013, 1833, 1832-43]. STACT-TREX1 therapy shows robust anti-tumor efficacy in multiple murine cancer models [Glickman et al, Poster P235, 33rd Annual Meeting of Society for Immunotherapy of Cancer, Washington DC, Nov. 7-11, 2018].

SUMMARY

Embodiments described herein generally relate to agents, compounds, compositions and methods for treating diseases responsive to TREX1 inhibitors. TREX1 inhibitors selective over TREX2 inhibitors have been successfully synthesized in this invention.

Provided herein are compounds having the Formula I:

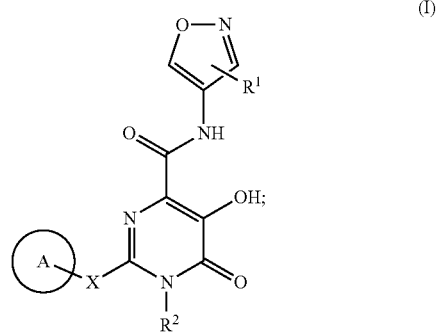

and pharmaceutically acceptable salts and compositions thereof, wherein A, $R^1$, $R^2$ and n are as described herein. The disclosed compounds and compositions modulate TREX1, and are useful in a variety of therapeutic applications such as, for example, in treating cancer.

DETAILED DESCRIPTION

1. General Description of Compounds

Figure 1:
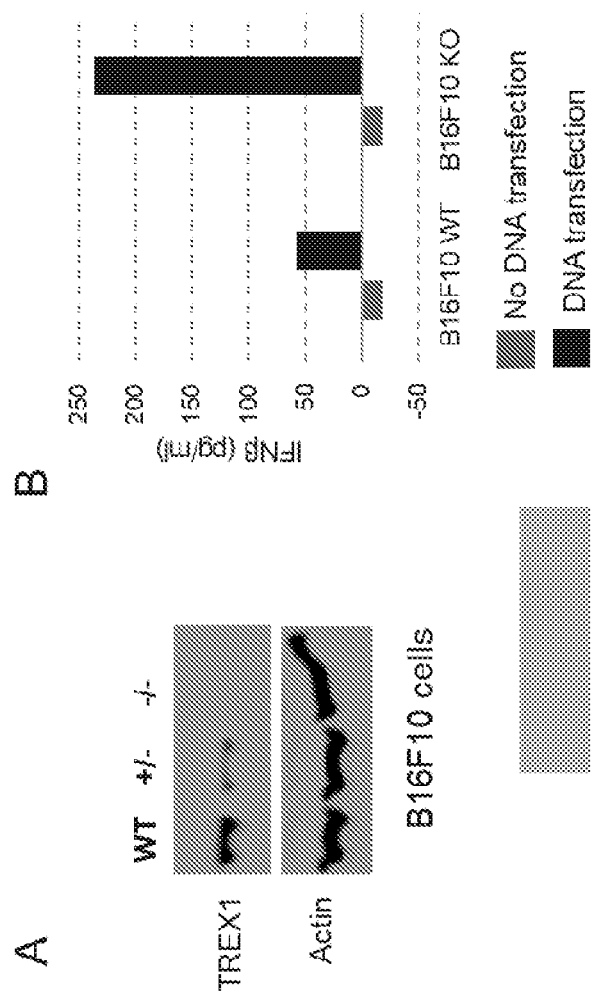
FIG. 1A illustrates the results from a knock down experiment of TREX1 in B16F10 tumor cells using CRISPR.
FIG. 1B illustrates TREX1 attenuated the activation of the cGAS/STING pathway in B16F10 tumor cells.

In a first embodiment, provided herein is a compound of Formula I:

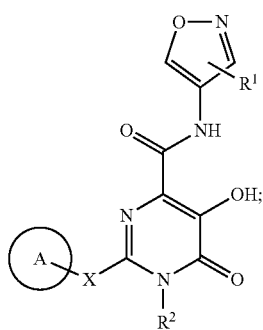

or a pharmaceutically acceptable salt thereof, wherein:
$R^1$ is hydrogen, $(C_1-C_4)$alkyl, halo$(C_1-C_4)$alkyl, 3- to 4-membered cycloalkyl, —$OR^f$, —$SR^f$, or —$NR^eR^f$;
$R^2$ is hydrogen, $(C_1-C_4)$alkyl, halo$(C_1-C_4)$alkyl, or 3- to 4-membered cycloalkyl;
X is a bond, $NR^3$, O, S, or $(C_1-C_4)$alkylene, wherein said $(C_1-C_4)$alkylene is optionally substituted with 1 to 2 groups selected from $R^4$;
$R^3$ is hydrogen, $(C_1-C_4)$alkyl, —$C(O)R^d$, or —$C(S)R^d$;
$R^4$ is halo, $(C_1-C_4)$alkyl, phenyl, —NHC(O)$OR^a$, —NHC(S)$OR^a$, —$C(O)R^b$, —NHC(O)$NHR^g$, —NHC(S)$NHR^g$, —NHS(O)$_2NHR^g$, —$C(S)R^b$, $S(O)_2R^c$, $S(O)R^c$, —$C(O)OR^d$, —$C(S)OR^d$, —$C(O)NHR^e$, —$C(S)NHR^e$, —NHC(O)$R^d$, —NHC(S)$R^d$, —$OR^e$, —$SR^e$, —$O(C_1-C_4)$alkyl$OR^e$, or —$NR^eR^f$, wherein said phenyl for $R^4$ is optionally substituted with 1 or 2 groups selected from halo, $(C_1-C_4)$alkyl, halo$(C_1-C_4)$alkyl, $(C_1-C_4)$alkoxy, and halo$(C_1-C_4)$alkoxy;
Ring A is phenyl, 5- to 6-membered heteroaryl, 4- to 7-membered heterocyclyl, or 3- to 7-membered cycloalkyl, each of which are optionally and independently substituted with 1 or 2 groups selected from $R^5$;
$R^5$ is $(C_1-C_4)$alkyl, halo$(C_1-C_4)$alkyl, halo$(C_1-C_4)$alkoxy, halo, phenyl, —NHC(O)$OR^a$, —NHC(S)$OR^a$, —$C(O)R^b$, —NHC(O)$NHR^g$, —NHC(S)$NHR^g$, —NHS(O)$_2NHR^g$, —$C(S)R^b$, $S(O)_2R^c$, $S(O)R^c$, —$C(O)OR^d$, —$C(S)OR^d$, —$C(O)NR^eR^f$, —$C(S)NHR^e$, —NHC(O)$R^d$, —NHC(S)$R^d$, —$OR^e$, —$SR^e$, —$O(C_1-C_4)$alkyl$OR^e$, —$NR^eR^f$, 4- to 6-membered heteroaryl, or 4- to 7-membered heterocyclyl, wherein said phenyl for $R^5$ is optionally substituted with 1 or 2 groups selected from $R^g$, said $(C_1-C_4)$alkyl for $R^5$ is optionally substituted with 1 or 2 groups selected from $OR^h$, —$NR^jR^k$, phenyl, and 5- to 6-membered heteroaryl, said 4- to 7-membered heterocyclyl and 4- to 6-membered heteroaryl are each optionally and independently substituted with 1 or 2 groups selected from $R^m$, and wherein said phenyl and 5- to 6-membered heteroaryl of the optional substituents listed for $(C_1-C_4)$alkyl in $R^5$ are each optionally and independently substituted with 1 or 2 groups selected from $R^g$;
$R^g$, $R^h$, $R^j$, $R^k$, and $R^m$ are each independently hydrogen, halo, $(C_1-C_4)$alkyl, halo$(C_1-C_4)$alkyl, $(C_1-C_4)$alkoxy, halo$(C_1-C_4)$alkoxy, phenyl, —$(C_1-C_4)$alkylphenyl, 3- to 4-membered cycloalkyl, 4- to 6-membered heteroaryl, or 4- to 7-membered heterocyclyl, and wherein said 4- to 7-membered heterocyclyl for $R^g$, $R^h$, $R^j$ and $R^k$ is further optionally substituted with =O.
$R^a$, $R^b$, $R^c$, $R^d$, $R^e$ and $R^f$ are each independently hydrogen, halo, $(C_1-C_4)$alkyl, halo$(C_1-C_4)$alkyl, $(C_1-C_4)$alkoxy, halo$(C_1-C_4)$alkoxy, phenyl, 3- to 4-membered cycloalkyl, 4- to 6-membered heteroaryl, or 4- to 7-membered heterocyclyl, wherein i) said $(C_1-C_4)$alkyl for $R^a$, $R^b$, $R^c$, $R^d$, $R^e$ and $R^f$ is optionally substituted with 1 or 2 groups selected from phenyl, —$OR^h$, —$NR^jR^k$; ii) said phenyl, 4- to 6-membered heteroaryl, and 4- to 7-membered heterocyclyl for $R^a$, $R^b$, $R^c$, $R^d$, $R^e$, and $R^f$ are each optionally and independently substituted with 1 or 2 groups selected from $R^g$, and iii) said 4- to 7-membered heterocyclyl for $R^a$, $R^b$, $R^c$, $R^d$, $R^e$, and $R^f$ is further optionally substituted with =O.

2. Definitions

When used in connection to describe a chemical group that may have multiple points of attachment, a hyphen (-) designates the point of attachment of that group to the variable to which it is defined. For example, —NHC(O)$OR^a$ and —NHC(S)$OR^a$ mean that the point of attachment for this group occurs on the nitrogen atom.

The terms "halo" and "halogen" refer to an atom selected from fluorine (fluoro, —F), chlorine (chloro, —Cl), bromine (bromo, —Br), and iodine (iodo, —I).

The term "alkyl" when used alone or as part of a larger moiety, such as "haloalkyl", and the like, means saturated straight-chain or branched monovalent hydrocarbon radical. Unless otherwise specified, an alkyl group typically has 1-4 carbon atoms, i.e., $(C_1-C_4)$alkyl.

The term "alkylene" refers to a divalent saturated hydrocarbon.

"Alkoxy" means an alkyl radical attached through an oxygen linking atom, represented by —O-alkyl. For example, "$(C_1-C_4)$alkoxy" includes methoxy, ethoxy, proproxy, and butoxy.

The term "haloalkyl" includes mono, poly, and perhaloalkyl groups where the halogens are independently selected from fluorine, chlorine, bromine, and iodine.

"Haloalkoxy" is a haloalkyl group which is attached to another moiety via an oxygen atom such as, e.g., but are not limited to —OCHCF$_2$ or —OCF$_3$.

The term "heteroaryl" used alone or as part of a larger moiety refers to a 5- to 6-membered aromatic radical containing 1-4 heteroatoms selected from N, O, and S. Heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, etc. It will be understood that when specified, optional substituents on a heteroaryl group may be present on any substitutable position.

The term "heterocyclyl" means a 4- to 7-membered saturated or partially unsaturated heterocyclic ring containing 1 to 4 heteroatoms independently selected from N, O, and S. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "cycloalkyl" refers to a cyclic hydrocarbon having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl or cycloaliphatic group may be present on any substitutable position and, include, e.g., the position at which the cycloalkyl or cycloaliphatic group is attached.

The term "TREX1" refers to Three prime repair exonuclease 1 or DNA repair exonuclease 1, which is an enzyme that in humans is encoded by the TREX1 gene. Mazur D J, Perrino F W (August 1999). "Identification and expression of the TREX1 and TREX2 cDNA sequences encoding mammalian 3'→5' exonucleases". J Biol Chem. 274 (28): 19655-60. doi:10.1074/jbc.274.28.19655. PMID 10391904; Hoss M, Robins P, Naven T J, Pappin D J, Sgouros J, Lindahl T (August 1999). "A human DNA editing enzyme homologous to the *Escherichia coli* DnaQ/MutD protein". EMBO J. 18 (13): 3868-75. doi:10.1093/emboj/18.13.3868. PMC 1171463. PMID 10393201. This gene encodes the major 3'->5' DNA exonuclease in human cells. The protein is a non-processive exonuclease that may serve a proofreading function for a human DNA polymerase. It is also a component of the SET complex, and acts to rapidly degrade 3' ends of nicked DNA during granzyme A-mediated cell death. Cells lacking functional TREX1 show chronic DNA damage checkpoint activation and extra-nuclear accumulation of an endogenous single-strand DNA substrate. It appears that TREX1 protein normally acts on a single-stranded DNA polynucleotide species generated from processing aberrant replication intermediates. This action of TREX1 attenuates DNA damage checkpoint signaling and prevents pathological immune activation. TREX1 metabolizes reverse-transcribed single-stranded DNA of endogenous retroelements as a function of cell-intrinsic antiviral surveillance, resulting in a potent type I IFN response. TREX1 helps HIV-1 to evade cytosolic sensing by degrading viral cDNA in the cytoplasm.

The term "TREX2" refers to Three prime repair exonuclease 2 is an enzyme that in humans is encoded by the TREX2 gene. This gene encodes a nuclear protein with 3' to 5' exonuclease activity. The encoded protein participates in double-stranded DNA break repair, and may interact with DNA polymerase delta. Enzymes with this activity are involved in DNA replication, repair, and recombination. TREX2 is a 3'-exonuclease which is predominantly expressed in keratinocytes and contributes to the epidermal response to UVB-induced DNA damage. TREX2 biochemical and structural properties are similar to TREX1, although they are not identical. The two proteins share a dimeric structure and can process ssDNA and dsDNA substrates in vitro with almost identical $k_{cat}$ values. However, several features related to enzyme kinetics, structural domains, and subcellular distribution distinguish TREX2 from TREX1. TREX2 present a 10-fold lower affinity for DNA substrates in vitro compared with TREX1. In contrast with TREX1, TREX2 lacks a COOH— terminal domain that can mediate protein-protein interactions. TREX2 is localized in both the cytoplasm and nucleus, whereas TREX1 is found in the endoplasmic reticulum, and is mobilized to the nucleus during granzyme A-mediated cell death or after DNA damage.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

The term "effective amount" or "therapeutically effective amount" refers to an amount of a compound described herein that will elicit a desired or beneficial biological or medical response of a subject e.g., a dosage of between 0.01-100 mg/kg body weight/day.

3. Compounds

In a second embodiment, provided herein is a compound of Formula II:

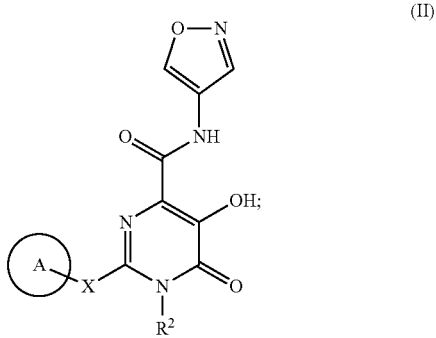

or a pharmaceutically acceptable salt thereof, wherein the variables are as described above in the first embodiment.

In a third embodiment, $R^2$ is $(C_1-C_4)$alkyl in the compounds of Formula I or II.

In a fourth embodiment, provided herein is a compound of Formula III:

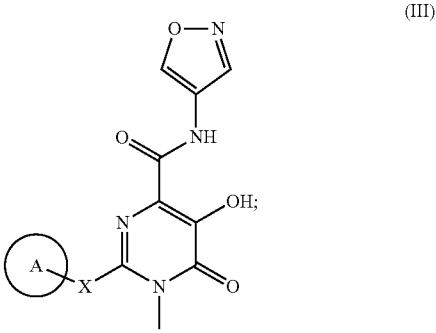

or a pharmaceutically acceptable salt thereof, wherein the variables are as described above in the first, second, or third embodiment.

In a fifth embodiment, ring A in the compounds of Formula I, II, or III is phenyl, pyridyl, pyrazolyl, cyclopropyl, cyclobutyl, azetidinyl, or piperidinyl, each of which being optionally and independently substituted with one or two $R^5$, wherein the remaining variables are as described above for the first, second, third or fourth embodiment. Alternatively, as part of a fifth embodiment, ring A in the compounds of Formula I, II, or III is triazolyl, pyrrolidinyl, diazepanyl, or piperazinyl, each of which being optionally and independently substituted with one or two $R^5$, wherein the remaining variables are as described above for the first, second, third or fourth embodiment.

In a sixth embodiment, $R^5$ in the compounds of Formula I, II, or III is $(C_1-C_4)$alkyl, halo$(C_1-C_4)$alkyl, halo$(C_1-C_4)$alkoxy, halo, phenyl, —NHC(O)OR$^a$, —C(O)R$^b$, S(O)$_2$R$^c$, S(O)R$^c$, —C(O)OR$^d$, —C(O)NR$^e$R$^f$, —NHC(O)R$^d$, —OR$^e$, —O(C$_1$-C$_4$)alkylOR$^e$, —NR$^e$R$^f$, 4- to 6-membered heteroaryl, or 4- to 7-membered heterocyclyl, wherein said phenyl for $R^5$ is optionally substituted with 1 or 2 groups selected from R$^g$, said (C$_1$-C$_4$)alkyl for $R^5$ is optionally substituted with 1 or 2 groups selected from —OR$^h$, —NR$^j$R$^k$, phenyl, and 5- to 6-membered heteroaryl, said 4- to 6-membered heteroaryl and 4- to 7-membered heterocyclyl are each optionally and independently substituted with 1 or 2 groups selected from R$^m$, and wherein said phenyl and 5- to 6-membered heteroaryl of the optional substituents listed for (C$_1$-C$_4$)alkyl in $R^5$ are each optionally and independently substituted with 1 or 2 groups selected from R$^g$; R$^a$ is (C$_1$-C$_4$)alkyl optionally substituted with phenyl; R$^b$ is (C$_1$-C$_4$)alkyl, phenyl, 5- to 6-membered heteroaryl or 4- to 7-membered heterocyclyl, wherein said (C$_1$-C$_4$)alkyl is optionally substituted with 1 or 2 groups selected from phenyl, —OR$^h$, and —NR$^j$R$^k$, wherein said phenyl, 5- to 6-membered heteroaryl, and 4- to 7-membered heterocyclyl are each optionally and independently substituted with 1 or 2 groups selected from R$^g$, and wherein said 4- to 7-membered heterocyclyl is further optionally substituted with =O; each R$^c$ is independently phenyl or (C$_1$-C$_4$)alkyl; each R$^d$ is hydrogen or (C$_1$-C$_4$)alkyl; each R$^e$ is independently hydrogen or (C$_1$-C$_4$)alkyl optionally substituted with OR$^h$; each R$^f$ is independently hydrogen, (C$_1$-C$_4$)alkyl, phenyl 3- to 4-membered cycloalkyl, 4- to 6-membered heteroaryl, or 5- to 6-membered heterocyclyl, wherein said phenyl, 3- to 4-membered cycloalkyl, 4- to 6-membered heteroaryl, and 5- to 6-membered heterocyclyl are each optionally and independently substituted with R$^g$; each R$^g$ is independently (C$_1$-C$_4$)alkyl, halo(C$_1$-C$_4$)alkyl, (C$_1$-C$_4$)alkoxy, halo(C$_1$-C$_4$)alkoxy, or halo; each R$^h$ is hydrogen, (C$_1$-C$_4$)alkyl, or —(C$_1$-C$_4$)alkylphenyl; each R$^j$ is independently hydrogen or (C$_1$-C$_4$)alkyl; each R$^k$ is independently hydrogen, (C$_1$-C$_4$) alkyl, or 3- to 4-membered cycloalkyl; and each R$^m$ is (C$_1$-C$_4$)alkyl, wherein the remaining variables are as described above for the first, second, third, fourth or fifth embodiment.

In a seventh embodiment, $R^5$ in the compounds of Formula I, II, or III is (C$_1$-C$_4$)alkyl, halo(C$_1$-C$_4$)alkyl, halo, phenyl, —NHC(O)OR$^a$, —C(O)R$^b$, S(O)$_2$R$^c$, —C(O)OR$^d$, —C(O)NR$^e$R$^f$, —NHC(O)R$^d$, —O(C$_1$-C$_4$)alkylOR$^e$, —NR$^e$R$^f$, 4- to 6-membered heteroaryl, or 5- to 6-membered heterocyclyl, wherein said (C$_1$-C$_4$)alkyl for $R^5$ is optionally substituted with —OR$^h$, phenyl, or 5- to 6-membered heteroaryl, said 4- to 6-membered heteroaryl and 5- to 6-membered heterocyclyl are each optionally and independently substituted with 1 or 2 groups selected from R$^m$, and wherein said phenyl and 5- to 6-membered heteroaryl of the optional substituents listed for (C$_1$-C$_4$)alkyl in $R^5$ are each optionally and independently substituted with 1 or 2 groups selected from R$^g$, wherein the remaining variables are as described above for the first, second, third, fourth, fifth or sixth embodiment.

In an eighth embodiment, $R^5$ in the compounds of Formula I, II, or III is (C$_1$-C$_4$)alkyl, halo(C$_1$-C$_4$)alkyl, halo, phenyl, —NHC(O)OR$^a$, —C(O)OR$^b$, S(O)$_2$R$^c$, —C(O) OR$^d$, —C(O)NR$^e$R$^f$, —NHC(O)R$^d$, or —O(C$_1$-C$_4$)alkylOR$^e$, —NR$^e$R$^f$, morpholinyl, piperazinyl, or pyrazolyl, wherein said morpholinyl, piperazinyl, and pyrazolyl are each optionally substituted with 1 or 2 groups selected from R$^m$, said (C$_1$-C$_4$)alkyl for R$^5$ is optionally substituted with —OR$^h$, phenyl, pyrazolyl, pyrimidinyl, or pyridinyl, and wherein said phenyl, pyrazolyl, pyrimidinyl, and pyridinyl of the optional substituents listed for (C$_1$-C$_4$)alkyl in R$^5$ are each optionally and independently substituted with 1 or 2 groups selected from R$^g$, wherein the remaining variables are as described above for the first, second, third, fourth, fifth, sixth, or seventh embodiment.

In a ninth embodiment, each R$^f$ in the compounds of Formula I, II, or III is independently hydrogen, (C$_1$-C$_4$) alkyl, phenyl pyrazolyl, pyridinyl, tetrahydropyranyl, piperidinyl, wherein said phenyl pyrazolyl, pyridinyl, tetrahydropyranyl, and piperidinyl are each optionally and independently substituted with (C$_1$-C$_4$)alkyl, wherein the remaining variables are as described above for the first, second, third, fourth, fifth, sixth, seventh, or eighth embodiment.

In a tenth embodiment, each R$^g$ in the compounds of Formula I, II, or III is independently (C$_1$-C$_4$)alkyl, (C$_1$-C$_4$)alkoxy, or halo, wherein the remaining variables are as described above for the first, second, third, fourth, fifth, sixth, seventh, eighth, or ninth embodiment.

In an eleventh embodiment, R$^b$ in the compounds of Formula I, II, or III is (C$_1$-C$_4$)alkyl, phenyl, 5- to 6-membered heteroaryl or 4- to 7-membered heterocyclyl, wherein said phenyl and 5- to 6-membered heteroaryl for R$^b$ are each optionally and independently substituted with 1 or 2 groups selected from halo and (C$_1$-C$_4$)alkoxy, wherein said 4- to 7-membered heterocyclyl for R$^b$ is optionally substituted with =O, and wherein said (C$_1$-C$_4$)alkyl for R$^b$ is optionally substituted with 1 or 2 groups selected from phenyl, —OR$^h$, and —NR$^j$R$^k$, wherein the remaining variables are as described above for the first, second, third, fourth, fifth, sixth, seventh, eighth, ninth, or tenth embodiment.

In a twelfth embodiment, each R$^k$ in the compounds of Formula I, II, or III is independently hydrogen or (C$_1$-C$_4$) alkyl, wherein the remaining variables are as described above for the first, second, third, fourth, fifth, sixth, seventh, eighth, ninth, tenth, or eleventh embodiment.

In a thirteenth embodiment, R$^b$ in the compounds of Formula I, II, or III is (C$_1$-C$_4$)alkyl, phenyl, pyridinyl, pyrazolyl, pyrimidinyl, or piperidinyl, wherein said phenyl, pyridinyl, pyrazolyl, and pyrimidinyl for R$^b$ are each optionally and independently substituted with 1 or 2 groups selected from halo and (C$_1$-C$_4$)alkoxy, wherein said (C$_1$-C$_4$) alkyl for R$^b$ is optionally substituted with 1 or 2 groups selected from phenyl, OH, and NMe$_2$, and wherein said piperidinyl for R$^b$ is optionally substituted with =O, wherein the remaining variables are as described above for the first, second, third, fourth, fifth, sixth, seventh, eighth, ninth, tenth, eleventh, or twelfth embodiment.

In a fourteenth embodiment, R$^3$ in the compounds of Formula I, II, or III is hydrogen, wherein the remaining variables are as described above for the first, second, third, fourth, fifth, sixth, seventh, eighth, ninth, tenth, eleventh, twelfth, or thirteenth embodiment In a fifteenth embodiment, R$^4$ in the compounds of Formula I, II, or III is phenyl or —NHC(O)OR$^a$, wherein the remaining variables are as described above for the first, second, third, fourth, fifth, sixth, seventh, eighth, ninth, tenth, eleventh, twelfth, thirteenth, or fourteenth embodiment.

In a sixteenth embodiment, X in the compounds of Formula I, II, or III is a bond or CH$_2$, wherein the remaining variables are as described above for the first, second, third, fourth, fifth, sixth, seventh, eighth, ninth, tenth, eleventh, twelfth, or thirteenth embodiment.

Also provided herein are pharmaceutical compositions comprising 1) a compound having the Formula I:

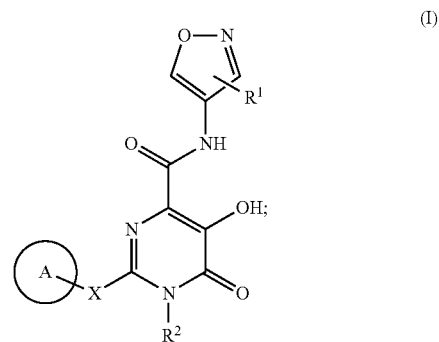

or a pharmaceutically acceptable salt thereof, wherein the variables are as described above for the first, second, third, fourth, fifth, sixth, seventh, eighth, ninth, tenth or eleventh embodiment; and 2) a pharmaceutically acceptable carrier.

Compounds having the Formula I are further disclosed in the Exemplification and are included in the present disclosure. Pharmaceutically acceptable salts thereof as well as the neutral forms are included.

4. Uses, Formulation and Administration

Compounds and compositions described herein are generally useful for modulating the activity of TREX1. In some aspects, the compounds and pharmaceutical compositions described herein inhibit the activity TREX1.

In some aspects, compounds and pharmaceutical compositions described herein are useful in treating a disorder associated with TREX1 function. Thus, provided herein are methods of treating a disorder associated with TREX1 function, comprising administering to a subject in need thereof, a therapeutically effective amount of a compound described herein, or a pharmaceutically acceptable salt thereof, or a pharmaceutical composition comprising a disclosed compound or pharmaceutically acceptable salt thereof. Also provided is the use of a compound described herein, or a pharmaceutically acceptable salt thereof, or a pharmaceutical composition comprising a disclosed compound or pharmaceutically acceptable salt thereof, for the manufacture of a medicament for treating a disorder associated with TREX1 function. Also provided is a compound described herein, or a pharmaceutically acceptable salt thereof, or a pharmaceutical composition comprising a disclosed compound or pharmaceutically acceptable salt thereof, for use in treating a disorder associated with TREX1.

In some aspects, the compounds and pharmaceutical compositions described herein are useful in treating cancer.

In some aspects, the cancer treated by the compounds and pharmaceutical compositions described herein is selected from colon cancer, gastric cancer, thyroid cancer, lung cancer, leukemia, pancreatic cancer, melanoma, multiple melanoma, brain cancer, CNS cancer, renal cancer, prostate cancer, ovarian cancer, leukemia, and breast cancer.

In some aspects, the cancer treated by the compounds and pharmaceutical compositions described herein is selected from lung cancer, breast cancer, pancreatic cancer, colorectal cancer, and melanoma.

In certain aspects, a pharmaceutical composition described herein is formulated for administration to a patient in need of such composition. Pharmaceutical compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the pharmaceutical compositions described herein may be aqueous or oleaginous suspension. These suspensions may be formulated according to techniques known in the art using suitable dispersing or wetting agents and suspending agents.

In some aspects, the pharmaceutical compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the pharmaceutical composition.

EXEMPLIFICATION

Chemical Synthesis

The representative examples that follow are intended to help illustrate the present disclosure, and are not intended to, nor should they be construed to, limit the scope of the invention.

General Synthetic Scheme

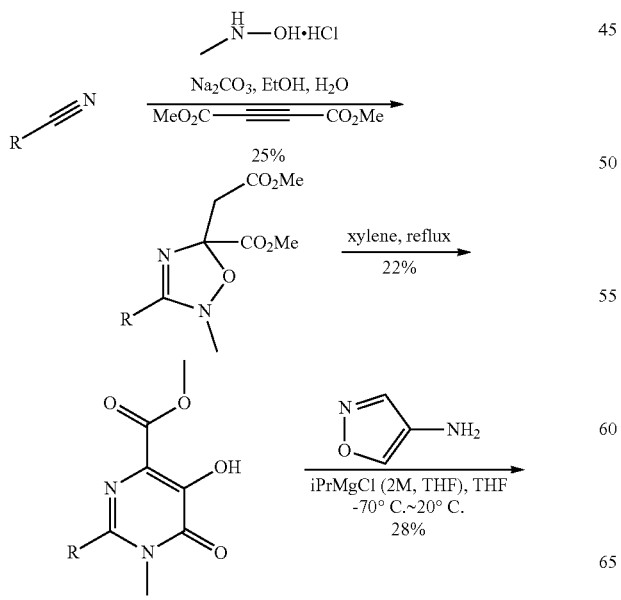

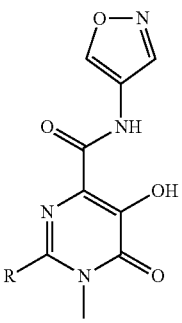

2-(3-bromo-5-methylphenyl)-5-hydroxy-N-(isoxazol-4-yl)-1-methyl-6-oxo-1,6-dihydropyrimidine-4-carboxamide

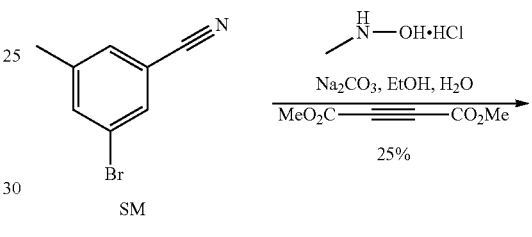

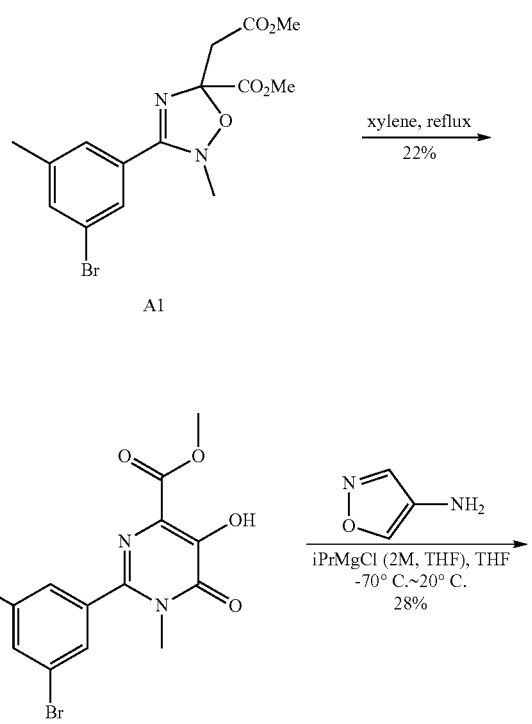

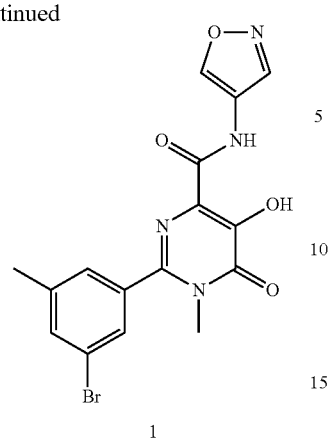

1

Step 1: Synthesis of methyl 3-(3-bromo-5-methylphenyl)-5-(2-methoxy-2-oxoethyl)-2-methyl-2,5-dihydro-1,2,4-oxadiazole-5-carboxylate

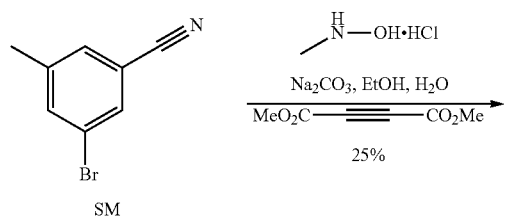

A1

To a stirred solution of SM (5.16 g, 26.341 mmol, 2 equiv), N-methylhydroxylamine hydrochloride (1.10 g, 13.170 mmol, 1.00 equiv) in H$_2$O (25.00 mL), EtOH (25.00 mL) was add Na$_2$CO$_3$ (0.837 g, 7.902 mmol, 0.6 equiv) in portions at room temperature. The resulting solution was stirred for 2 hr at 80° C. Until the reaction mixture is cooled to room temperature, 1,4-dimethyl but-2-ynedioate (2.06 g, 14.488 mmol, 1.1 equiv) was added dropwise. Then, the reaction mixture was stirred for 0.5 h at room temperature. The resulting solution was extracted with 3×30 mL of ethyl acetate and the organic layers combined washed with brine and concentrated under vacuum. The residue was applied onto a silica gel column with ethyl acetate/petroleum ether (1:5). This resulted in 1.3 g of A1 (25% yield) as light yellow oil. ESI-MS m/z=385.0 [M+H]$^+$. Calculated MW: 384.0. $^1$H NMR (400 MHz, Chloroform-d) δ 7.67 (t, J=1.8 Hz, 1H), 7.49 (s, 2H), 3.86 (s, 3H), 3.73 (s, 3H), 3.45 (d, J=16.6 Hz, 1H), 3.19 (s, 3H), 3.07 (d, J=16.6 Hz, 1H), 2.38 (d, J=0.8 Hz, 3H).

The following intermediates were synthesized using similar conditions as those described in the step above along with appropriate starting materials.

TABLE 1

| Structure | Name | Intermediate | LCMS |
|---|---|---|---|
| (cyclobutyl oxadiazole structure) | methyl 3-cyclobutyl-5-(2-methoxy-2-oxoethyl)-2-methyl-2,5-dihydro-1,2,4-oxadiazole-5-carboxylate | A2 | ESI-MS m/z = 271.1 [M + H]+. Calculated MW: 270.1 |
| (cyclopropyl oxadiazole structure) | methyl 3-cyclopropyl-5-(2-methoxy-2-oxoethyl)-2-methyl-2,5-dihydro-1,2,4-oxadiazole-5-carboxylate | A3 | ESI-MS m/z = 257.1 [M + H]+. Calculated MW: 256.1 |

TABLE 1-continued

| Structure | Name | Intermediate | LCMS |
|---|---|---|---|
| 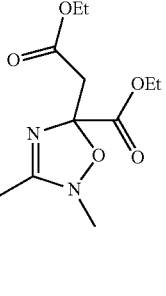 | ethyl 3-(5-bromo-2-methylphenyl)-5-(2-ethoxy-2-oxoethyl)-2-methyl-2,5-dihydro-1,2,4-oxadiazole-5-carboxylate | A4 | ESI-MS m/z = 413.2 [M + H]+. Calculated MW: 412.1 |
| 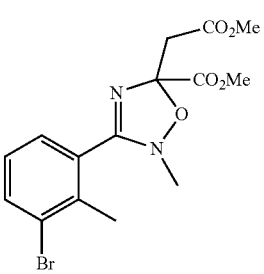 [SMILES: COC(=O)CC1(C(=O)OC)N=C(c2cccc(Br)c2C)N(C)O1] | methyl 3-(3-bromo-2-methylphenyl)-5-(2-methoxy-2-oxoethyl)-2-methyl-2,5-dihydro-1,2,4-oxadiazole-5-carboxylate | A5 | ESI-MS m/z = 385.0 [M + H]+. Calculated MW: 384.0 |
| 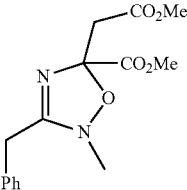 | methyl 3-benzyl-5-(2-methoxy-2-oxoethyl)-2-methyl-2,5-dihydro-1,2,4-oxadiazole-5-carboxylate | A6 | ESI-MS m/z = 307.1 [M + H]+. Calculated MW: 306.1 |
| 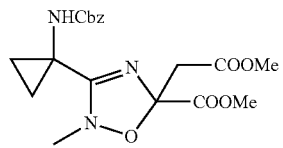 [SMILES: COC(=O)CC1(C(=O)OC)N=C(C2(NC(=O)OCc3ccccc3)CC2)N(C)O1] | methyl 3-(1-(((benzyloxy)carbonyl)amino)cyclopropyl)-5-(2-methoxy-2-oxoethyl)-2-methyl-2,5-dihydro-1,2,4-oxadiazole-5-carboxylate | A7 | ESI-MS m/z = 406.2 [M + H]+. Calculated MW: 405.2 |
| 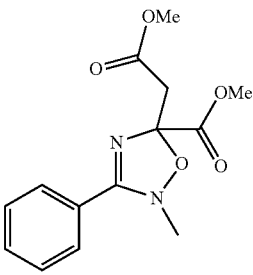 [SMILES: COC(=O)CC1(C(=O)OC)N=C(c2ccccc2)N(C)O1] | methyl 5-(2-methoxy-2-oxoethyl)-2-methyl-3-phenyl-2,5-dihydro-1,2,4-oxadiazole-5-carboxylate | A8 | ESI-MS m/z = 293.6 [M + H]+. Calculated MW: 292.29 |
| 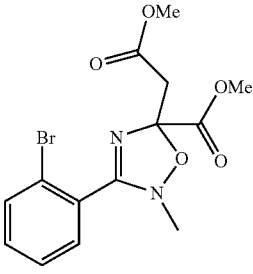 [SMILES: COC(=O)CC1(C(=O)OC)N=C(c2ccccc2Br)N(C)O1] | methyl 3-(2-bromophenyl)-5-(2-methoxy-2-oxoethyl)-2-methyl-2,5-dihydro-1,2,4-oxadiazole-5-carboxylate | A9 | ESI-MS m/z = 373.6 [M + H]+. Calculated MW: 372.19 |

TABLE 1-continued

| Structure | Name | Intermediate | LCMS |
|---|---|---|---|
| 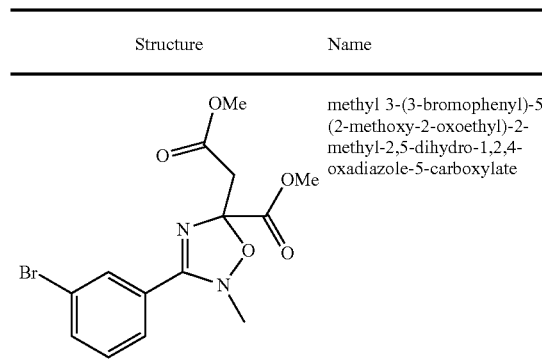 | methyl 3-(3-bromophenyl)-5-(2-methoxy-2-oxoethyl)-2-methyl-2,5-dihydro-1,2,4-oxadiazole-5-carboxylate | A10 | ESI-MS m/z = 373.6 [M + H]+. Calculated MW: 372.19 |
| 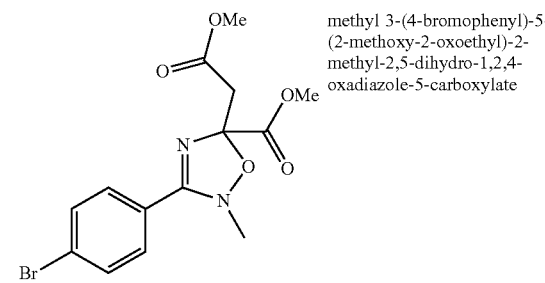 | methyl 3-(4-bromophenyl)-5-(2-methoxy-2-oxoethyl)-2-methyl-2,5-dihydro-1,2,4-oxadiazole-5-carboxylate | A11 | ESI-MS m/z = 373.3 [M + H]+. Calculated MW: 372.19 |
| 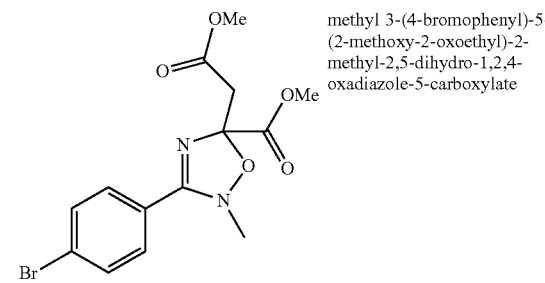 | methyl 3-(4-bromophenyl)-5-(2-methoxy-2-oxoethyl)-2-methyl-2,5-dihydro-1,2,4-oxadiazole-5-carboxylate | A12 | ESI-MS m/z = 373.3 [M + H]+. Calculated MW: 372.19 |
| 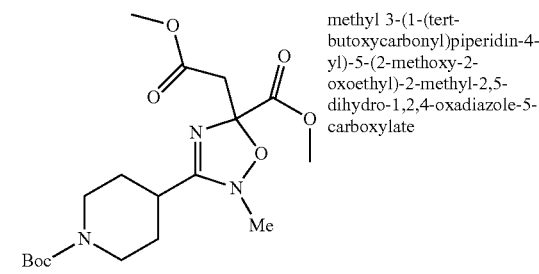 | methyl 3-(1-(tert-butoxycarbonyl)piperidin-4-yl)-5-(2-methoxy-2-oxoethyl)-2-methyl-2,5-dihydro-1,2,4-oxadiazole-5-carboxylate | A13 | ESI-MS m/z = 400.8 [M + H]+. Calculated MW: 399.44 |
| 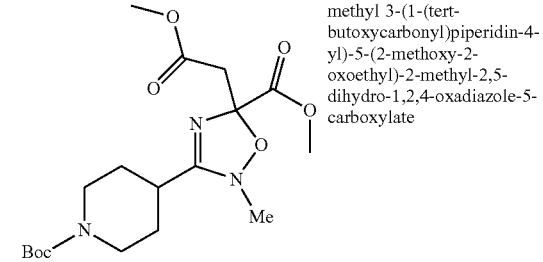 | methyl 3-(1-(tert-butoxycarbonyl)piperidin-4-yl)-5-(2-methoxy-2-oxoethyl)-2-methyl-2,5-dihydro-1,2,4-oxadiazole-5-carboxylate | A14 | ESI-MS m/z = 400.8 [M + H]+. Calculated MW: 399.44 |

TABLE 1-continued

| Structure | Name | Intermediate | LCMS |
|---|---|---|---|
| (structure shown) | methyl 3-(1-(tert-butoxycarbonyl)piperidin-3-yl)-5-(2-methoxy-2-oxoethyl)-2-methyl-2,5-dihydro-1,2,4-oxadiazole-5-carboxylate | A15 | ESI-MS m/z = 400.6 [M + H]+. Calculated MW: 399.44 |
| (structure shown) | methyl 3-(1-(tert-butoxycarbonyl)piperidin-2-yl)-5-(2-methoxy-2-oxoethyl)-2-methyl-2,5-dihydro-1,2,4-oxadiazole-5-carboxylate | A16 | ESI-MS m/z = 400.8 [M + H]+. Calculated MW: 399.44 |
| (structure shown) | methyl 3-(3-bromo-2-(2-((tert-butyldimethylsilyl)oxy)ethoxy)phenyl)-5-(2-methoxy-2-oxoethyl)-2-methyl-2,5-dihydro-1,2,4-oxadiazole-5-carboxylate | A17 | ESI-MS m/z = 451.0 [M + H]+. Calculated MW: 450.0 |

Step 2: Synthesis of methyl 2-(3-bromo-5-methylphenyl)-5-hydroxy-1-methyl-6-oxo-1,6-dihydropyrimidine-4-carboxylate B1

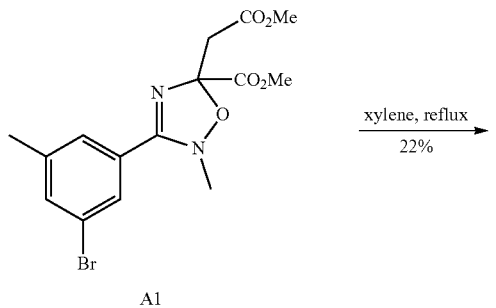

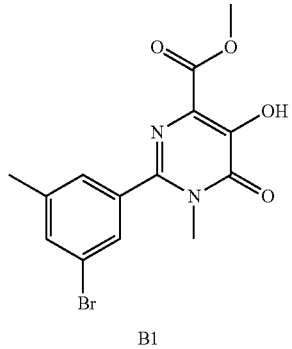

Into a 100-mL round-bottom flask, was placed methyl 3-(3-bromo-5-methylphenyl)-5-(2-methoxy-2-oxoethyl)-2-methyl-2,5-dihydro-1,2,4-oxadiazole-5-carboxylate (1.00 g, 2.596 mmol, 1.00 equiv), xylene (20.00 mL). The resulting solution was stirred for 5 hr at 145° C. The reaction mixture was cooled down to room temperature. The solids were collected by filtration washed with hexane. The solid was dried under reduced pressure. This resulted in 210 mg of methyl 2-(3-bromo-5-methylphenyl)-5-hydroxy-1-methyl- 6-oxo-1,6-dihydropyrimidine-4-carboxylate (22% yield) as a white solid. ESI-MS m/z=353.0 [M+H]+. Calculated MW: 352.0

The following intermediates were synthesized using similar conditions as those described in the step above along with appropriate starting materials.

TABLE 2

| Structure | Name | Intermediate | LCMS |
|---|---|---|---|
| 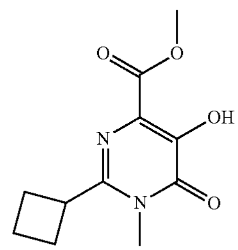 [SMILES: COC(=O)c1nc(C2CCC2)n(C)c(=O)c1O] | methyl 2-cyclobutyl-5-hydroxy-1-methyl-6-oxo-1,6-dihydropyrimidine-4-carboxylate | B2 | ESI-MS m/z = 239.1 [M + H]+. Calculated MW: 238.1 |
| 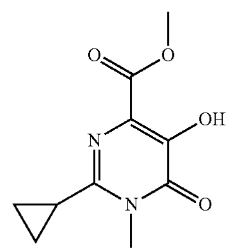 [SMILES: COC(=O)c1nc(C2CC2)n(C)c(=O)c1O] | methyl 2-cyclopropyl-5-hydroxy-1-methyl-6-oxo-1,6-dihydropyrimidine-4-carboxylate | B3 | ESI-MS m/z = 225.1 [M + H]+. Calculated MW: 224.0 |
| 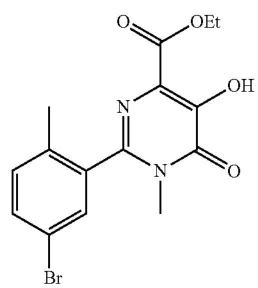 [SMILES: CCOC(=O)c1nc(-c2cc(Br)ccc2C)n(C)c(=O)c1O] | ethyl 2-(5-bromo-2-methylphenyl)-5-hydroxy-1-methyl-6-oxo-1,6-dihydropyrimidine-4-carboxylate | B4 | ESI-MS m/z = 365.0 [M − H]−. Calculated MW: 366.0 |
| 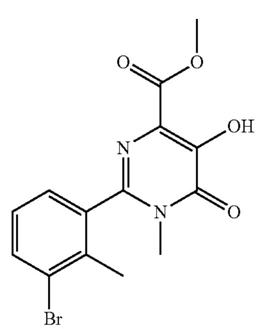 [SMILES: COC(=O)c1nc(-c2cccc(Br)c2C)n(C)c(=O)c1O] | methyl 2-(3-bromo-2-methylphenyl)-5-hydroxy-1-methyl-6-oxo-1,6-dihydropyrimidine-4-carboxylate | B5 | ESI-MS m/z = 353.0 [M + H]+. Calculated MW: 352.0 |
| 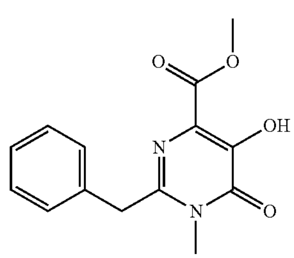 [SMILES: COC(=O)c1nc(Cc2ccccc2)n(C)c(=O)c1O] | methyl 2-benzyl-5-hydroxy-1-methyl-6-oxo-1,6-dihydropyrimidine-4-carboxylate | B6 | ESI-MS m/z = 275.1 [M + H]+. Calculated MW: 274.1 |

TABLE 2-continued

| Structure | Name | Intermediate | LCMS |
|---|---|---|---|
| 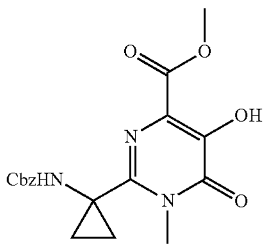 [SMILES: COC(=O)c1nc(C2(NC(=O)OCc3ccccc3)CC2)n(C)c(=O)c1O] | methyl 2-(1-(((benzyloxy)carbonyl)amino)cyclopropyl)-5-hydroxy-1-methyl-6-oxo-1,6-dihydropyrimidine-4-carboxylate | B7 | ESI-MS m/z = 374.4 [M + H]+. Calculated MW: 373.1 |
| 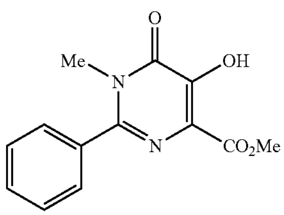 [SMILES: COC(=O)c1nc(-c2ccccc2)n(C)c(=O)c1O] | methyl 5-hydroxy-1-methyl-6-oxo-2-phenyl-1,6-dihydropyrimidine-4-carboxylate | B8 | ESI-MS m/z = 261.3 [M + H]+. Calculated MW: 260.2 |
| 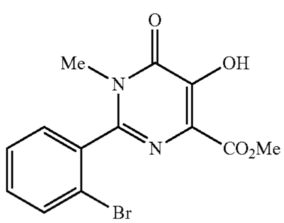 [SMILES: COC(=O)c1nc(-c2ccccc2Br)n(C)c(=O)c1O] | methyl 2-(2-bromophenyl)-5-hydroxy-1-methyl-6-oxo-1,6-dihydropyrimidine-4-carboxylate | B9 | ESI-MS m/z = 341.2 [M + H]+. Calculated MW: 339.1 |
| 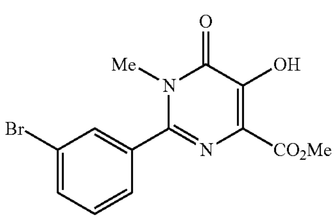 [SMILES: COC(=O)c1nc(-c2cccc(Br)c2)n(C)c(=O)c1O] | methyl 2-(3-bromophenyl)-5-hydroxy-1-methyl-6-oxo-1,6-dihydropyrimidine-4-carboxylate | B10 | ESI-MS m/z = 341.6 [M + H]+. Calculated MW: 339.1 |
| 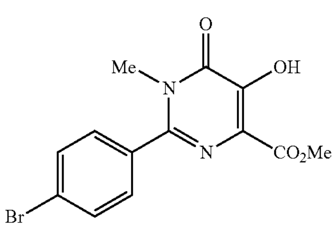 [SMILES: COC(=O)c1nc(-c2ccc(Br)cc2)n(C)c(=O)c1O] | methyl 2-(4-bromophenyl)-5-hydroxy-1-methyl-6-oxo-1,6-dihydropyrimidine-4-carboxylate | B11 | ESI-MS m/z = 341.4 [M + H]+. Calculated MW: 339.1 |
| 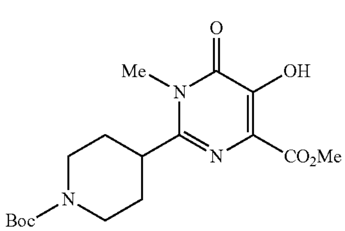 [SMILES: COC(=O)c1nc(C2CCN(C(=O)OC(C)(C)C)CC2)n(C)c(=O)c1O] | methyl 2-(1-(tert-butoxycarbonyl)piperidin-4-yl)-5-hydroxy-1-methyl-6-oxo-1,6-dihydropyrimidine-4-carboxylate | B12 | ESI-MS m/z = 368.3 [M + H]+. Calculated MW: 367.40 |

TABLE 2-continued

| Structure | Name | Intermediate | LCMS |
|---|---|---|---|
| 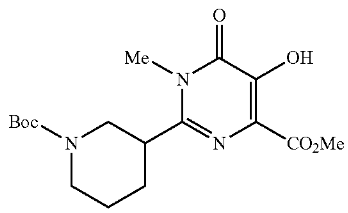 [SMILES: COC(=O)c1nc(C2CCCN(C(=O)OC(C)(C)C)C2)n(C)c(=O)c1O] | methyl 2-(1-(tert-butoxycarbonyl)piperidin-3-yl)-5-hydroxy-1-methyl-6-oxo-1,6-dihydropyrimidine-4-carboxylate | B13 | ESI-MS m/z = 368.5 [M + H]+. Calculated MW: 367.40 |
| 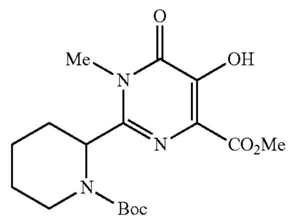 [SMILES: COC(=O)c1nc(C2CCCCN2C(=O)OC(C)(C)C)n(C)c(=O)c1O] | methyl 3-(1-(tert-butoxycarbonyl)piperidin-2-yl)-5-(2-methoxy-2-oxoethyl)-2-methyl-2,5-dihydro-1,2,4-oxadiazole-5-carboxylate | B14 | ESI-MS m/z = 368.3 [M + H]+. Calculated MW: 367.40 |
| 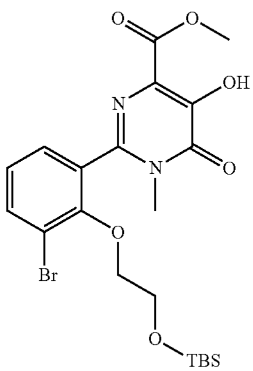 | methyl 2-(3-bromo-2-(2-((tert-butyldimethylsilyl)oxy)ethoxy)phenyl)-5-hydroxy-1-methyl-6-oxo-1,6-dihydropyrimidine-4-carboxylate | B15 | ESI-MS m/z = 513.1 [M + H]+. Calculated MW: 512.1 |

Step 3: Synthesis of 2-(3-bromo-5-methylphenyl)-5-hydroxy-N-(isoxazol-4-yl)-1-methyl-6-oxo-1,6-dihydropyrimidine-4-carboxamide (Example 1)

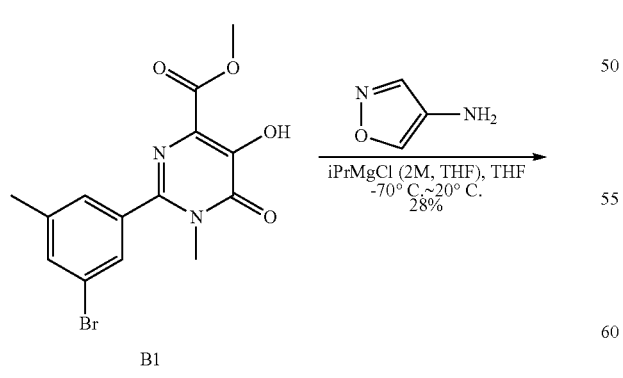

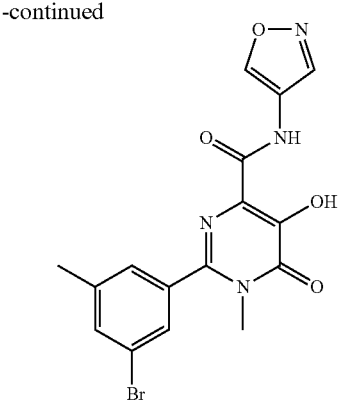

Into a 8-mL sealed tube, was placed methyl 2-(3-bromo-5-methylphenyl)-5-hydroxy-1-methyl-6-oxo-1,6-dihydropyrimidine-4-carboxylate (100.00 mg, 0.283 mmol, 1.00 equiv), THF (2.50 mL), 1,2-oxazol-4-amine (71.42 mg, 0.849 mmol, 3.00 equiv). This was followed by the addition of a solution of iPrMgCl (2M, 0.64 mL, 4.50 equiv) dropwise with stirring at −70 degrees C. The resulting solution was stirred for 1 hr at room temperature. The reaction was then quenched by the addition of 2 mL of sat. NH$_4$Cl (aq.). The pH value of the solution was adjusted to 3 with HCl (4 M). The resulting solution was extracted with 3×5 mL of dichloromethane and the organic layers combined and concentrated under vacuum. The crude product was purified by Prep-HPLC (CH₃CN/H₂O/FA). This resulted in 32.9 mg 2-(3-bromo-5-methylphenyl)-5-hydroxy-N-(isoxazol-4-yl)-1-methyl-6-oxo-1,6-dihydropyrimidine-4-carboxamide (28% yield) as a white solid. ESI-MS m/z=405.0 [M+H]⁺. Calculated MW: 404.0. ¹H NMR (300 MHz, DMSO-d$_6$) δ 11.82 (s, 1H), 10.95 (s, 1H), 9.31 (s, 1H), 8.87 (s, 1H), 7.68 (s, 1H), 7.62 (s, 1H), 7.48 (s, 1H), 3.30 (s, 3H), 2.39 (s, 3H).

The following examples were synthesized using similar conditions as those described in the step above along with appropriate starting materials.

TABLE 3

| Example | Structure | Name | LCMS | NMR |
| --- | --- | --- | --- | --- |
| 2 | 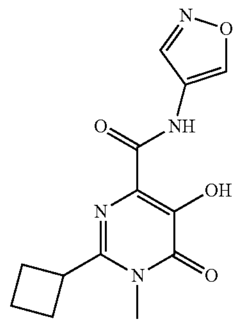 [SMILES: Cn1c(C2CCC2)nc(C(=O)Nc2cnoc2)c(O)c1=O] | 2-cyclobutyl-5-hydroxy-N-(isoxazol-4-yl)-1-methyl-6-oxo-1,6-dihydropyrimidine-4-carboxamide | ESI-MS m/z = 291.1 [M + H]+. Calculated MW: 290.1 | 1H NMR (300 MHz, DMSO-d6) δ: 11.60 (s, 1H), 10.72 (s, 1H), 9.32 (s, 1H), 8.93 (s, 1H), 3.79-3.68 (m, 1H), 3.39 (s, 3H), 2.65-2.51 (m, 2H), 2.35-2.23 (m, 2H), 2.09-1.92 (m, 1H), 1.90-1.72 (m, 1H). |
| 3 | 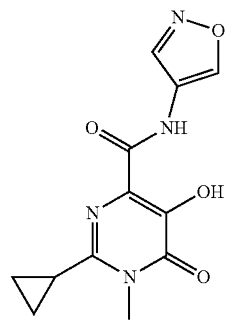 [SMILES: Cn1c(C2CC2)nc(C(=O)Nc2cnoc2)c(O)c1=O] | 2-cyclopropyl-5-hydroxy-N-(isoxazol-4-yl)-1-methyl-6-oxo-1,6-dihydropyrimidine-4-carboxamide | ESI-MS m/z = 277.2 [M + H]+. Calculated MW: 276.1 | 1H NMR (300 MHz, DMSO-d6) δ 11.52 (s, 1H), 10.59 (s, 1H), 9.30 (s, 1H), 8.90 (s, 1H), 3.64 (s, 3H), 2.20-2.22 (m, 1H), 1.27-1.16 (m, 2H), 1.06-0.94 (m, 2H). |
| 4 | 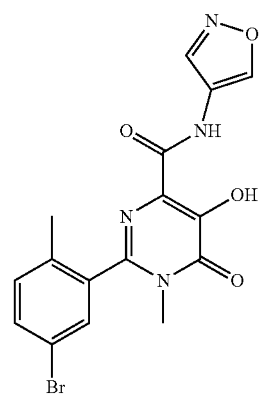 [SMILES: Cc1ccc(Br)cc1-c1nc(C(=O)Nc2cnoc2)c(O)c(=O)n1C] | 2-(5-bromo-2-methylphenyl)-5-hydroxy-N-(isoxazol-4-yl)-1-methyl-6-oxo-1,6-dihydropyrimidine-4-carboxamide | ESI-MS m/z = 405.1[M + H]+. Calculated MW: 404.0 | 1H NMR (400 MHz, DMSO-d6) δ 11.91 (s, 1H), 11.01 (s, 1H), 9.29 (s, 1H), 8.85 (s, 1H), 7.71 (d, J = 2.0 Hz, 1H), 7.66-7.63 (m, 1H), 7.36 (d, J = 8.0 Hz, 1H), 3.17 (s, 3H), 2.16(s, 3H). |
| 5 | 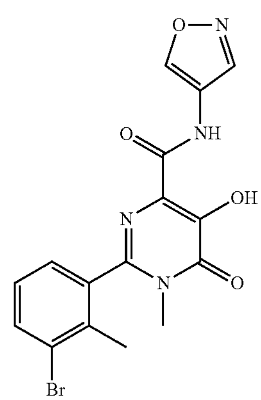 [SMILES: Cc1c(Br)cccc1-c1nc(C(=O)Nc2cnoc2)c(O)c(=O)n1C] | 2-(3-bromo-2-methylphenyl)-5-hydroxy-N-(isoxazol-4-yl)-1-methyl-6-oxo-1,6-dihydropyrimidine-4-carboxamide | ESI-MS m/z = 405.0 [M + H]+. Calculated MW: 404.0 | 1H NMR (300 MHz, DMSO-d6) δ 11.93 (s, 1H), 10.98 (s, 1H), 9.29 (s, 1H), 8.85 (s, 1H), 7.82-7.79 (m, 1H), 7.52-7.49 (m, 1H), 7.33 (t, J = 7.8 Hz, 1H), 3.17 (s, 3H), 2.26 (s, 3H). |

TABLE 3-continued

| Example | Structure | Name | LCMS | NMR |
|---|---|---|---|---|
| 6 | (structure) | 2-benzyl-5-hydroxy-N-(isoxazol-4-yl)-1-methyl-6-oxo-1,6-dihydropyrimidine-4-carboxamide | ESI-MS m/z = 327.1 [M + H]+. Calculated MW: 326.1 | 1H NMR (300 MHz, DMSO-d6) δ 11.60 (s, 1H), 11.09 (s, 1H), 9.33 (s, 1H), 8.92 (s, 1H), 7.39-7.26 (m, 5H), 4.28 (s, 2H), 3.34 (s, 3H). |
| 7 | (structure) | benzyl (1-(5-hydroxy-4-(isoxazol-4-ylcarbamoyl)-1-methyl-6-oxo-1,6-dihydropyrimidin-2-yl)cyclopropyl)carbamate | ESI-MS m/z = 426.1 [M + H]+. Calculated MW: 425.1 | 1H NMR (300 MHz, DMSO-d6) δ 11.66 (s, 1H), 10.65 (s, 1H), 9.32 (s, 1H), 8.93 (s, 1H), 8.30 (s, 1H), 7.33-7.10 (m, 5H), 4.97 (s, 2H), 3.57 (s, 3H), 1.74 (s, 2H), 1.16-1.12 (m, 2H). |

Synthesis of 5-hydroxy-N-(isoxazol-4-yl)-1-methyl-6-oxo-2-phenyl-1,6-dihydropyrimidine-4-carboxamide (Example 8)

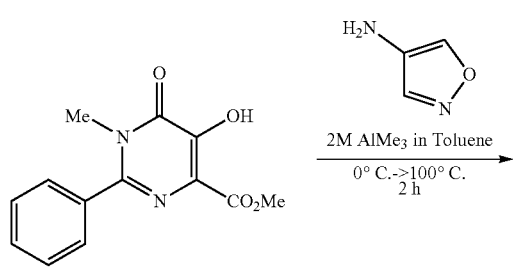

Methyl 5-hydroxy-1-methyl-6-oxo-2-phenyl-1,6-dihydropyrimidine-4-carboxylate (200 mg, 0.77 mmol, 1 equiv) and isoxazol-4-amine (0.096 g, 1.15 mmol, 1.5 equiv) were dissolved in toluene (1 mL) and the mixture was cooled to 0° C. To this 2M trimethylaluminum in toluene (0.768 ml, 1.53 mmol, 2.0 equiv) was added drop wise at 0° C. The reaction mixture was then heated at 100° C. for 2 h and then quenched with saturated sodium bicarbonate solution (0.2 ml) and to it ethyl acetate (10 ml) was added. The reaction mixture was then dried over anhydrous Na2SO4 and filtered off. The solid was washed with ethyl acetate (3×10 ml) and combined organic layer was concentrated under reduced pressure. The crude product was purified by reverse-phase HPLC to give 5-hydroxy-N-(isoxazol-4-yl)-1-methyl-6-oxo-2-phenyl-1,6-dihydropyrimidine-4-carboxamide, 8 (25 mg, 15%). ESI-MS m/z=313.2 [M+H]+. Calculated MW: 312.29. $^1$H NMR (400 MHz, DMSO-d6): δ 9.13 (s, 1H), 8.78 (s, 1H), 7.42-7.50 (m, 5H), 3.22 (s, 3H).

Scheme: Synthesis of 2-chloro-N-(isoxazol-4-yl)-5-methoxy-1-methyl-6-oxo-1,6-dihydropyrimidine-4-carboxamide (C)

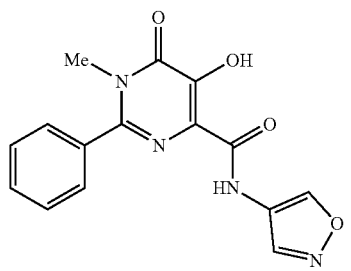

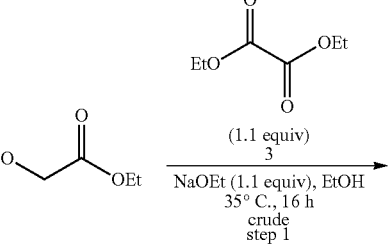

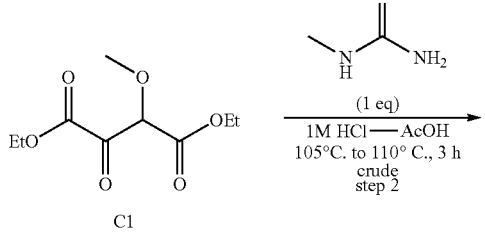

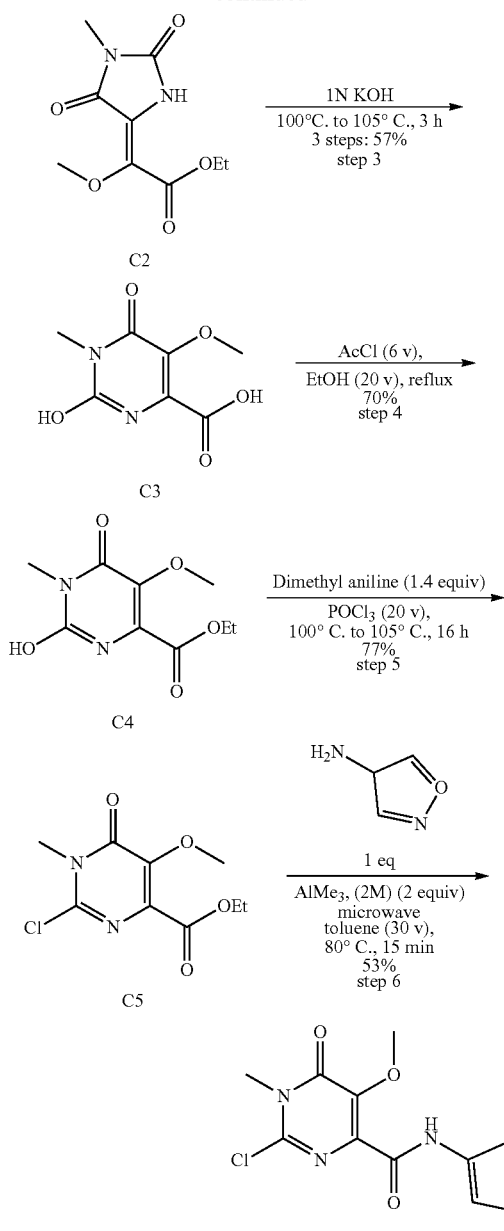

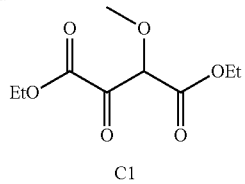

Into a 1000-mL 3-necked round-bottom flask purged and maintained with an inert atmosphere of nitrogen, was placed ethanol (600.0 mL), sodium ethanolate (31.7 g, 0.470 mmol, 1.10 equiv), ethyl oxalate (68.00 g, 465.6 mmol, 1.10 equiv) was added at room temperature. This was followed by the addition of ethyl 2-methoxyacetate (50.00 g, 423.3 mmol, 1.00 equiv) dropwise with stirring at room temperature. The resulting solution was stirred for 1 overnight at 35° C. The resulting mixture was concentrated under vacuum to remove most of ethanol. The pH value of the solution was adjusted to 3 with hydrogen chloride (1 mol/L) at 0° C. The resulting solution was extracted with 4×500 mL of ethyl acetate dried over anhydrous sodium sulfate and concentrated under vacuum. This resulted in 90 g (crude) of 1,4-diethyl 2-methoxy-3-oxobutanedioate (1) as brown oil.

Step 2: Synthesis of ethyl 2-methoxy-2-[(4E)-1-methyl-2,5-dioxoimidazolidin-4-ylidene]acetate (2)

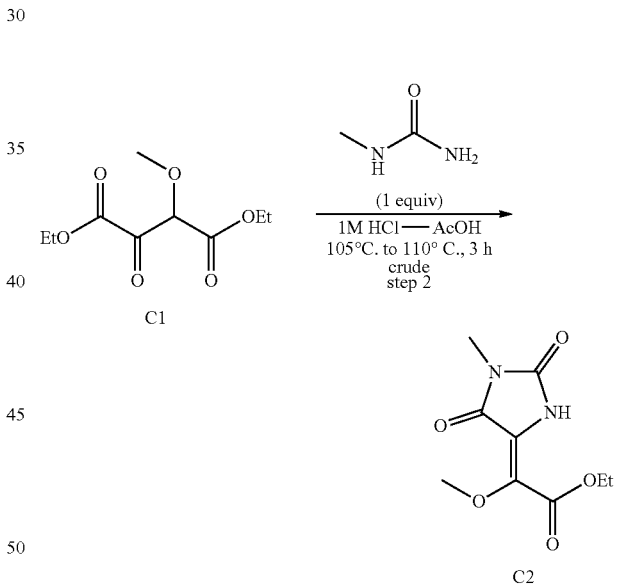

Into a 2000-mL round-bottom flask, was placed 1,4-diethyl 2-methoxy-3-oxobutanedioate (1) (90.00 g, 412.5 mmol, 1.00 equiv), methylurea (30.60 g, 412.5 mmol, 1.00 equiv), acetic acid (1200.0 mL), hydrogen chloride (400.0 mL, gas, 4 mol in dioxane). The resulting solution was stirred for 3 h at 105° C. The resulting mixture was concentrated under vacuum. The resulting mixture was washed with 1×500 ml of hexane. This resulted in 90 g (crude) of ethyl 2-methoxy-2-[(4E)-1-methyl-2,5-dioxoimidazolidin-4-ylidene]acetate (2) as a brown solid. 1H NMR (300 MHz, Chloroform-d) δ 8.75 (s, 1H), 7.47 (s, 0.4H), 5.09 (s, 2H), 4.51-4.30 (m, 3H), 3.85 (s, 1H), 3.84 (s, 3H), 3.12 (s, 3H), 3.07 (s, 1H), 2.14 (d, J=12.9 Hz, 1H), 1.45-1.42 (m, 2H), 1.42-1.37 (m, 3H).

Step 1: Synthesis of 1,4-diethyl 2-methoxy-3-oxobutanedioate (1)

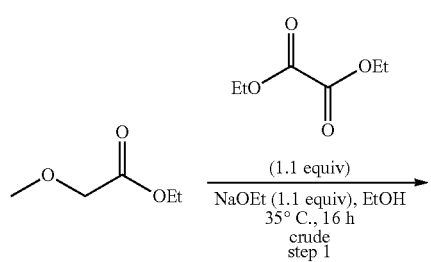

Step 3. Synthesis of 2-hydroxy-5-methoxy-1-methyl-6-oxopyrimidine-4-carboxylic acid (3)

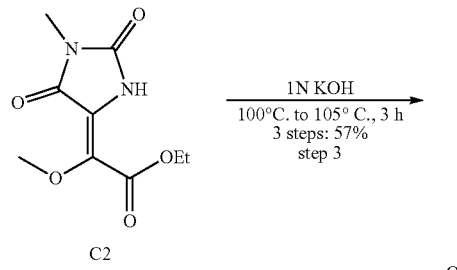

Into a 2000-mL round-bottom flask, was placed ethyl 2-methoxy-2-[(4E)-1-methyl-2,5-dioxoimidazolidin-4-ylidene]acetate (2) (80.00 g, 350.6 mmol, 1.00 equiv), potassium hydroxide (1M in water) (1400.0 mL). The resulting solution was stirred for 3 h at 105° C. The reaction mixture was cooled to 0° C. with a water/ice bath. The pH value of the solution was adjusted to 3 with hydrogen chloride (12 mol/L) at 0° C., the solids were collected by filtration and the precipitate was dried in vacuo. This resulted in 40 g of 2-hydroxy-5-methoxy-1-methyl-6-oxopyrimidine-4-carboxylic acid (3) (yield 57%) as a white solid. $^1$H NMR (300 MHz, DMSO-d6) δ 14.35 (s, 1H), 10.91 (s, 1H), 3.68 (s, 3H), 3.14 (s, 3H).

Step 4. Synthesis of ethyl 2-hydroxy-5-methoxy-1-methyl-6-oxopyrimidine-4-carboxylate (4)

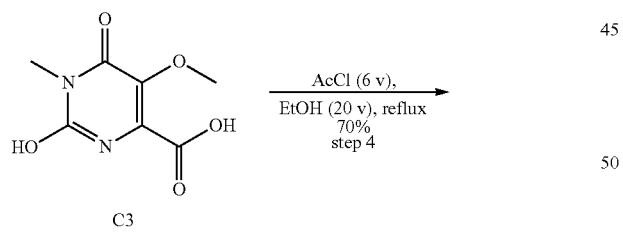

Into a 1000-mL 3-necked round-bottom flask purged and maintained with an inert atmosphere of argon, was placed 2-hydroxy-5-methoxy-1-methyl-6-oxopyrimidine-4-carboxylic acid (3) (20 g, 0.10 mmol, 1.00 equiv), ethanol (400.0 mL). This was followed by the addition of acetyl chloride (117.7 g, 1.500 mmol, 15.00 equiv) dropwise with stirring at 0° C. The resulting solution was heated to reflux for 1 overnight. The reaction mixture was cooled with a water/ice bath. The solids were collected by filtration. This resulted in 16 g of ethyl 2-hydroxy-5-methoxy-1-methyl-6-oxopyrimidine-4-carboxylate (4) (yield: 70%) as a white solid. $^1$H NMR (400 MHz, DMSO-d6) δ 11.08 (s, 1H), 4.32 (q, J=7.1 Hz, 2H), 3.70 (s, 3H), 3.15 (s, 3H), 1.31 (t, J=7.1 Hz, 3H).

Step 5. Synthesis of ethyl 2-chloro-5-methoxy-1-methyl-6-oxopyrimidine-4-carboxylate (5)

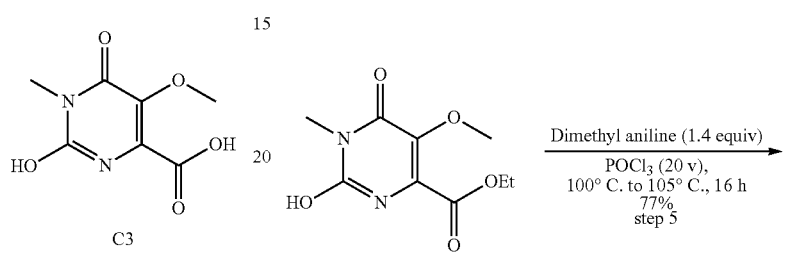

Into a 1-L 3-necked round-bottom flask purged and maintained with an inert atmosphere of argon, was placed ethyl 2-hydroxy-5-methoxy-1-methyl-6-oxopyrimidine-4-carboxylate (4) (16.0 g, 70.1 mmol, 1.00 equiv), dimethylaniline (1.20 g, 98.2 mmol, 1.40 equiv), phosphoryl trichloride (320.0 mL). The resulting solution was stirred for 1 overnight at 100° C. The resulting mixture was concentrated under vacuum. The residue was applied onto a silica gel column with ethyl acetate/petroleum ether (1/10-1/4). This resulted in 13.3 g of ethyl 2-chloro-5-methoxy-1-methyl-6-oxopyrimidine-4-carboxylate (5) (yield 77.0%) as a yellow solid. $^1$H NMR (300 MHz, DMSO-d6) δ 4.32 (q, J=7.1 Hz, 2H), 3.84 (s, 3H), 3.54 (s, 3H), 1.30 (t, J=7.1 Hz, 3H).

Step 6. Synthesis of 2-chloro-5-methoxy-1-methyl-N-(1, 2-oxazol-4-yl)-6-oxopyrimidine-4-carboxamide (6)

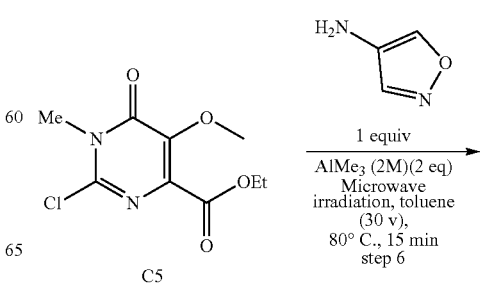

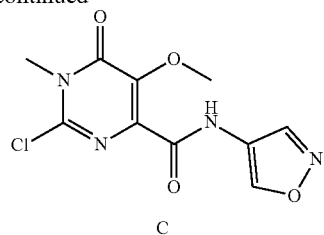

C

To a stirred solution of ethyl 2-chloro-5-methoxy-1-methyl-6-oxopyrimidine-4-carboxylate (5) (1.00 g, 4.05 mmol, 1.00 equiv) and 1,2-oxazol-4-amine (340.9 mg, 4.050 mmol, 1.00 equiv) in toluene (15.0 mL) was added trimethylaluminum (2 mol in toluene) (4.1 mL, 8.10 mmol, 2.00 equiv) at room temperature under argon atmosphere. The resulting solution was stirred with microwave radiation for 15 min at 80° C. The reaction mixture was quenched with water/ice at 0° C. The resulting solution was extracted with 3×40 mL of ethyl acetate, the combined organic layers were washed with brine (1×30 mL), dried over anhydrous sodium sulfate and concentrated under vacuum. The residue was applied onto a silica gel column with ethyl acetate/petroleum ether (1/10-1/1). This resulted in 650 mg of 2-chloro-5-methoxy-1-methyl-N-(1, 2-oxazol-4-yl)-6-oxopyrimidine-4-carboxamide (6) (yield 53.0%) as a light yellow solid. ESI-MS m/z=285.2 [M+H]$^+$. Calculated MW: 284.2 $^1$H NMR (300 MHz, DMSO-d6) δ 10.84 (s, 1H), 9.28 (s, 1H), 8.78 (s, 1H), 3.86 (s, 3H), 3.62 (s, 3H).

The following examples and intermediates were synthesized using similar conditions as those described in the step, above, along with appropriate starting materials.

TABLE 4

| Example | Structure | Name | LCMS | NMR |
|---|---|---|---|---|
| 9 | 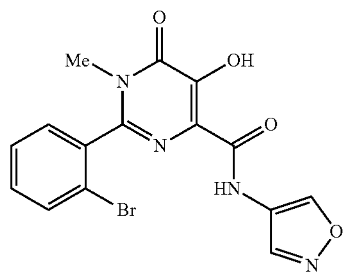 [SMILES: Cn1c(-c2ccccc2Br)nc(C(=O)Nc2cnoc2)c(O)c1=O] | 2-(2-bromophenyl)-5-hydroxy-N-(isoxazol-4-yl)-1-methyl-6-oxo-1,6-dihydropyrimidine-4-carboxamide | ESI-MS m/z = 393.2 [M + H]+. Calculated MW: 391.18 | 1H NMR(400 MHz, DMSO-d6): δ 12.01 (s, 1H), 11.07 (s, 1H), 9.31 (s, 1H), 8.86 (s, 1H), 7.83 (d, J = 8.0 Hz, 1H), 7.67-7.68 (m, 1H), 7.62 (t, J = 7.6 Hz, 1H), 7.53 (t, J = 7.6 Hz, 1H), 3.20 (s, 3H). |
| 10 | 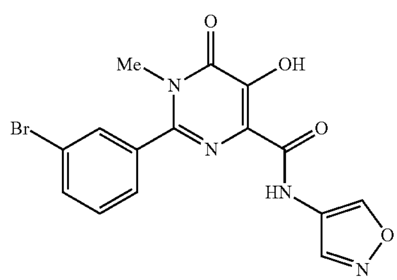 [SMILES: Cn1c(-c2cccc(Br)c2)nc(C(=O)Nc2cnoc2)c(O)c1=O] | 2-(3-bromophenyl)-5-hydroxy-N-(isoxazol-4-yl)-1-methyl-6-oxo-1,6-dihydropyrimidine-4-carboxamide | ESI-MS m/z = 393.1 [M + H]+. Calculated MW: 391.15 | (400 MHz, DMSO-d6): δ 11.83 (s, 1H), 11.03 (s, 1H,), 9.30 (s, 1H), 8.87 (s, 1H), 7.89 (s, 1H), 7.77 (d, J = 8.0 Hz, 1H), 7.68 (d, J = 7.6 Hz, 1H), 7.52 (t, J = 7.6 Hz, 1H), 3.31 (s, 3H). |
| 11 | 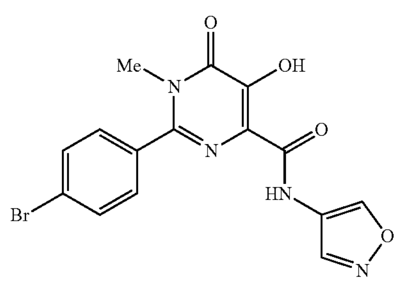 [SMILES: Cn1c(-c2ccc(Br)cc2)nc(C(=O)Nc2cnoc2)c(O)c1=O] | 2-(4-bromophenyl)-5-hydroxy-N-(isoxazol-4-yl)-1-methyl-6-oxo-1,6-dihydropyrimidine-4-carboxamide | ESI-MS m/z = 393.6 [M + H]+. Calculated MW: 391.18 | 1H NMR (400 MHz, DMSO-d6): δ 11.81 (s, 1H), 11.18 (s, 1H), 9.30 (s, 1H), 8.86 (s, 1H), 7.77 (d, J = 7.6 Hz, 2H), 7.63 (t, J = 7.2 Hz, 2H), 3.32 (s, 3H). |
| 12 | 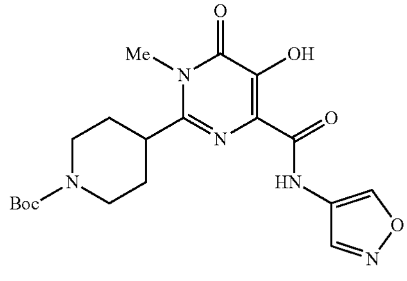 [SMILES: Cn1c(C2CCN(C(=O)OC(C)(C)C)CC2)nc(C(=O)Nc2cnoc2)c(O)c1=O] | tert-butyl 4-(5-hydroxy-4-(isoxazol-4-ylcarbamoyl)-1-methyl-6-oxo-1,6-dihydropyrimidin-2-yl)piperidine-1-carboxylate | ESI-MS m/z = 320.7 [M$^+$ − BOC]+. Calculated MW: 419.44 | 1H NMR (400 MHz, DMSO-d6): δ 11.57 (s, 1H), 10.57 (s, 1H), 9.32 (s, 1H), 8.93 (s, 1H), 4.11 (bs, 2H), 3.58 (s, 3H), 3.04-3.07(m, 1H), 2.86 (bs, 2H), 1.84 (bs, 4H), 1.43 (s, 9H). |

TABLE 4-continued

| Example | Structure | Name | LCMS | NMR |
|---|---|---|---|---|
| 13 | 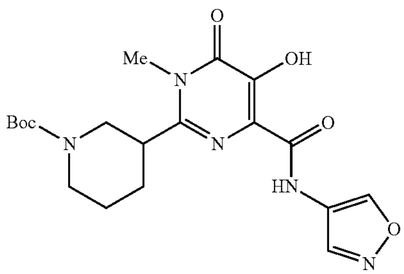 [SMILES: Cn1c(C2CCCN(C(=O)OC(C)(C)C)C2)nc(C(=O)Nc2cnoc2)c(O)c1=O] | tert-butyl 3-(5-hydroxy-4-(isoxazol-4-ylcarbamoyl)-1-methyl-6-oxo-1,6-dihydropyrimidin-2-yl)piperidine-1-carboxylate | ESI-MS m/z = 420.7 [M + H]+. Calculated MW: 419.44 | 1H NMR (400 MHz, DMSO-d6): δ 11.53 (s, 1H), 10.51 (s, 1H), 9.31 (s, 1H), 8.93 (s, 1H), 4.02-4.11 (m, 2H), 3.55 (s, 3H), 3.18-3.24 (m, 1H), 2.89-2.91 (m, 1H), 2.00-2.07 (m, 1H), 1.70-1.95 (m, 3H), 1.48-1.51 (m, 1H), 1.41 (s, 9H). |
| 14 | 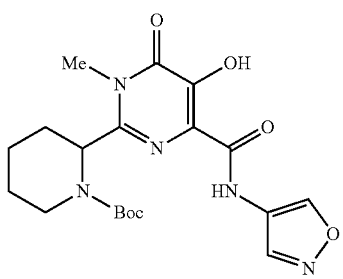 [SMILES: Cn1c(C2CCCCN2C(=O)OC(C)(C)C)nc(C(=O)Nc2cnoc2)c(O)c1=O] | tert-butyl 2-(5-hydroxy-4-(isoxazol-4-ylcarbamoyl)-1-methyl-6-oxo-1,6-dihydropyrimidin-2-yl)piperidine-1-carboxylate | ESI-MS m/z = 420.4 [M + H]+. Calculated MW: 419.44 | 1H NMR (400 MHz, DMSO-d6): δ 11.35 (s, 1H), 10.22 (s, 1H), 9.33 (s, 1H), 8.89 (s, 1H), 5.08 (s, 1H), 3.55-3.62 (m, 1H), 3.48 (s, 3H), 3.30 (bs, 1H), 2.19 (bs, 1H), 1.86 (bs, 2H), 1.59 (bs, 2H), 1.46 (bs, 1H), 1.32 (s, 9H). |

The following intermediate was synthesized using similar conditions as those described above along with appropriate starting materials.

TABLE 5

| Intermediate | Structure | Name | LCMS | NMR |
|---|---|---|---|---|
| C1 | 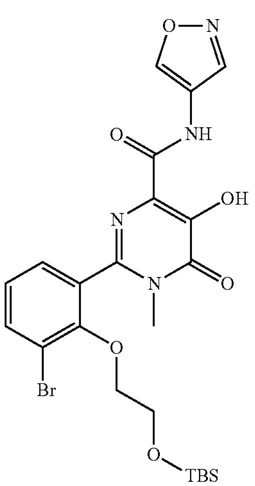 | 2-(3-bromo-2-(2-((tert-butyldimethylsilyl)oxy)ethoxy)phenyl)-5-hydroxy-N-(isoxazol-4-yl)-1-methyl-6-oxo-1,6-dihydropyrimidine-4-carboxamide | ESI-MS m/z = 451.0 [M + H]+. Calculated MW: 450.0 | 1H NMR (300 MHz, DMSO-d6) δ 11.87 (s, 1H), 10.99 (s, 1H), 9.29 (s, 1H), 8.86 (s, 1H), 7.85 (d, J = 8.1 Hz, 1H), 7.56 (d, J = 7.6 Hz, 1H), 7.28 (t, J = 7.8 Hz, 1H), 4.63 (t, J = 5.4 Hz, 1H), 4.01-3.97 (m, 1H), 3.76-3.70 (m, 1H), 3.52-3.39 (m, 2H), 3.23 (s, 3H). |

Synthesis of 2-(3-bromo-2-(2-hydroxyethoxy)phenyl)-5-hydroxy-N-(isoxazol-4-yl)-1-methyl-6-oxo-1,6-dihydropyrimidine-4-carboxamide (Example 15)

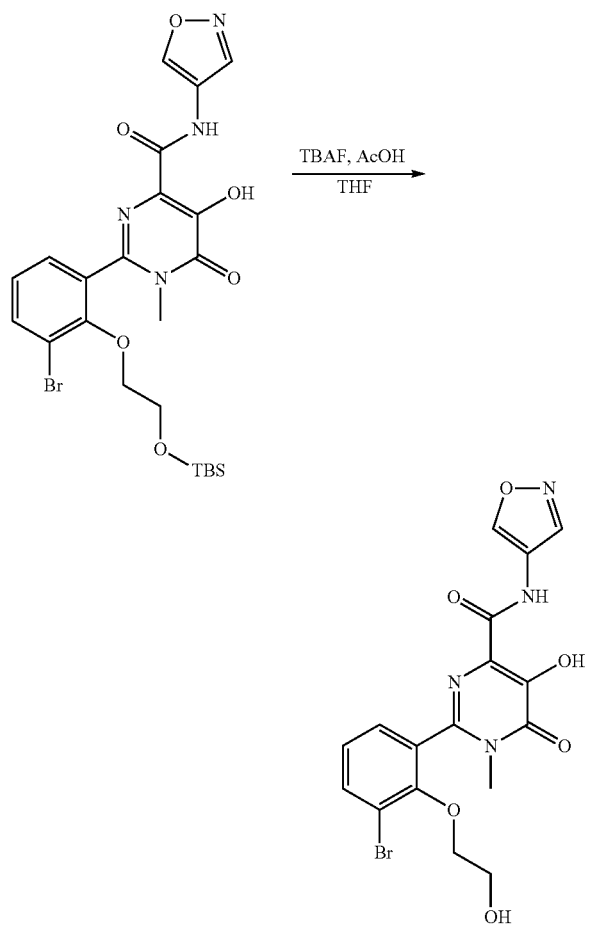

Into a 40 mL vial were added 2-(3-bromo-2-(2-((tert-butyldimethylsilyl)oxy) ethoxy)phenyl)-5-hydroxy-N-(isoxazol-4-yl)-1-methyl-6-oxo-1,6-dihydropyrimidine-4-carboxamide (300 mg, 0.531 mmol, 1.0 equiv) and THF (6.0 mL) at room temperature. To the above mixture was added TBAF (1M)/CH$_3$COOH=1:1 (1.20 mL, 2.0 equiv) drop wise over 2 min at 0° C. The resulting mixture was stirred for additional 5 h at room temperature. The resulting mixture was extracted with ethyl acetate (1×12 mL). The aqueous phase was further extracted with ethyl acetate (3×10 mL). The combined organic layers were washed with brine (2×7 mL), dried over anhydrous sodium sulfate. After filtration, the filtrate was concentrated under reduced pressure. The crude product (300 mg) was purified by Prep-HPLC (acetonitrile/formic acid/water) to afford 70 mg of 2-(3-bromo-2-(2-hydroxyethoxy)phenyl)-5-hydroxy-N-(isoxazol-4-yl)-1-methyl-6-oxo-1,6-dihydropyrimidine-4-carboxamide, 15, in 29% yield as a white solid. ESI-MS m/z=451.0 [M+H]$^+$. Calculated MW: 450.0. $^1$H NMR (300 MHz, DMSO-d6) δ 11.87 (s, 1H), 10.99 (s, 1H), 9.29 (s, 1H), 8.86 (s, 1H), 7.85 (d, J=8.1 Hz, 1H), 7.56 (d, J=7.6 Hz, 1H), 7.28 (t, J=7.8 Hz, 1H), 4.63 (t, J=5.4 Hz, 1H), 4.01-3.97 (m, 1H), 3.76-3.70 (m, 1H), 3.52-3.39 (m, 2H), 3.23 (s, 3H).

The following examples and intermediates were synthesized using similar conditions as those described in the step, above, along with appropriate starting materials.

TABLE 6

| Example | Structure | Name | LCMS |
|---|---|---|---|
| 16 | 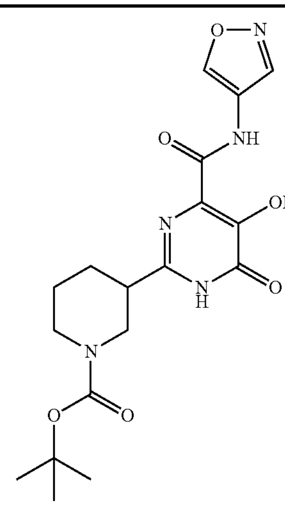 | tert-butyl 3-(5-hydroxy-4-(isoxazol-4-ylcarbamoyl)-6-oxo-1,6-dihydropyrimidin-2-yl)piperidine-1-carboxylate | ESI-MS m/z = 406.3 [M + H]+. Calculated MW: 405.4 |

TABLE 6-continued

| Example | Structure | Name | LCMS |
|---|---|---|---|
| 17 | 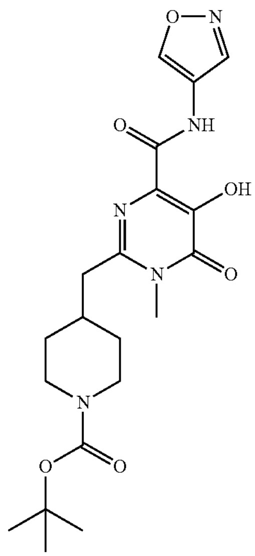 [SMILES: Cn1c(CC2CCN(C(=O)OC(C)(C)C)CC2)nc(C(=O)Nc2cnoc2)c(O)c1=O] | tert-butyl 4-((5-hydroxy-4-(isoxazol-4-ylcarbamoyl)-1-methyl-6-oxo-1,6-dihydropyrimidin-2-yl)methyl)piperidine-1-carboxylate | ESI-MS m/z = 434.4 [M + H]+. Calculated MW: 433.2 |
| 18 | 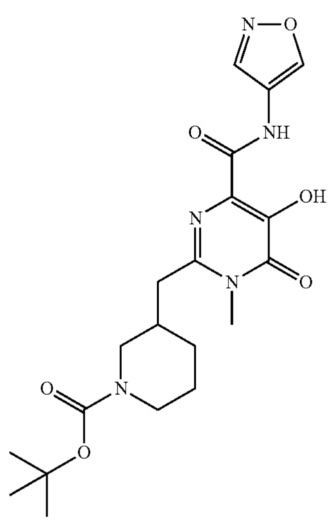 [SMILES: Cn1c(CC2CCCN(C(=O)OC(C)(C)C)C2)nc(C(=O)Nc2cnoc2)c(O)c1=O] | tert-butyl 3-((5-hydroxy-4-(isoxazol-4-ylcarbamoyl)-1-methyl-6-oxo-1,6-dihydropyrimidin-2-yl)methyl)piperidine-1-carboxylate | ESI-MS m/z = 434.2 [M + H]+. Calculated MW: 433.2 |
| 19 | 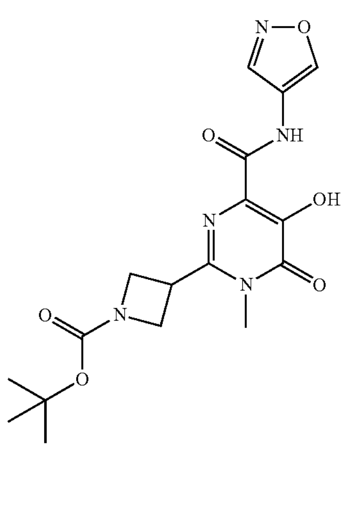 [SMILES: Cn1c(C2CN(C(=O)OC(C)(C)C)C2)nc(C(=O)Nc2cnoc2)c(O)c1=O] | tert-butyl 3-(5-hydroxy-4-(isoxazol-4-ylcarbamoyl)-1-methyl-6-oxo-1,6-dihydropyrimidin-2-yl)azetidine-1-carboxylate | ESI-MS m/z = 390.2 [M − H]−. Calculated MW: 391.2 |

TABLE 6-continued

| Example | Structure | Name | LCMS |
|---|---|---|---|
| 20 | 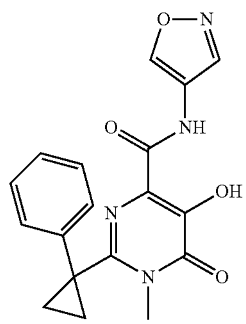 [SMILES: Cn1c(C2(c3ccccc3)CC2)nc(C(=O)Nc2cnoc2)c(O)c1=O] | 5-hydroxy-N-(isoxazol-4-yl)-1-methyl-6-oxo-2-(1-phenylcyclopropyl)-1,6-dihydropyrimidine-4-carboxamide | ESI-MS m/z = 353.2 [M + H]+. Calculated MW: 352.1 |
| 21 | 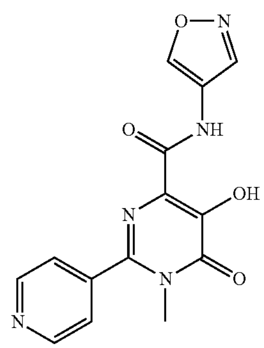 [SMILES: Cn1c(-c2ccncc2)nc(C(=O)Nc2cnoc2)c(O)c1=O] | 5-hydroxy-N-(isoxazol-4-yl)-1-methyl-6-oxo-2-(pyridin-4-yl)-1,6-dihydropyrimidine-4-carboxamide | ESI-MS m/z = 314.5 [M + H]+. Calculated MW: 313.3 |
| 22 | 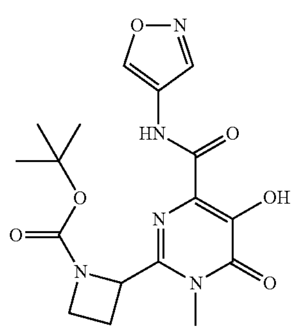 [SMILES: Cn1c(C2CCN2C(=O)OC(C)(C)C)nc(C(=O)Nc2cnoc2)c(O)c1=O] | tert-butyl 2-(5-hydroxy-4-(isoxazol-4-ylcarbamoyl)-1-methyl-6-oxo-1,6-dihydropyrimidin-2-yl)azetidine-1-carboxylate | ESI-MS m/z = 392.2 [M + H]+. Calculated MW: 391.1 |
| 23 | 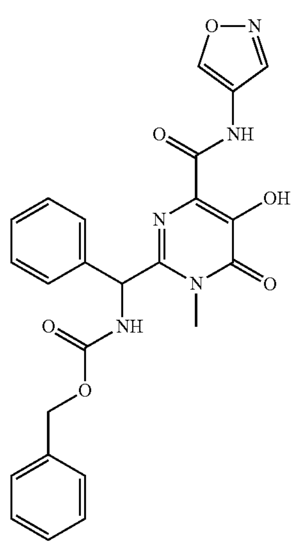 [SMILES: Cn1c(C(NC(=O)OCc2ccccc2)c2ccccc2)nc(C(=O)Nc2cnoc2)c(O)c1=O] | benzyl ((5-hydroxy-4-(isoxazol-4-ylcarbamoyl)-1-methyl-6-oxo-1,6-dihydropyrimidin-2-yl)(phenyl)methyl)carbamate | ESI-MS m/z = 476.3 [M + H]+. Calculated MW: 475.5 |

TABLE 6-continued

| Example | Structure | Name | LCMS |
|---|---|---|---|
| 24 | 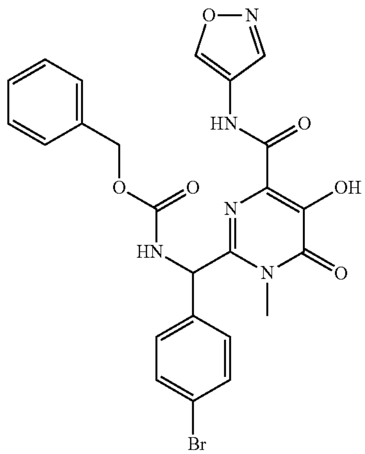 [SMILES: Cn1c(C(NC(=O)OCc2ccccc2)c2ccc(Br)cc2)nc(C(=O)Nc2cnoc2)c(O)c1=O] | benzyl ((4-bromophenyl)(5-hydroxy-4-(isoxazol-4-ylcarbamoyl)-1-methyl-6-oxo-1,6-dihydropyrimidin-2-yl)methyl)carbamate | ESI-MS m/z = 555.1 [M + H]+. Calculated MW: 554.4 |
| 25 | 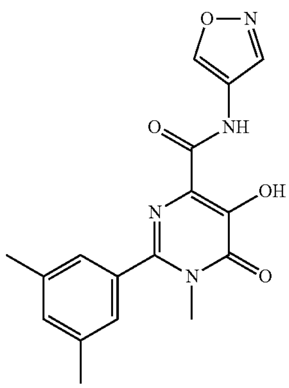 [SMILES: Cc1cc(C)cc(-c2nc(C(=O)Nc3cnoc3)c(O)c(=O)n2C)c1] | 2-(3,5-dimethylphenyl)-5-hydroxy-N-(isoxazol-4-yl)-1-methyl-6-oxo-1,6-dihydropyrimidine-4-carboxamide | ESI-MS m/z = 341.1 [M + H]+. Calculated MW: 340.1 |
| 26 | 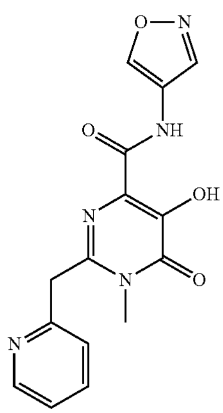 [SMILES: Cn1c(Cc2ccccn2)nc(C(=O)Nc2cnoc2)c(O)c1=O] | 5-hydroxy-N-(isoxazol-4-yl)-1-methyl-6-oxo-2-(pyridin-2-ylmethyl)-1,6-dihydropyrimidine-4-carboxamide | ESI-MS m/z = 328.2 [M + H]+. Calculated MW: 327.3 |
| 27 | 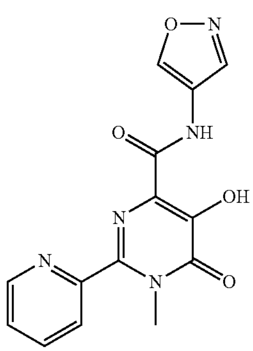 [SMILES: Cn1c(-c2ccccn2)nc(C(=O)Nc2cnoc2)c(O)c1=O] | 5-hydroxy-N-(isoxazol-4-yl)-1-methyl-6-oxo-2-(pyridin-2-yl)-1,6-dihydropyrimidine-4-carboxamide | ESI-MS m/z = 314.1 [M + H]+. Calculated MW: 313.3 |

TABLE 6-continued

| Example | Structure | Name | LCMS |
|---|---|---|---|
| 29 | 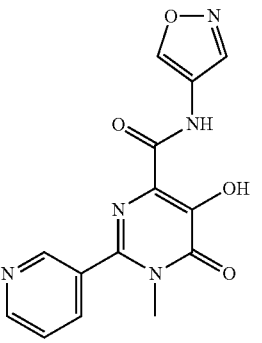 [SMILES: Cn1c(-c2cccnc2)nc(C(=O)Nc2cnoc2)c(O)c1=O] | 5-hydroxy-N-(isoxazol-4-yl)-1-methyl-6-oxo-2-(pyridin-3-yl)-1,6-dihydropyrimidine-4-carboxamide | ESI-MS m/z = 314.2 [M + H]+. Calculated MW: 313.3 |
| 30 | 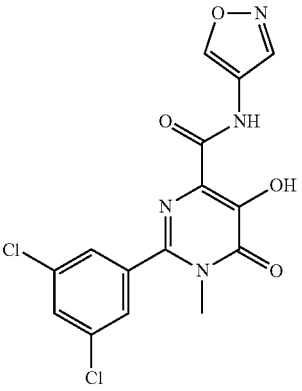 [SMILES: Cn1c(-c2cc(Cl)cc(Cl)c2)nc(C(=O)Nc2cnoc2)c(O)c1=O] | 2-(3,5-dichlorophenyl)-5-hydroxy-N-(isoxazol-4-yl)-1-methyl-6-oxo-1,6-dihydropyrimidine-4-carboxamide | ESI-MS m/z = 381.0 [M + H]+. Calculated MW: 380.0 |
| 31 | 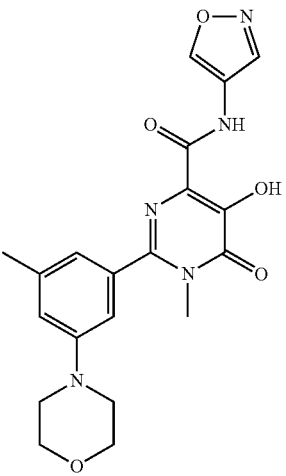 [SMILES: Cc1cc(-c2nc(C(=O)Nc3cnoc3)c(O)c(=O)n2C)cc(N2CCOCC2)c1] | 5-hydroxy-N-(isoxazol-4-yl)-1-methyl-2-(3-methyl-5-morpholinophenyl)-6-oxo-1,6-dihydropyrimidine-4-carboxamide | ESI-MS m/z = 412.2 [M + H]+. Calculated MW: 411.2 |

TABLE 6-continued

| Example | Structure | Name | LCMS |
|---|---|---|---|
| 32 | 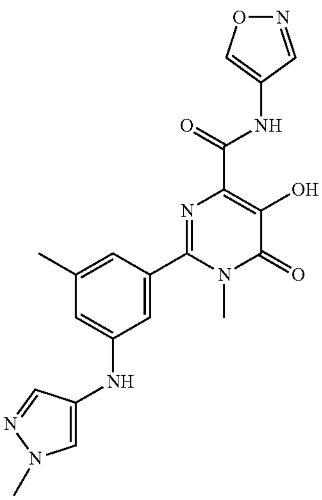 [SMILES: Cc1cc(Nc2cnn(C)c2)cc(-c2nc(C(=O)Nc3cnoc3)c(O)c(=O)n2C)c1] | 5-hydroxy-N-(isoxazol-4-yl)-1-methyl-2-(3-methyl-5-((1-methyl-1H-pyrazol-4-yl)amino)phenyl)-6-oxo-1,6-dihydropyrimidine-4-carboxamide | ESI-MS m/z = 422.2 [M + H]+. Calculated MW: 421.2 |
| 33 | 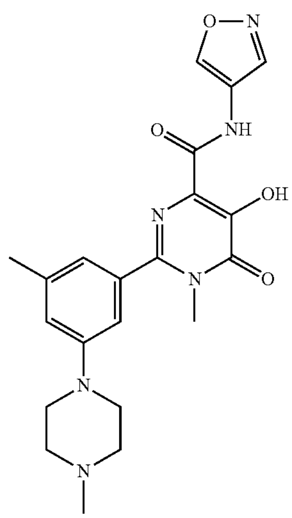 [SMILES: Cc1cc(-c2nc(C(=O)Nc3cnoc3)c(O)c(=O)n2C)cc(N2CCN(C)CC2)c1] | 5-hydroxy-N-(isoxazol-4-yl)-1-methyl-2-(3-methyl-5-(4-methylpiperazin-1-yl)phenyl)-6-oxo-1,6-dihydropyrimidine-4-carboxamide | ESI-MS m/z = 425.3 [M + H]+. Calculated MW: 424.2 |
| 34 | 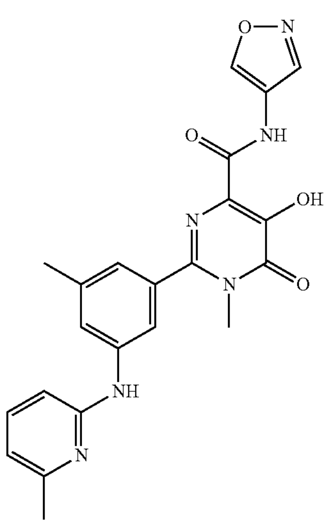 [SMILES: Cc1cc(Nc2cccc(C)n2)cc(-c2nc(C(=O)Nc3cnoc3)c(O)c(=O)n2C)c1] | 5-hydroxy-N-(isoxazol-4-yl)-1-methyl-2-(3-methyl-5-((6-methylpyridin-2-yl)amino)phenyl)-6-oxo-1,6-dihydropyrimidine-4-carboxamide | ESI-MS m/z = 433.2 [M + H]+. Calculated MW: 432.2 |

TABLE 6-continued

| Example | Structure | Name | LCMS |
|---|---|---|---|
| 35 | 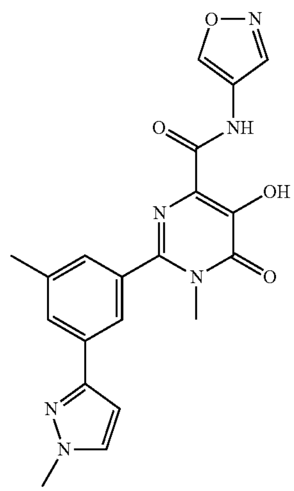 | 5-hydroxy-N-(isoxazol-4-yl)-1-methyl-2-(3-methyl-5-(1-methyl-1H-pyrazol-3-yl)phenyl)-6-oxo-1,6-dihydropyrimidine-4-carboxamide | ESI-MS m/z = 421.3 [M + H]+. Calculated MW: 420.2 |
| 36 | 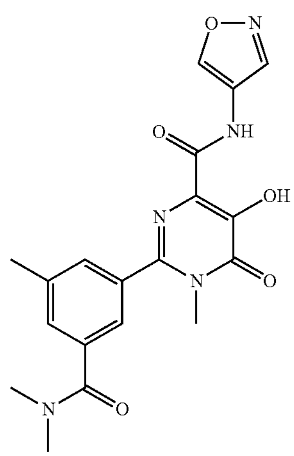 [SMILES: Cc1cc(C(=O)N(C)C)cc(-c2nc(C(=O)Nc3cnoc3)c(O)c(=O)n2C)c1] | 2-(3-(dimethylcarbamoyl)-5-methylphenyl)-5-hydroxy-N-(isoxazol-4-yl)-1-methyl-6-oxo-1,6-dihydropyrimidine-4-carboxamide | ESI-MS m/z = 398.2 [M + H]+. Calculated MW = 397.1 |
| 37 | 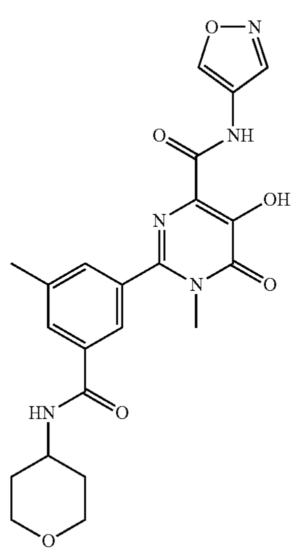 [SMILES: Cc1cc(C(=O)NC2CCOCC2)cc(-c2nc(C(=O)Nc3cnoc3)c(O)c(=O)n2C)c1] | 5-hydroxy-N-(isoxazol-4-yl)-1-methyl-2-(3-methyl-5-((tetrahydro-2H-pyran-4-yl)carbamoyl)phenyl)-6-oxo-1,6-dihydropyrimidine-4-carboxamide | ESI-MS m/z = 454.3 [M + H]+. Calculated MW: 453.2 |

TABLE 6-continued

| Example | Structure | Name | LCMS |
|---|---|---|---|
| 38 | 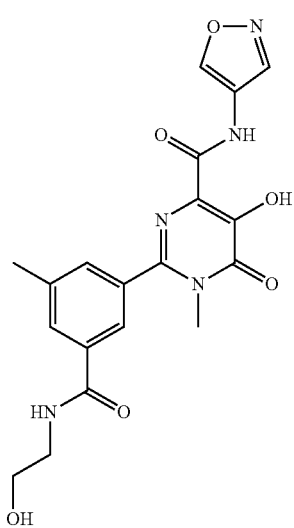 [SMILES: Cc1cc(C(=O)NCCO)cc(-c2nc(C(=O)Nc3cnoc3)c(O)c(=O)n2C)c1] | 5-hydroxy-2-(3-((2-hydroxyethyl)carbamoyl)-5-methylphenyl)-N-(isoxazol-4-yl)-1-methyl-6-oxo-1,6-dihydropyrimidine-4-carboxamide | ESI-MS m/z = 414.2 [M + H]+. Calculated MW = 413.1 |
| 39 | 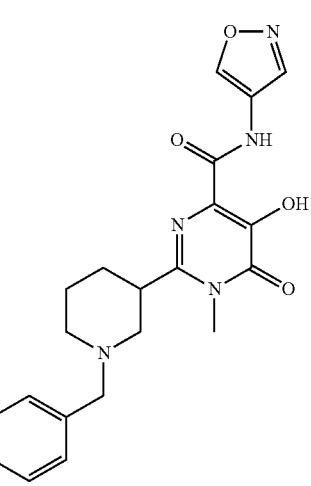 | 2-(1-benzylpiperidin-3-yl)-5-hydroxy-N-(isoxazol-4-yl)-1-methyl-6-oxo-1,6-dihydropyrimidine-4-carboxamide | ESI-MS m/z = 410.1 [M + H]+. Calculated MW: 409.5 |
| 40 | 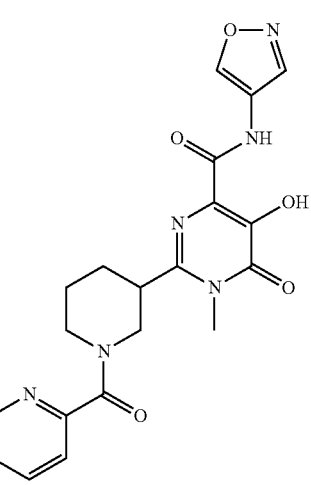 | 5-hydroxy-N-(isoxazol-4-yl)-1-methyl-6-oxo-2-(1-picolinoylpiperidin-3-yl)-1,6-dihydropyrimidine-4-carboxamide | ESI-MS m/z = 425.5 [M + H]+. Calculated MW: 424.4 |

TABLE 6-continued

| Example | Structure | Name | LCMS |
|---|---|---|---|
| 41 | 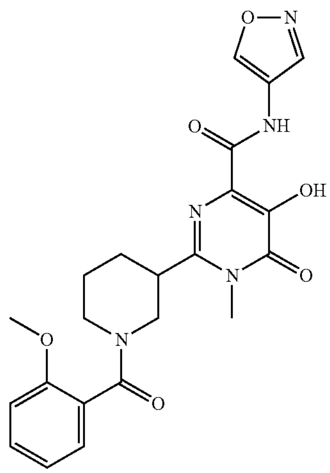 [SMILES: COc1ccccc1C(=O)N1CCCC(c2nc(C(=O)Nc3cnoc3)c(O)c(=O)n2C)C1] | 5-hydroxy-N-(isoxazol-4-yl)-2-(1-(2-methoxybenzoyl)piperidin-3-yl)-1-methyl-6-oxo-1,6-dihydropyrimidine-4-carboxamide | ESI-MS m/z = 454.1 [M + H]+. Calculated MW: 453.4 |
| 42 | 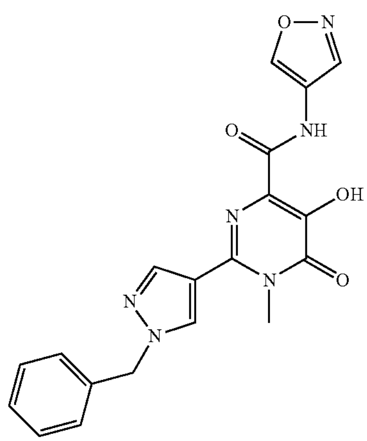 [SMILES: Cn1c(-c2cnn(Cc3ccccc3)c2)nc(C(=O)Nc2cnoc2)c(O)c1=O] | 2-(1-benzyl-1H-pyrazol-4-yl)-5-hydroxy-N-(isoxazol-4-yl)-1-methyl-6-oxo-1,6-dihydropyrimidine-4-carboxamide | ESI-MS m/z = 393.4 [M + H]+. Calculated MW: 392.4 |
| 43 | 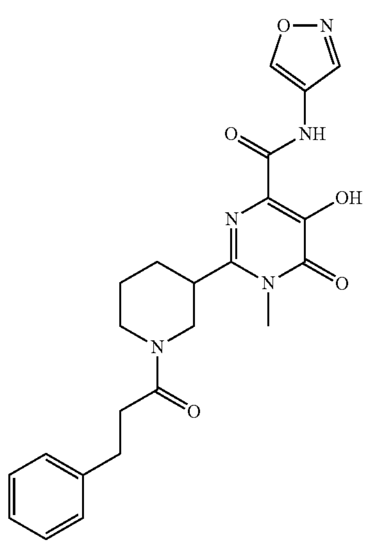 [SMILES: Cn1c(C2CCCN(C(=O)CCc3ccccc3)C2)nc(C(=O)Nc2cnoc2)c(O)c1=O] | 5-hydroxy-N-(isoxazol-4-yl)-1-methyl-6-oxo-2-(1-(3-phenylpropanoyl)piperidin-3-yl)-1,6-dihydropyrimidine-4-carboxamide | ESI-MS m/z = 452.7 [M + H]+. Calculated MW: 451.5 |

TABLE 6-continued

| Example | Structure | Name | LCMS |
|---|---|---|---|
| 44 | 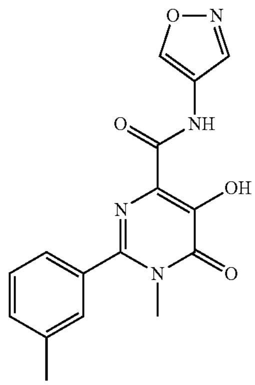 [SMILES: Cc1cccc(-c2nc(C(=O)Nc3cnoc3)c(O)c(=O)n2C)c1] | 5-hydroxy-N-(isoxazol-4-yl)-1-methyl-6-oxo-2-(m-tolyl)-1,6-dihydropyrimidine-4-carboxamide | ESI-MS m/z = 327.2 [M + H]+. Calculated MW: 326.3 |
| 45 | 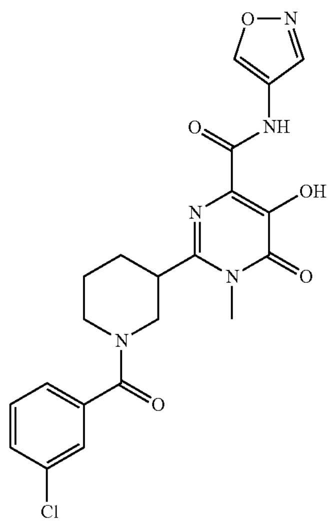 [SMILES: Cn1c(C2CCCN(C(=O)c3cccc(Cl)c3)C2)nc(C(=O)Nc2cnoc2)c(O)c1=O] | 2-(1-(3-chlorobenzoyl)piperidin-3-yl)-5-hydroxy-N-(isoxazol-4-yl)-1-methyl-6-oxo-1,6-dihydropyrimidine-4-carboxamide | ESI-MS m/z = 458.3 [M + H]+. Calculated MW: 457.9 |
| 46 | 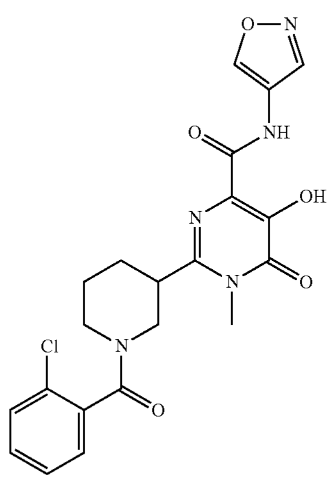 [SMILES: Cn1c(C2CCCN(C(=O)c3ccccc3Cl)C2)nc(C(=O)Nc2cnoc2)c(O)c1=O] | 2-(1-(2-chlorobenzoyl)piperidin-3-yl)-5-hydroxy-N-(isoxazol-4-yl)-1-methyl-6-oxo-1,6-dihydropyrimidine-4-carboxamide | ESI-MS m/z = 458.6 [M + H]+. Calculated MW: 457.9 |

TABLE 6-continued

| Example | Structure | Name | LCMS |
|---|---|---|---|
| 47 | 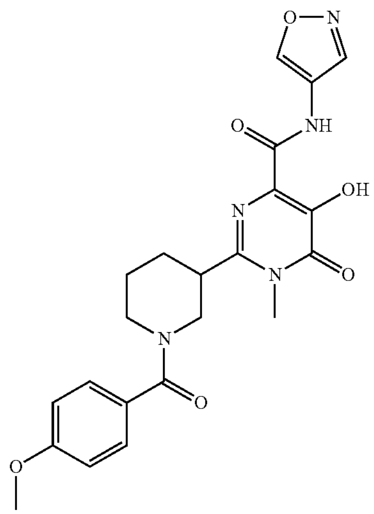 [SMILES: COc1ccc(C(=O)N2CCCC(c3nc(C(=O)Nc4cnoc4)c(O)c(=O)n3C)C2)cc1] | 5-hydroxy-N-(isoxazol-4-yl)-2-(1-(4-methoxybenzoyl)piperidin-3-yl)-1-methyl-6-oxo-1,6-dihydropyrimidine-4-carboxamide | ESI-MS m/z = 454.6 [M + H]+. Calculated MW: 453.4 |
| 48 | 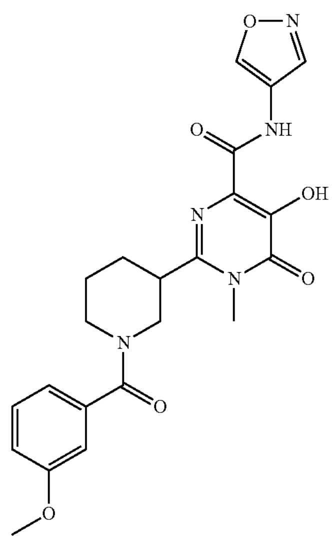 [SMILES: COc1cccc(C(=O)N2CCCC(c3nc(C(=O)Nc4cnoc4)c(O)c(=O)n3C)C2)c1] | 5-hydroxy-N-(isoxazol-4-yl)-2-(1-(3-methoxybenzoyl)piperidin-3-yl)-1-methyl-6-oxo-1,6-dihydropyrimidine-4-carboxamide | ESI-MS m/z = 454.6 [M + H]+. Calculated MW: 453.4 |
| 50 | 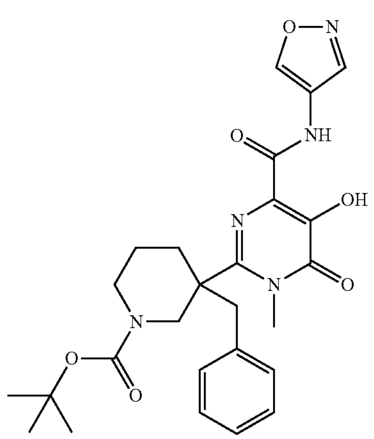 [SMILES: Cn1c(C2(Cc3ccccc3)CCCN(C(=O)OC(C)(C)C)C2)nc(C(=O)Nc2cnoc2)c(O)c1=O] | tert-butyl 3-benzyl-3-(5-hydroxy-4-(isoxazol-4-ylcarbamoyl)-1-methyl-6-oxo-1,6-dihydropyrimidin-2-yl)piperidine-1-carboxylate | ESI-MS m/z = 510.3 [M + H]+. Calculated MW: 509.2 |

TABLE 6-continued

| Example | Structure | Name | LCMS |
|---|---|---|---|
| 51 | 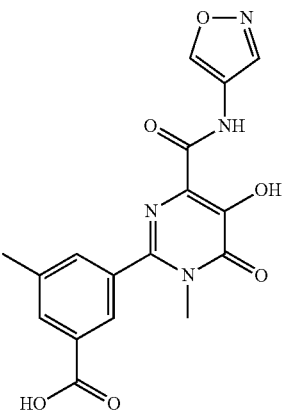 [SMILES: Cc1cc(C(=O)O)cc(-c2nc(C(=O)Nc3cnoc3)c(O)c(=O)n2C)c1] | 3-(5-hydroxy-4-(isoxazol-4-ylcarbamoyl)-1-methyl-6-oxo-1,6-dihydropyrimidin-2-yl)-5-methylbenzoic acid | ESI-MS m/z = 371.2 [M + H]+. Calculated MW: 370.1 |
| 52 | 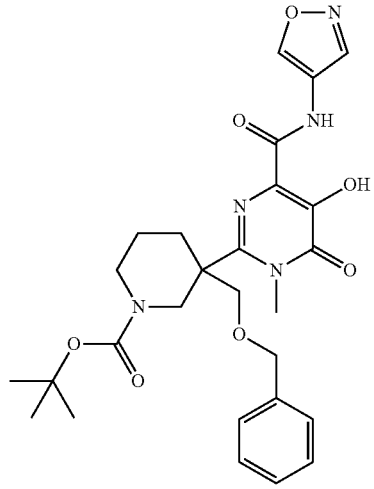 [SMILES: Cn1c(C2(COCc3ccccc3)CCCN(C(=O)OC(C)(C)C)C2)nc(C(=O)Nc2cnoc2)c(O)c1=O] | tert-butyl 3-((benzyloxy)methyl)-3-(5-hydroxy-4-(isoxazol-4-ylcarbamoyl)-1-methyl-6-oxo-1,6-dihydropyrimidin-2-yl)piperidine-1-carboxylate | ESI-MS m/z = 540.2 [M + H]+. Calculated MW: 539.2 |
| 53 | 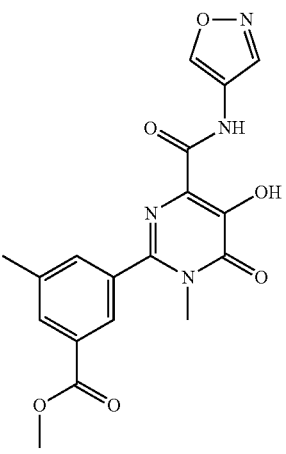 [SMILES: COC(=O)c1cc(C)cc(-c2nc(C(=O)Nc3cnoc3)c(O)c(=O)n2C)c1] | methyl 3-(5-hydroxy-4-(isoxazol-4-ylcarbamoyl)-1-methyl-6-oxo-1,6-dihydropyrimidin-2-yl)-5-methylbenzoate | ESI-MS m/z = 385.2 [M + H]+. Calculated MW: 384.1 |

TABLE 6-continued

| Example | Structure | Name | LCMS |
|---|---|---|---|
| 54 | 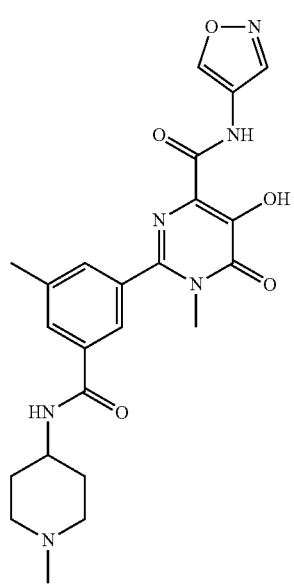 [SMILES: Cc1cc(C(=O)NC2CCN(C)CC2)cc(-c2nc(C(=O)Nc3cnoc3)c(O)c(=O)n2C)c1] | 5-hydroxy-N-(isoxazol-4-yl)-1-methyl-2-(3-methyl-5-((1-methylpiperidin-4-yl)carbamoyl)phenyl)-6-oxo-1,6-dihydropyrimidine-4-carboxamide | ESI-MS m/z = 467.2 [M + H]+. Calculated MW = 466.2 |
| 55 | 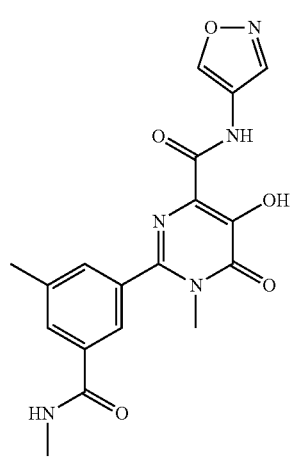 | 5-hydroxy-N-(isoxazol-4-yl)-1-methyl-2-(3-methyl-5-(methylcarbamoyl)phenyl)-6-oxo-1,6-dihydropyrimidine-4-carboxamide | ESI-MS m/z = 384.3 [M + H]+. Calculated MW = 383.1 |
| 56 | 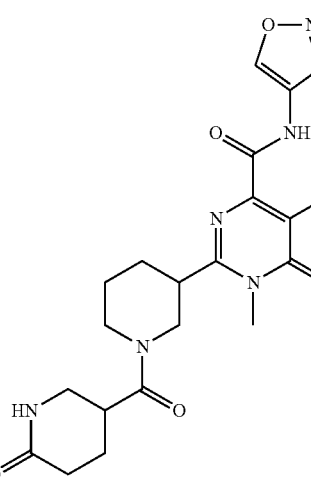 | 5-hydroxy-N-(isoxazol-4-yl)-1-methyl-6-oxo-2-(1-(6-oxopiperidine-3-carbonyl)piperidin-3-yl)-1,6-dihydropyrimidine-4-carboxamide | ESI-MS m/z = 445.3 [M + H]+. Calculated MW: 444.4 |

TABLE 6-continued

| Example | Structure | Name | LCMS |
|---------|-----------|------|------|
| 57 | 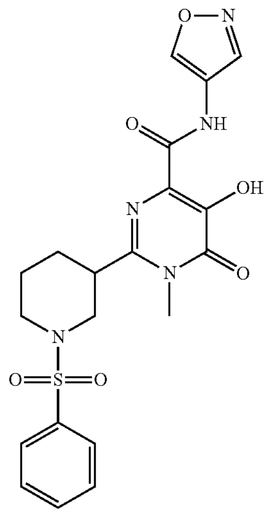 [SMILES: Cn1c(C2CCCN(S(=O)(=O)c3ccccc3)C2)nc(C(=O)Nc2cnoc2)c(O)c1=O] | 5-hydroxy-N-(isoxazol-4-yl)-1-methyl-6-oxo-2-(1-(phenylsulfonyl)piperidin-3-yl)-1,6-dihydropyrimidine-4-carboxamide | ESI-MS m/z = 460.2 [M + H]+. Calculated MW: 459.5 |
| 58 | 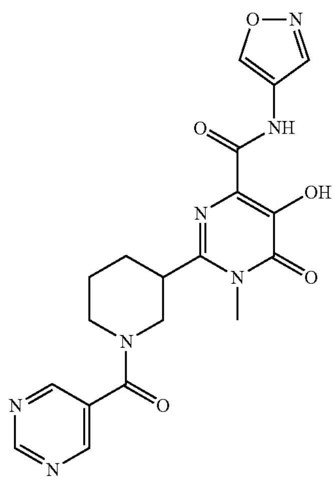 [SMILES: Cn1c(C2CCCN(C(=O)c3cncnc3)C2)nc(C(=O)Nc2cnoc2)c(O)c1=O] | 5-hydroxy-N-(isoxazol-4-yl)-1-methyl-6-oxo-2-(1-(pyrimidine-5-carbonyl)piperidin-3-yl)-1,6-dihydropyrimidine-4-carboxamide | ESI-MS m/z = 426.2 [M + H]+. Calculated MW: 425.4 |
| 59 | 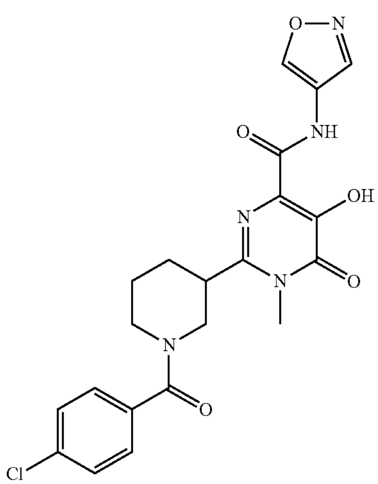 [SMILES: Cn1c(C2CCCN(C(=O)c3ccc(Cl)cc3)C2)nc(C(=O)Nc2cnoc2)c(O)c1=O] | 2-(1-(4-chlorobenzoyl)piperidin-3-yl)-5-hydroxy-N-(isoxazol-4-yl)-1-methyl-6-oxo-1,6-dihydropyrimidine-4-carboxamide | ESI-MS m/z = 458.2 [M + H]+. Calculated MW: 457.9 |

TABLE 6-continued

| Example | Structure | Name | LCMS |
|---|---|---|---|
| 60 | 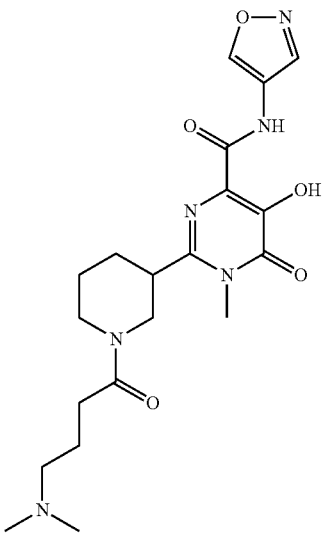 [SMILES: CN(C)CCCC(=O)N1CCCC(c2nc(C(=O)Nc3cnoc3)c(O)c(=O)n2C)C1] | 2-(1-(4-(dimethylamino)butanoyl)piperidin-3-yl)-5-hydroxy-N-(isoxazol-4-yl)-1-methyl-6-oxo-1,6-dihydropyrimidine-4-carboxamide | ESI-MS m/z = 433.3 [M + H]+. Calculated MW: 432.5 |
| 61 | 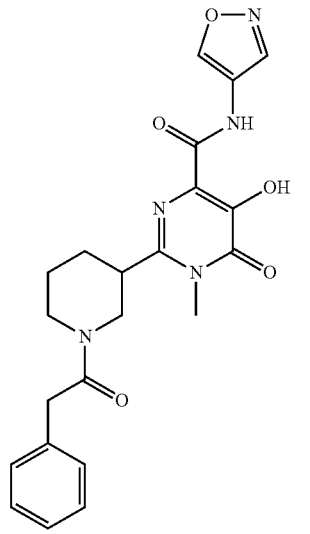 [SMILES: Cn1c(C2CCCN(C(=O)Cc3ccccc3)C2)nc(C(=O)Nc2cnoc2)c(O)c1=O] | 5-hydroxy-N-(isoxazol-4-yl)-1-methyl-6-oxo-2-(1-(2-phenylacetyl)piperidin-3-yl)-1,6-dihydropyrimidine-4-carboxamide | ESI-MS m/z = 438.3 [M + H]+. Calculated MW: 437.5 |
| 62 | 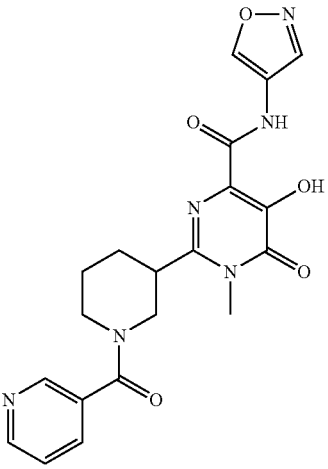 [SMILES: Cn1c(C2CCCN(C(=O)c3cccnc3)C2)nc(C(=O)Nc2cnoc2)c(O)c1=O] | 5-hydroxy-N-(isoxazol-4-yl)-1-methyl-2-(1-nicotinoylpiperidin-3-yl)-6-oxo-1,6-dihydropyrimidine-4-carboxamide | ESI-MS m/z = 425.3 [M + H]+. Calculated MW: 424.4 |

TABLE 6-continued

| Example | Structure | Name | LCMS |
|---|---|---|---|
| 63 | 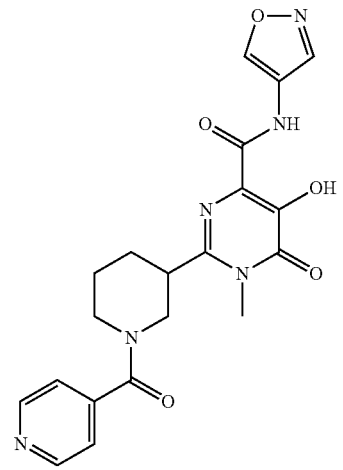 [SMILES: Cn1c(C2CCCN(C(=O)c3ccncc3)C2)nc(C(=O)Nc2cnoc2)c(O)c1=O] | 5-hydroxy-2-(1-isonicotinoylpiperidin-3-yl)-N-(isoxazol-4-yl)-1-methyl-6-oxo-1,6-dihydropyrimidine-4-carboxamide | ESI-MS m/z = 425.3 [M + H]+. Calculated MW: 424.4 |
| 64 | 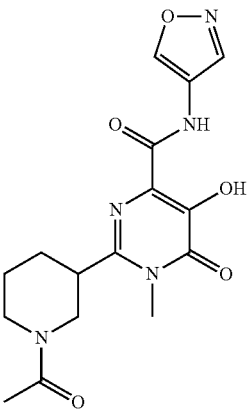 [SMILES: CC(=O)N1CCCC(c2nc(C(=O)Nc3cnoc3)c(O)c(=O)n2C)C1] | 2-(1-acetylpiperidin-3-yl)-5-hydroxy-N-(isoxazol-4-yl)-1-methyl-6-oxo-1,6-dihydropyrimidine-4-carboxamide | ESI-MS m/z = 362.2 [M + H]+. Calculated MW: 361.4 |
| 65 | 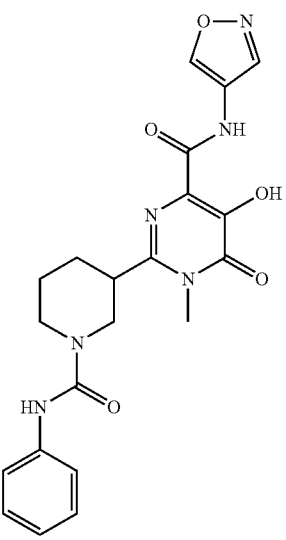 [SMILES: Cn1c(C2CCCN(C(=O)Nc3ccccc3)C2)nc(C(=O)Nc2cnoc2)c(O)c1=O] | 5-hydroxy-N-(isoxazol-4-yl)-1-methyl-6-oxo-2-(1-(phenylcarbamoyl)piperidin-3-yl)-1,6-dihydropyrimidine-4-carboxamide | ESI-MS m/z = 439.2 [M + H]+. Calculated MW: 438.4 |

TABLE 6-continued

| Example | Structure | Name | LCMS |
|---|---|---|---|
| 66 | 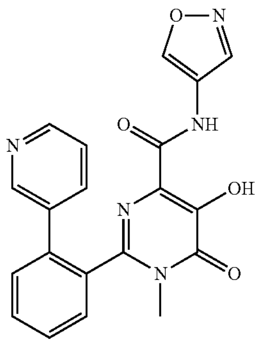 [SMILES: Cn1c(-c2ccccc2-c2cccnc2)nc(C(=O)Nc2cnoc2)c(O)c1=O] | 5-hydroxy-N-(isoxazol-4-yl)-1-methyl-6-oxo-2-(2-(pyridin-3-yl)phenyl)-1,6-dihydropyrimidine-4-carboxamide | ESI-MS m/z = 390.5 [M + H]+. Calculated MW: 389.4 |
| 67 | 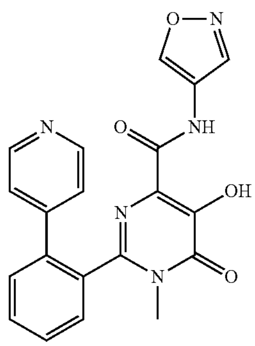 [SMILES: Cn1c(-c2ccccc2-c2ccncc2)nc(C(=O)Nc2cnoc2)c(O)c1=O] | 5-hydroxy-N-(isoxazol-4-yl)-1-methyl-6-oxo-2-(2-(pyridin-4-yl)phenyl)-1,6-dihydropyrimidine-4-carboxamide | ESI-MS m/z = 390.3 [M + H]+. Calculated MW: 389.4 |
| 68-69 | Intentionally Omitted | | |
| 70 | 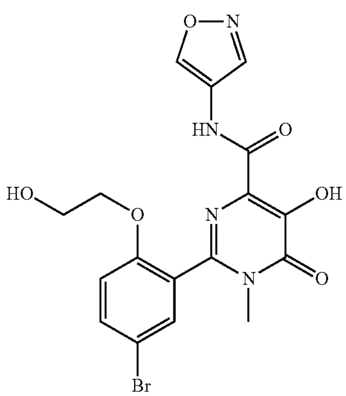 [SMILES: Cn1c(-c2cc(Br)ccc2OCCO)nc(C(=O)Nc2cnoc2)c(O)c1=O] | 2-(5-bromo-2-(2-hydroxyethoxy)phenyl)-5-hydroxy-N-(isoxazol-4-yl)-1-methyl-6-oxo-1,6-dihydropyrimidine-4-carboxamide | ESI-MS m/z = 451.1 [M + H]+. Calculated MW: 450.2 |
| 70-71 | Intentionally Omitted | | |
| 73 | 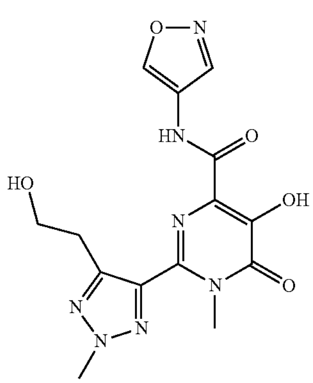 [SMILES: Cn1nc(CCO)c(-c2nc(C(=O)Nc3cnoc3)c(O)c(=O)n2C)n1] | 5-hydroxy-2-(5-(2-hydroxyethyl)-2-methyl-2H-1,2,3-triazol-4-yl)-N-(isoxazol-4-yl)-1-methyl-6-oxo-1,6-dihydropyrimidine-4-carboxamide | ESI-MS m/z = 362.2 [M + H]+. Calculated MW: 361.4 |

TABLE 6-continued

| Example | Structure | Name | LCMS |
|---|---|---|---|
| 74 | 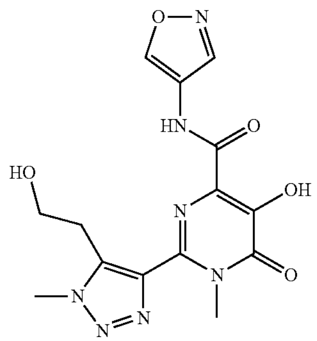 [SMILES: Cn1nnc(-c2nc(C(=O)Nc3cnoc3)c(O)c(=O)n2C)c1CCO] | 5-hydroxy-2-(5-(2-hydroxyethyl)-1-methyl-1H-1,2,3-triazol-4-yl)-N-(isoxazol-4-yl)-1-methyl-6-oxo-1,6-dihydropyrimidine-4-carboxamide | ESI-MS m/z = 362.2 [M + H]+. Calculated MW: 361.4 |
| 75 | 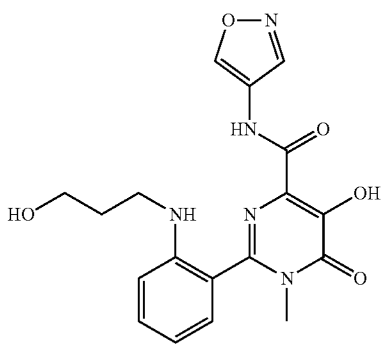 [SMILES: Cn1c(-c2ccccc2NCCCO)nc(C(=O)Nc2cnoc2)c(O)c1=O] | 5-hydroxy-2-(2-((3-hydroxypropyl)amino)phenyl)-N-(isoxazol-4-yl)-1-methyl-6-oxo-1,6-dihydropyrimidine-4-carboxamide | ESI-MS m/z = 386.2 [M + H]+. Calculated MW: 385.4 |
| 76 | 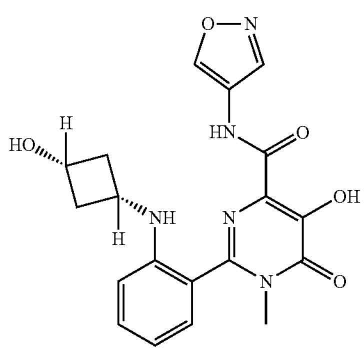 [SMILES: Cn1c(-c2ccccc2N[C@H]2C[C@@H](O)C2)nc(C(=O)Nc2cnoc2)c(O)c1=O] | 5-hydroxy-2-(2-(((1s,3s)-3-hydroxycyclobutyl)amino)phenyl)-N-(isoxazol-4-yl)-1-methyl-6-oxo-1,6-dihydropyrimidine-4-carboxamide | ESI-MS m/z = 398.2 [M + H]+. Calculated MW: 397.4 |
| 77 | Intentionally Omitted | | |
| 78 | 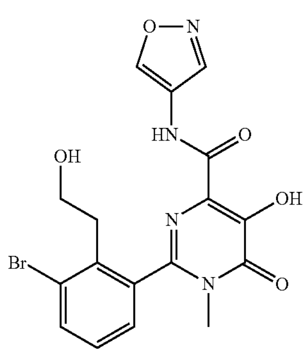 [SMILES: Cn1c(-c2cccc(Br)c2CCO)nc(C(=O)Nc2cnoc2)c(O)c1=O] | 2-(3-bromo-2-(2-hydroxyethyl)phenyl)-5-hydroxy-N-(isoxazol-4-yl)-1-methyl-6-oxo-1,6-dihydropyrimidine-4-carboxamide | ESI-MS m/z = 437.05 [M + H]+. Calculated MW: 436.2 |

TABLE 6-continued

| Example | Structure | Name | LCMS |
|---|---|---|---|
| 79 | 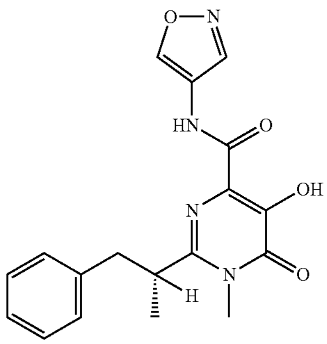 [SMILES: C[C@H](Cc1ccccc1)c1nc(C(=O)Nc2cnoc2)c(O)c(=O)n1C] | (R)-5-hydroxy-N-(isoxazol-4-yl)-1-methyl-6-oxo-2-(1-phenylpropan-2-yl)-1,6-dihydropyrimidine-4-carboxamide | ESI-MS m/z = 355.2 [M + H]+. Calculated MW: 354.4 |
| 80 | 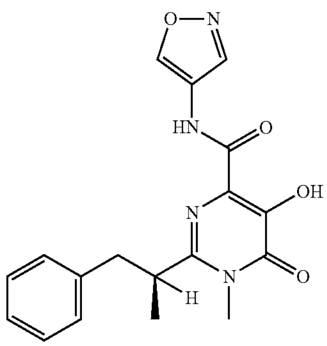 [SMILES: C[C@@H](Cc1ccccc1)c1nc(C(=O)Nc2cnoc2)c(O)c(=O)n1C] | (S)-5-hydroxy-N-(isoxazol-4-yl)-1-methyl-6-oxo-2-(1-phenylpropan-2-yl)-1,6-dihydropyrimidine-4-carboxamide | ESI-MS m/z = 355.2 [M + H]+. Calculated MW: 354.4 |
| 81 | Intentionally Omitted | | |
| 104 | 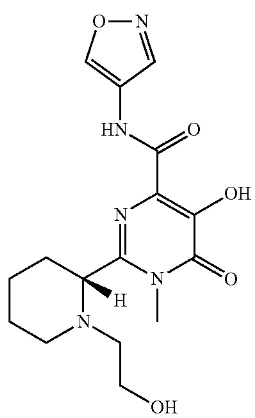 [SMILES: Cn1c([C@H]2CCCCN2CCO)nc(C(=O)Nc2cnoc2)c(O)c1=O] | (R)-5-hydroxy-2-(1-(2-hydroxyethyl)piperidin-2-yl)-N-(isoxazol-4-yl)-1-methyl-6-oxo-1,6-dihydropyrimidine-4-carboxamide | ESI-MS m/z = 364.3 [M + H]+. Calculated MW: 363.4 |

Synthesis of tert-butyl-3-(5-ethoxy-4-(isoxazol-4-ylcarbamoyl)-1-methyl-6-oxo-1,6-dihydropyrimidin-2-yl)piperidine-1-carboxylate (Isomer A1)

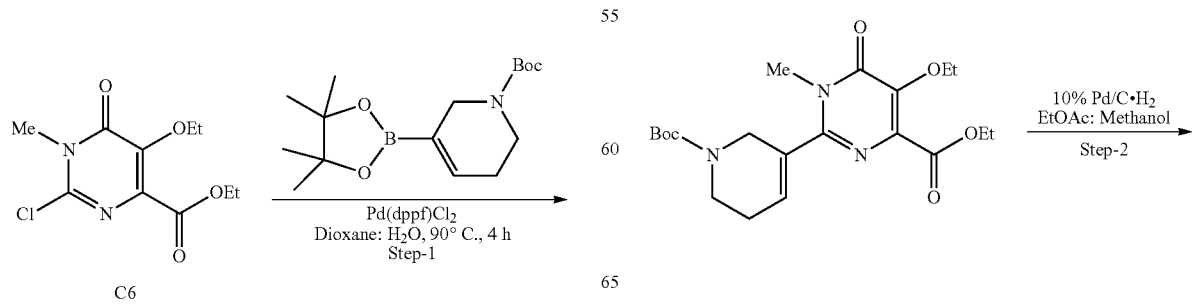

-continued

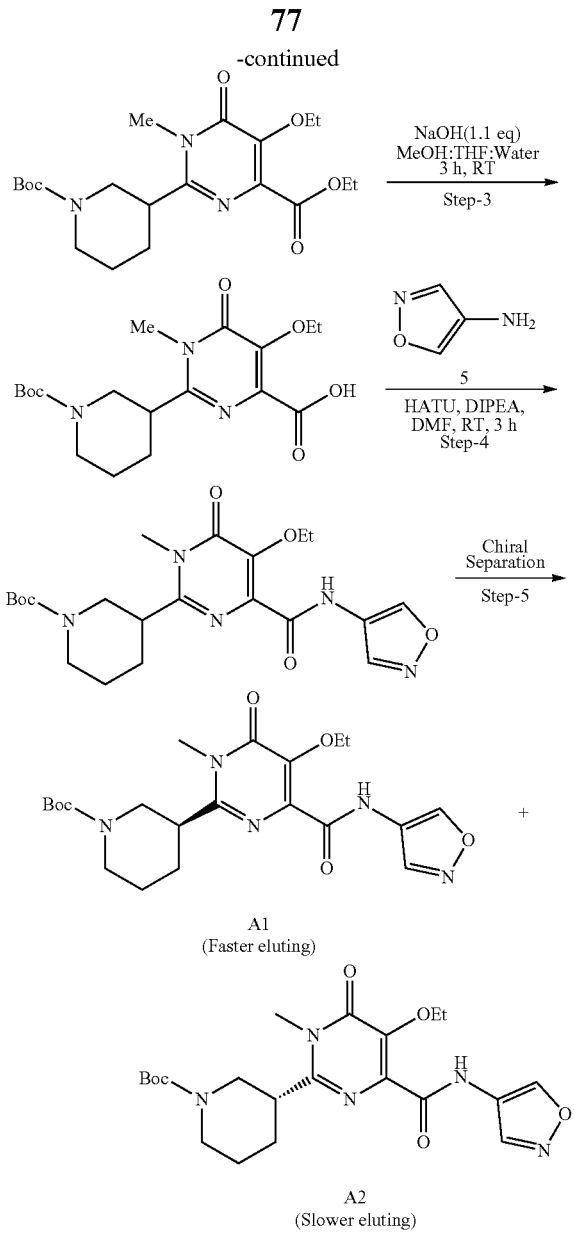

A1 (Faster eluting)

A2 (Slower eluting)

Step-1: Ethyl 2-(1-(tert-butoxycarbonyl)-1,2,5,6-tetrahydropyridin-3-yl)-5-ethoxy-1-methyl-6-oxo-1,6-dihydropyrimidine-4-carboxylate A mixture of Ethyl 2-chloro-5-ethoxy-1-methyl-6-oxo-1,6-dihydropyrimidine-4-carboxylate (2 g, 7.67 mmol), tert-butyl 5-(4,4,5,5-tetramethyl-1,3,2-dioxaborolan-2-yl)-3,6-dihydropyridine-1(2H)-carboxylate (2.96 g, 9.59 mmol) and sodium carbonate (1.62 g, 15.34 mmol) in a solution of dioxane/water (4:1, 50 mL) was degassed for 20 minutes with Argon gas. PdCl$_2$(dppf) (0.561 g, 0.76 mmol) was added and degassing was continued for another 10 minutes. The reaction mixture was heated at 90° C. for 4 h. After completion of reaction, the reaction mixture was taken up in water (100 mL) and extracted with ethyl acetate (2×50 mL). The combined organic layer was washed with brine (30 mL), dried over anhydrous Na$_2$SO$_4$ and concentrated under reduced pressure. The crude product was purified by column chromatography to obtain title compound (2.57 g, 82%) as a solid. LCMS: calc'd 408.3; ESI-MS m/z=408.61 [M+H]$^+$ $_1$H NMR (400 MHz, DMSO-d$_6$): δ 1.23-1.31 (m, 6H), 1.43 (s, 9H), 2.25-2.40 (m, 2H), 3.44 (s, 3H), 3.45-3.50 (m, 2H), 4.05-4.10 (m, 2H), 4.16 (q, J=7.2 Hz, 2H), 4.31 (q, J=7.2 Hz, 2H), 6.26 (bs, 1H).

Step-2: Ethyl-2-(1-(tert-butoxycarbonyl)piperidin-3-yl)-5-ethoxy-1-methyl-6-oxo-1,6-dihydropyrimidine-4-carboxylate To a mixture of ethyl 2-(1-(tert-butoxycarbonyl)-1,2,5,6-tetrahydropyridin-3-yl)-5-ethoxy-1-methyl-6-oxo-1,6-dihydropyrimidine-4-carboxylate (2.57 g, 6.30 mmol) is dissolved and stirred in a solution of methanol:ethyl acetate (1:3, 54 mL) was added 10% Pd/C (0.67 g, with 50% moisture). The reaction was stirred at room temperature under Hydrogen gas atmosphere for 3.5 h. After completion of reaction, the reaction mixture was filtered through celite bed and washed with ethyl acetate (2×50 mL). The filtrate was concentrated under reduced pressure. The obtained crude product was purified by column chromatography to give title compound (2.35 g, 91%). LCMS: calc'd 409.3, ESI-MS m/z=410.4 [M+H]$^+$

Step-3: 2-(1-(tert-butoxycarbonyl)piperidin-3-yl)-5-ethoxy-1-methyl-6-oxo-1,6-dihydropyrimidine-4-carboxylic acid To a stirred solution of Ethyl-2-(1-(tert-butoxycarbonyl)piperidin-3-yl)-5-ethoxy-1-methyl-6-oxo-1,6-dihydropyrimidine-4-carboxylate (1.9 g, 4.64 mmol) in a mixture of methanol:THF:H$_2$O (1:1:1, 30 mL) was added NaOH (0.222 g, 5.56 mmol) at room temperature. The resulting reaction mixture was stirred at room temperature for 3 h. After completion of reaction, the reaction concentrated under vacuum. The reaction mixture was dissolved in water (10 mL) and acidified with 1N HCl (pH-6). The product was extracted with 10% methanol in dichloromethane (2×30 mL). Combined organic layer was washed with brine (30 mL) and evaporated under vacuum to get crude title compound (1.67 g, 94%) which was used in the next step without further purification. LCMS: calc'd 381.3; ESI-MS m/z=382.5 [M+H]$^+$

Step-4: tert-butyl-3-(5-ethoxy-4-(isoxazol-4-ylcarbamoyl)-1-methyl-6-oxo-1,6-dihydropyrimidin-2-yl)piperidine-1-carboxylate To a stirred solution of 2-(1-(tert-butoxycarbonyl)piperidin-3-yl)-5-ethoxy-1-methyl-6-oxo-1,6-dihydropyrimidine-4-carboxylic acid (1.67 g, 4.37 mmol) in dry DMF (16 mL) was added HATU (2.49 g, 6.56 mmol) at 0° C. Reaction mixture was stirred at room temperature for 1 h. Then isoxazol-4-amine (0.441 g, 5.25 mmol) in DMF (0.5 mL) and DIPEA (1.5 mL, 8.75 mmol) were added at room temperature and the reaction mixture was stirred for 3 h. After completion of reaction, the reaction mixture was diluted with water (20 mL) and extracted with ethyl acetate (2×30 mL). The combined organic layer was dried over anhydrous Na$_2$SO$_4$ and concentrated under reduced pressure. The crude product was purified by Combiflash column chromatography to give the title compound (1.67 g, 85%) as a racemic mixture. Chiral resolution of racemic pure compound (1.2 g) was performed by using chiral preparative HPLC to give 500 mg of each of enantiomer. LCMS: Calc'd 447.3; ESI-MS m/z=448.60 [M+H]$^+$ Chiral HPLC: CHIRALPAK AD-H; 30% methanol in Liquid CO$_2$+0.1% DEA.

FR-1 (Isomer-A1): R$_T$=7.66 min; FR-2 (Isomer-A2): R$_T$=8.81 min; A1: $^1$H NMR (400 MHz, DMSO-d6): δ 1.21-1.25 (m, 3H), 1.41 (s, 9H), 1.46-1.57 (m, 2H), 1.71-1.74 (m, 2H), 2.02-2.04 (m, 1H), 2.76-2.98 (m, 2H), 2.99-3.15 (m, 1H), 3.57 (s, 3H), 3.85-4.15 (m, 1H), 4.10-4.15 (m, 2H), 8.78 (s, 1H), 9.29 (s, 1H), 10.56 (s, 1H). A2: $^1$H NMR (400 MHz, DMSO-d6): δ 1.21-1.29 (m, 3H), 1.41 (s, 9H), 1.46-1.57 (m, 2H), 1.71-1.74 (m, 2H), 2.02-2.04 (m, 1H), 2.78-2.98 (m, 2H), 2.99-3.15 (m, 1H), 3.57 (s, 3H), 3.85-4.15 (m, 1H), 4.10-4.15 (m, 2H), 8.78 (s, 1H), 9.29 (s, 1H), 10.57 (s, 1H).

Synthesis of 1-((2-((R)-1-(3,4-dichlorobenzoyl)piperidin-3-yl)-4-(isoxazol-4-ylcarbamoyl)-1-methyl-6-oxo-1,6-dihydropyrimidin-5-yl)oxy)ethyl ethyl carbonate (Example 131)

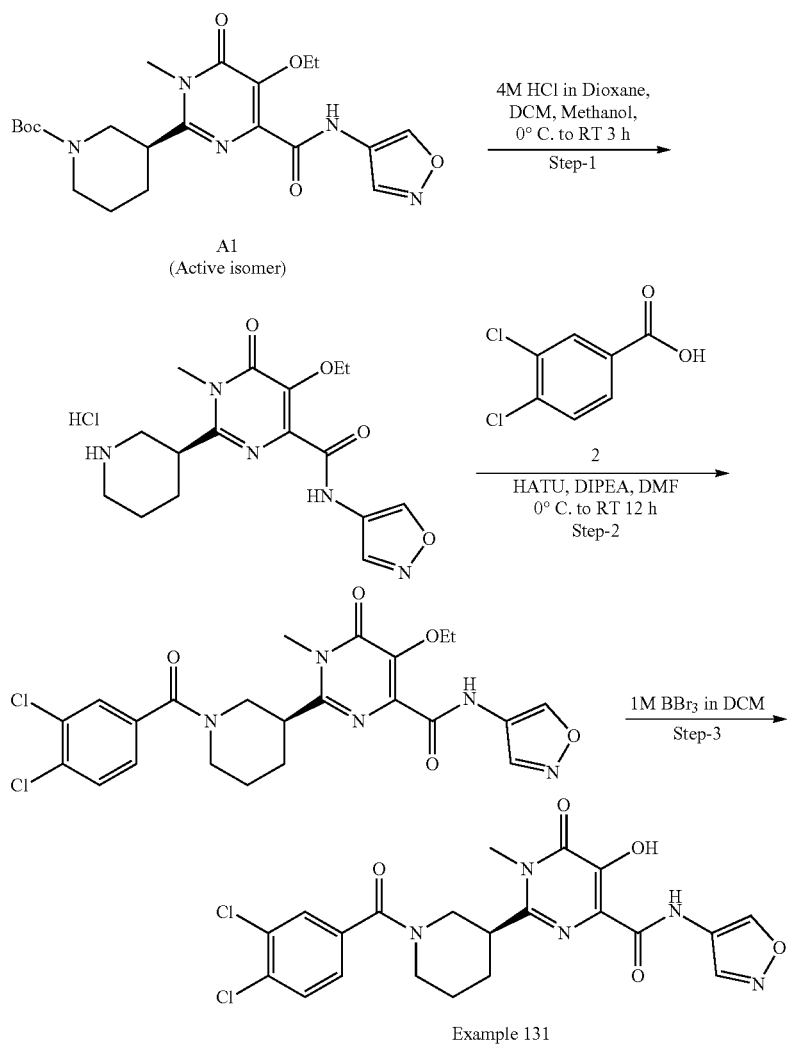

Example 131

Step-1: (R)-5-ethoxy-N-(isoxazol-4-yl)-1-methyl-6-oxo-2-(piperidin-3-yl)-1,6-dihydropyrimidine-4-carboxamide hydrochloride salt To a stirred solution of tert-butyl (R)-3-(5-ethoxy-4-(isoxazol-4-ylcarbamoyl)-1-methyl-6-oxo-1,6-dihydropyrimidin-2-yl)piperidine-1-carboxylate (0.20 g, 0.44 mmol) in mixture of dichloromethane (1.32 mL) and methanol (0.66 mL) was added 4M HCl in dioxane (1 mL) dropwise at 0° C. The reaction mixture was stirred at room temperature for 1 h and warmed to 40° C. for 10 min. The reaction mixture was concentrated to dryness and azeotroped twice with methanol to afford the title compound (0.17 g, 99%) as a solid, which was used in the next step without further purification. LCMS: calc'd 347.3, ESI-MS m/z=348.48 [M+H]$^+$

Step-2: (R)-2-(1-(3,4-dichlorobenzoyl)piperidin-3-yl)-5-ethoxy-N-(isoxazol-4-yl)-1-methyl-6-oxo-1,6-dihydropyrimidine-4-carboxamide To a stirred solution of 3,4-dichlorobenzoic acid (0.101 g, 0.53 mmol) in dry DMF (1.7 ml) was added HATU (0.252 g, 0.66 mmol) at 0° C. Reaction mixture was stirred at room temperature for 1 h. Then (R)-5-ethoxy-N-(isoxazol-4-yl)-1-methyl-6-oxo-2-(piperidin-3-yl)-1,6-dihydropyrimidine-4-carboxamide hydrochloride salt (0.170 g, 0.44 mmol) and DIPEA (0.25 mL, 1.33 mmol) were added at room temperature and reaction mixture was stirred for 3 h. Upon completion the reaction was diluted with water (15 mL) and extracted with ethyl acetate (2×20 mL). The combined organic layer was washed with cold saturated sodium bicarbonate (20 mL), dried over anhydrous $Na_2SO_4$ and concentrated under reduced pressure. The crude product was purified by column chromatography to give a title compound (0.21 g, 89%) as a solid. LCMS: Calc'd 519.3, ESI-MS m/z=520.27 [M+H]+. $^1$H NMR (400 MHz, DMSO-d6): δ 1.18-1.32 (m, 3H), 1.55-1.70 (m, 2H), 1.72-1.85 (m, 2H), 2.07-2.10 (m, 1H), 3.15-3.25 (m, 2H), 3.58 (s, 3H), 3.66-3.70 (m, 1H), 4.07-4.12 (m, 2H), 4.47-4.49 (m, 1H), 7.40-7.42 (m, 1H), 7.70-7.73 (m, 2H), 8.74 (s, 1H,), 9.27 (s, 1H), 10.52 (s, 1H).

Step-3: (R)-2-(1-(3,4-dichlorobenzoyl)piperidin-3-yl)-5-hydroxy-N-(isoxazol-4-yl)-1-methyl-6-oxo-1,6-dihydropyrimidine-4-carboxamide To a stirred solution of (R)-2-(1-(3,4-dichlorobenzoyl)piperidin-3-yl)-5-ethoxy-N-(isoxazol-4-yl)-1-methyl-6-oxo-1,6-dihydropyrimidine-4-carboxamide (0.608 g, 1.16 mmol) was dissolved in dichloromethane (36 mL). The resulting solution was cooled to 0° C. and 1M $BBr_3$ in dichloromethane (4.67 mL, 4.67 mmol) was added dropwise. The reaction mixture was warmed to room temperature and stirred for 5 h. Upon completion, the reaction mixture was concentrated, and azeotroped with dichloromethane (2×6 mL). The residue was cooled to 0° C. and methanol (5 mL) was added slowly. The reaction mixture was concentrated under vacuum to dryness. The residue was azeotroped with methanol (2×6 mL) to give the crude compound. The crude compound was loaded on celite and purified by reverse phase column chromatography using acetonitrile and 0.1% formic acid in water to give Example 131 (0.246 g, 42%). LCMS: Calc'd 491.3, ESI-MS m/z=492.3 [M+H]+. $^1$H NMR (400 MHz, DMSO-d6): δ 1.44-1.62 (m, 2H), 1.80-1.95 (m, 2H), 2.07-2.10 (m, 1H), 3.15-3.25 (m, 2H), 3.57 (s, 3H), 3.60-3.70 (m, 1H), 4.34-4.52 (m, 1H), 7.40-7.42(m, 1H), 7.70-7.74 (m, 2H), 8.84-8.90 (m, 1H,), 9.30 (s, 1H), 10.42-10.55 (m, 1H), 11.48 (s, 1H).

The following examples and intermediates were synthesized using similar conditions as those described in the step, above, along with appropriate starting materials.

TABLE 7

| Example | Structure | Name | LCMS |
|---|---|---|---|
| 82 | 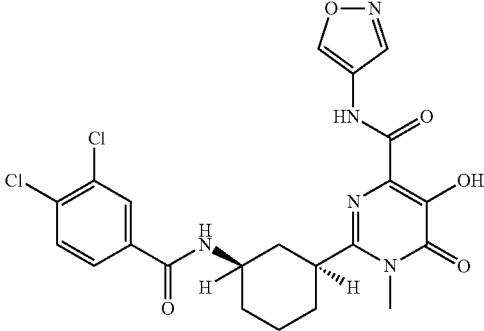 [SMILES: Cn1c([C@H]2CCC[C@@H](NC(=O)c3ccc(Cl)c(Cl)c3)C2)nc(C(=O)Nc2cnoc2)c(O)c1=O] | 2-((1S,3R)-3-(3,4-dichlorobenzamido)cyclohexyl)-5-hydroxy-N-(isoxazol-4-yl)-1-methyl-6-oxo-1,6-dihydropyrimidine-4-carboxamide | ESI-MS m/z = 507.3 [M + H]+. Calculated MW: 506.4 |
| 83 | 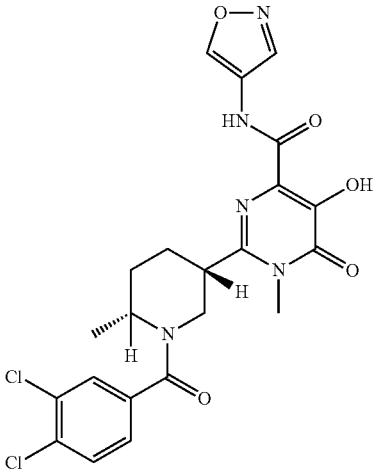 [SMILES: C[C@@H]1CC[C@H](c2nc(C(=O)Nc3cnoc3)c(O)c(=O)n2C)CN1C(=O)c1ccc(Cl)c(Cl)c1] | 2-((3S,6R)-1-(3,4-dichlorobenzoyl)-6-methylpiperidin-3-yl)-5-hydroxy-N-(isoxazol-4-yl)-1-methyl-6-oxo-1,6-dihydropyrimidine-4-carboxamide | ESI-MS m/z = 506.2 [M + H]+. Calculated MW: 505.1 |

TABLE 7-continued

| Example | Structure | Name | LCMS |
|---|---|---|---|
| 84 | 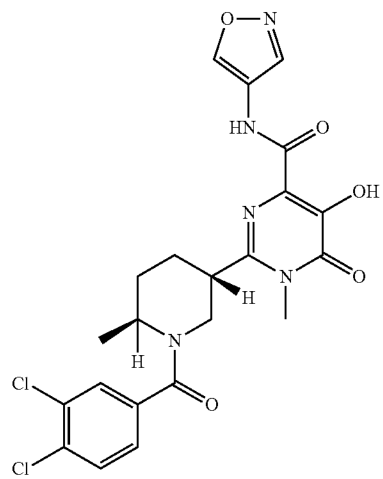 [SMILES: C[C@H]1CC[C@H](c2nc(C(=O)Nc3cnoc3)c(O)c(=O)n2C)CN1C(=O)c1ccc(Cl)c(Cl)c1] | 2-((3S,6S)-1-(3,4-dichlorobenzoyl)-6-methylpiperidin-3-yl)-5-hydroxy-N-(isoxazol-4-yl)-1-methyl-6-oxo-1,6-dihydropyrimidine-4-carboxamide | ESI-MS m/z = 506.2 [M + H]+. Calculated MW: 505.1 |
| 85 | 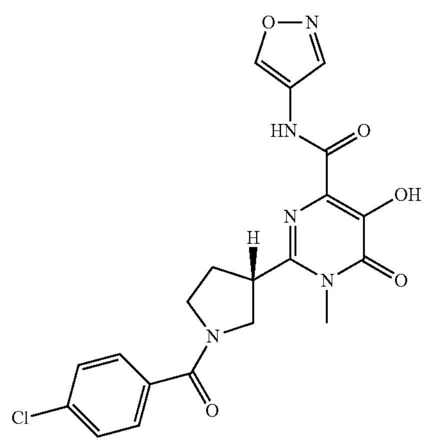 [SMILES: Cn1c([C@H]2CCN(C(=O)c3ccc(Cl)cc3)C2)nc(C(=O)Nc2cnoc2)c(O)c1=O] | (S)-2-(1-(4-chlorobenzoyl)pyrrolidin-3-yl)-5-hydroxy-N-(isoxazol-4-yl)-1-methyl-6-oxo-1,6-dihydropyrimidine-4-carboxamide | ESI-MS m/z = 444.4 [M + H]+. Calculated MW: 443.8 |
| 86 | 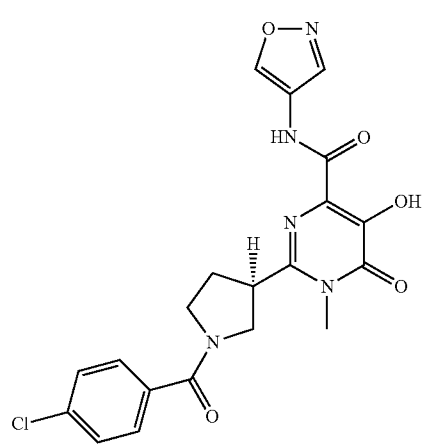 [SMILES: Cn1c([C@@H]2CCN(C(=O)c3ccc(Cl)cc3)C2)nc(C(=O)Nc2cnoc2)c(O)c1=O] | (R)-2-(1-(4-chlorobenzoyl)pyrrolidin-3-yl)-5-hydroxy-N-(isoxazol-4-yl)-1-methyl-6-oxo-1,6-dihydropyrimidine-4-carboxamide | ESI-MS m/z = 444.4 [M + H]+. Calculated MW: 443.8 |

TABLE 7-continued

| Example | Structure | Name | LCMS |
|---------|-----------|------|------|
| 87 | 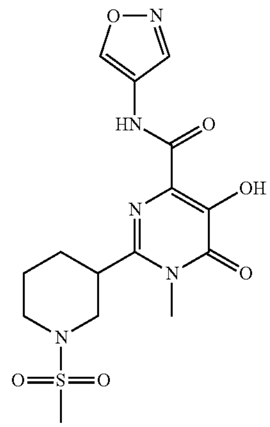 [SMILES: Cn1c(C2CCCN(S(C)(=O)=O)C2)nc(C(=O)Nc2cnoc2)c(O)c1=O] | 5-hydroxy-N-(isoxazol-4-yl)-1-methyl-2-(1-(methylsulfonyl)piperidin-3-yl)-6-oxo-1,6-dihydropyrimidine-4-carboxamide | ESI-MS m/z = 396.3 [M − H]+. Calculated MW: 397.1 |
| 88 | 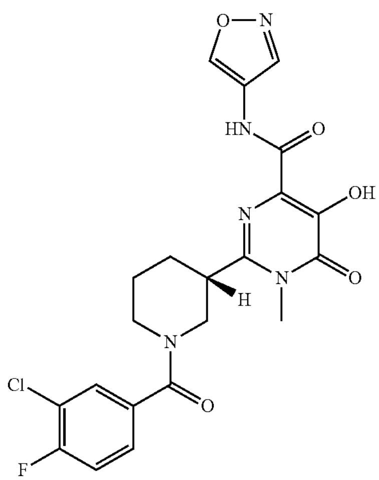 [SMILES: Cn1c([C@H]2CCCN(C(=O)c3ccc(F)c(Cl)c3)C2)nc(C(=O)Nc2cnoc2)c(O)c1=O] | (S)-2-(1-(3-chloro-4-fluorobenzoyl)piperidin-3-yl)-5-hydroxy-N-(isoxazol-4-yl)-1-methyl-6-oxo-1,6-dihydropyrimidine-4-carboxamide | ESI-MS m/z = 476.3 [M − H]+. Calculated MW: 475.9 |
| 89-90 | Intentionally Omitted | | |
| 91 | 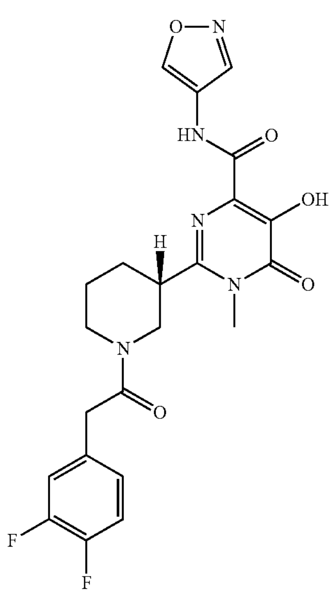 [SMILES: Cn1c([C@H]2CCCN(C(=O)Cc3ccc(F)c(F)c3)C2)nc(C(=O)Nc2cnoc2)c(O)c1=O] | (S)-2-(1-(2-(3,4-difluorophenyl)acetyl)piperidin-3-yl)-5-hydroxy-N-(isoxazol-4-yl)-1-methyl-6-oxo-1,6-dihydropyrimidine-4-carboxamide | ESI-MS m/z = 474.3 [M − H]+. Calculated MW: 473.4 |

TABLE 7-continued

| Example | Structure | Name | LCMS |
|---|---|---|---|
| 92 | 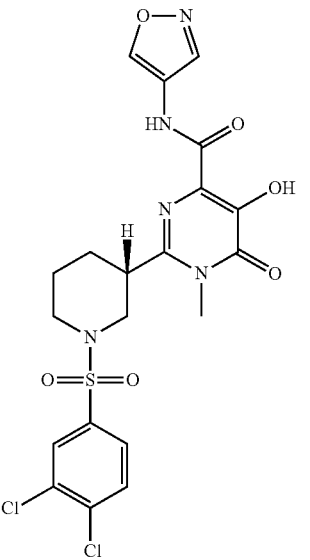 [SMILES: Cn1c([C@H]2CCCN(S(=O)(=O)c3ccc(Cl)c(Cl)c3)C2)nc(C(=O)Nc2cnoc2)c(O)c1=O] | (S)-2-(1-((3,4-dichlorophenyl)sulfonyl)piperidin-3-yl)-5-hydroxy-N-(isoxazol-4-yl)-1-methyl-6-oxo-1,6-dihydropyrimidine-4-carboxamide | ESI-MS m/z = 528.4 [M − H]+. Calculated MW: 527.4 |
| 93 | 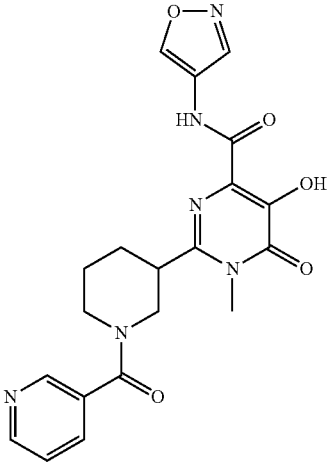 [SMILES: Cn1c(C2CCCN(C(=O)c3cccnc3)C2)nc(C(=O)Nc2cnoc2)c(O)c1=O] | 5-hydroxy-N-(isoxazol-4-yl)-1-methyl-2-(1-nicotinoylpiperidin-3-yl)-6-oxo-1,6-dihydropyrimidine-4-carboxamide | ESI-MS m/z = 425.3 [M − H]+. Calculated MW: 424.4 |
| 94 | 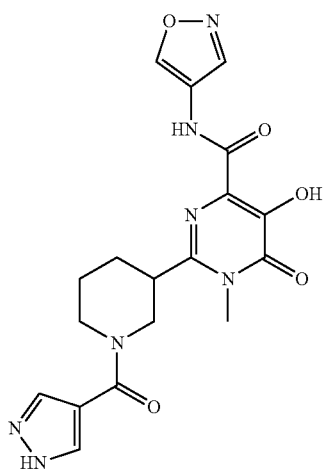 [SMILES: Cn1c(C2CCCN(C(=O)c3cn[nH]c3)C2)nc(C(=O)Nc2cnoc2)c(O)c1=O] | 2-(1-(1H-pyrazole-4-carbonyl)piperidin-3-yl)-5-hydroxy-N-(isoxazol-4-yl)-1-methyl-6-oxo-1,6-dihydropyrimidine-4-carboxamide | ESI-MS m/z = 414.4 [M + H]+. Calculated MW: 413.4 |

TABLE 7-continued

| Example | Structure | Name | LCMS |
|---|---|---|---|
| 95 | 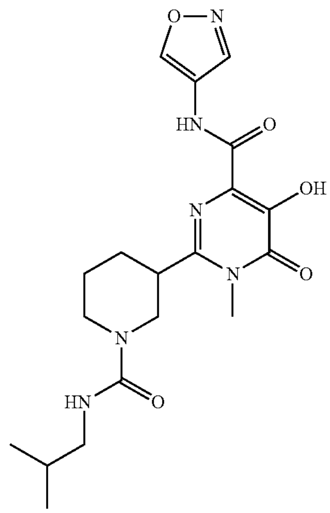 [SMILES: CC(C)CNC(=O)N1CCCC(c2nc(C(=O)Nc3cnoc3)c(O)c(=O)n2C)C1] | 5-hydroxy-2-(1-isobutyrylpiperidin-3-yl)-N-(isoxazol-4-yl)-1-methyl-6-oxo-1,6-dihydropyrimidine-4-carboxamide | ESI-MS m/z = 419.3 [M + H]+. Calculated MW: 418.5 |
| 96 | 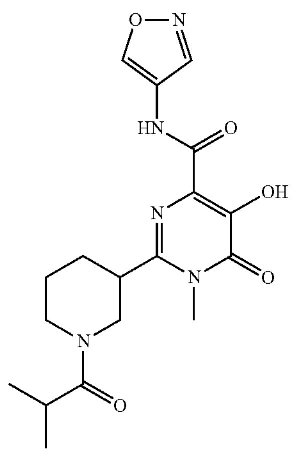 [SMILES: CC(C)C(=O)N1CCCC(c2nc(C(=O)Nc3cnoc3)c(O)c(=O)n2C)C1] | 5-hydroxy-2-(1-isobutyrylpiperidin-3-yl)-N-(isoxazol-4-yl)-1-methyl-6-oxo-1,6-dihydropyrimidine-4-carboxamide | ESI-MS m/z = 390.3 [M + H]+. Calculated MW: 389.4 |
| 97 | 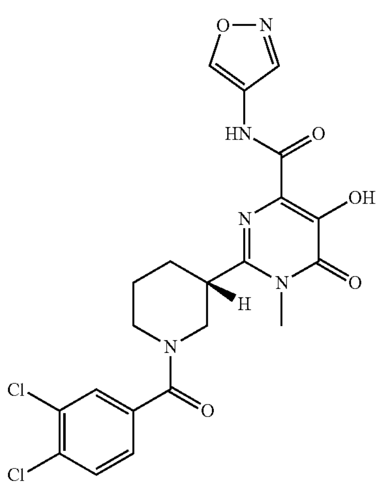 [SMILES: Cn1c([C@H]2CCCN(C(=O)c3ccc(Cl)c(Cl)c3)C2)nc(C(=O)Nc2cnoc2)c(O)c1=O] | (S)-2-(1-(3,4-dichlorobenzoyl)piperidin-3-yl)-5-hydroxy-N-(isoxazol-4-yl)-1-methyl-6-oxo-1,6-dihydropyrimidine-4-carboxamide | ESI-MS m/z = 492.6 [M + H]+. Calculated MW: 491.1 |

Synthesis of 2-(1-(3,4-dichlorobenzoyl)-3-methylpiperidin-3-yl)-5-hydroxy-N-(isoxazol-4-yl)-1-methyl-6-oxo-1,6-dihydropyrimidine-4-carboxamide. (Example 130)
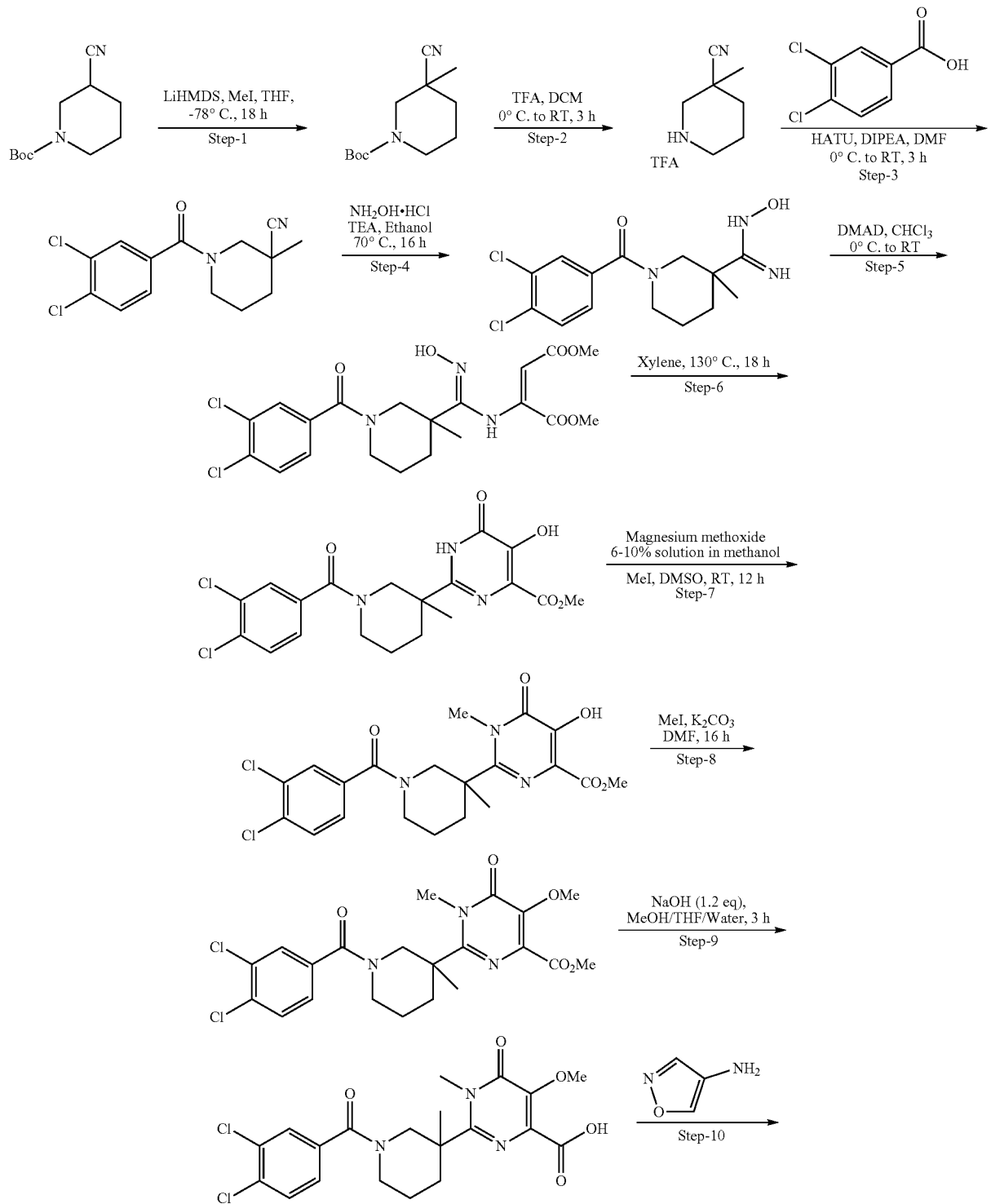

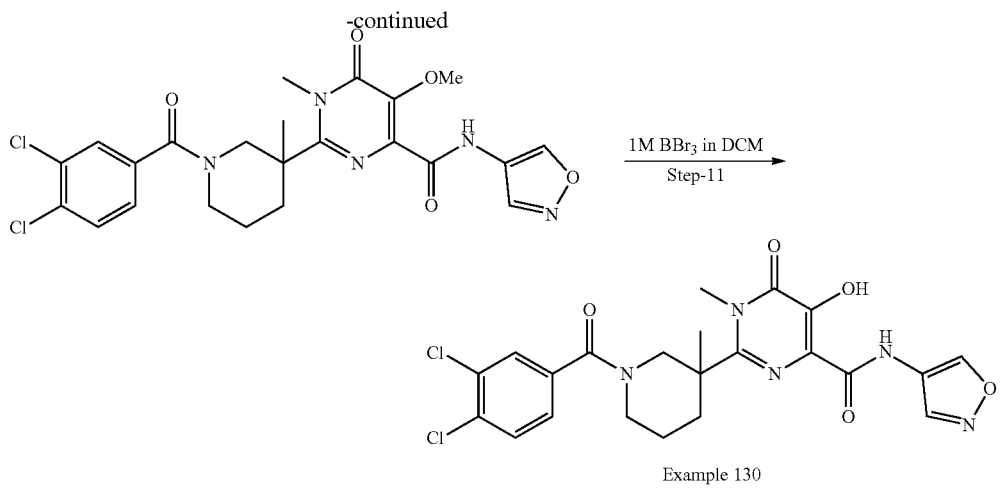

Example 130

Step-1: tert-butyl 3-cyano-3-methylpiperidine-1-carboxylate

To a stirred solution of tert-butyl 3-cyanopiperidine-1-carboxylate (5.0 g, 24 mmol) in dry THF (100 mL) was added LiHMDS (30.9 mL, 1M in THF, 30.9 mmol) at −78° C. The reaction mixture was stirred at −78° C. for 30 min. Then MeI (2.22 mL, 35.7 mmol) was added at the same temperature. The reaction mixture was stirred at room temperature for 16 h. After completion of reaction, the reaction mixture was poured into mixture of ice-cold water (100 mL) and extracted with ethyl acetate (2×150 mL). The combined organic layer was washed with brine (50 mL), dried over anhydrous $Na_2SO_4$ and concentrated under reduced pressure. The resulting residue was purified by silica gel chromatography to afford the pure title compound (3.5 g, 65%) $^1$H NMR (400 MHz, DMSO-$d_6$): δ 1.35 (s, 3H), 1.43 (s, 9H), 1.66-1.70 (m, 1H), 1.78-1.81 (m, 2H), 1.87-2.10 (m, 1H), 2.80 (s, 2H), 3.90-4.20 (m, 2H).

Step-2: 3-methylpiperidine-3-carbonitrile TFA Salt

To a stirred solution of tert-butyl 3-cyano-3-methylpiperidine-1-carboxylate (3.5 g, 15.6 mmol) in dichloromethane (70 mL) was added TFA (12.7 mL) dropwise at 0° C. The resulting mixture was stirred at room temperature for 3 h. The reaction mixture was concentrated under reduced pressure to give crude compound. Crude compound was triturated with diethyl ether to afford title compound (3.0 g, 81%) as a TFA salt. $^1$H NMR (400 MHz, DMSO-$d_6$): δ 1.40 (s, 3H), 1.63-1.69 (m, 2H), 1.76-1.81 (m, 1H), 1.91-2.06 (m, 1H), 2.82-2.89 (m, 1H), 3.01-3.09 (m, 1H), 3.19-3.22 (m, 1H), 3.56-3.59 (m, 1H), 9.20 (bs, 1H).

Step-3: 1-(3,4-dichlorobenzoyl)-3-methylpiperidine-3-carbonitrile

To a stirred solution of 3,4-dichloro benzoic acid (2.88 g, 15.1 mmol) in dry DMF (15 mL) was added HATU (7.18 g, 18.9 mmol) at room temperature. The reaction mixture was stirred at room temperature for 1 h. DIPEA (7 mL, 38 mmol) was added dropwise followed by the addition of 3-methylpiperidine-3-carbonitrile TFA salt (3.0 g, 12.6 mmol) at room temperature. The reaction mixture was stirred at room temperature for 3 h. After completion of reaction, the reaction mixture was diluted with water (30 mL) and the aqueous layer was extracted with ethyl acetate (2×200 mL). The combined organic layer was washed with brine (50 mL), dried over anhydrous $Na_2SO_4$ and concentrated under reduced pressure. The resulting residue was purified by column chromatography to give the pure title compound (2.8 g, 56%). LCMS: Calc'd 296.3, ESI-MS m/z=297.2 [M+H]$^+$.

Step-4: 1-(3,4-dichlorobenzoyl)-N-hydroxy-3-methylpiperidine-3-carboximidamide A mixture of 1-(3,4-dichlorobenzoyl)-3-methylpiperidine-3-carbonitrile (4 g, 13.5 mmol), hydroxylamine hydrochloride (2.80 g, 40.4 mmol) in ethanol (100 ml) was slowly added triethylamine (5.8 ml, 40.4 mmol) at 0° C. The resulting reaction mixture was heated at 70° C. for 16 h, then concentrated, diluted with water (100 mL) and extracted with 10% methanol in dichloromethane (2×150 mL). The combined organic layer was dried over anhydrous $Na_2SO_4$ and concentrated under reduced pressure to obtain title compound (5.0 g, 69%) as a solid. The crude product was used in the next step without further purification. LCMS: Calc'd 329.3, ESI-MS m/z=330.4 [M+H]$^+$.

Step-5: Dimethyl 2-((E)-1-(3,4-dichlorobenzoyl)-N'-hydroxy-3-methylpiperidine-3-carboximidamido) maleate To a stirred solution of 1-(3,4-dichlorobenzoyl)-N-hydroxy-3-methylpiperidine-3-carboximidamide (5.0 g, 15 mmol) in chloroform (100 mL) was added dimethyl acetylenedicarboxylate (3.32 g, 23.4 mmol) dropwise at 0° C. and reaction mixture was stirred at room temperature for overnight. Reaction was monitored by the TLC and then concentrated to give crude product that was purified by silica gel column chromatography to obtain pure title compound (2.4 g, 33%) as a solid. LCMS: Calc'd 471.2, ESI-MS m/z=472.3 [M+H]$^+$.

Step-6: Methyl 2-(1-(3,4-dichlorobenzoyl)-3-methylpiperidin-3-yl)-5-hydroxy-6-oxo-1,6-dihydropyrimidine-4-carboxylate A solution of dimethyl 2-((E)-1-(tert-butoxycarbonyl)-N'-hydroxypiperidine-3-carboximidamido) maleate (2.0 g, 4.2 mmol) in xylenes (15 mL) was heated in a microwave at 160° C. for 10 min. Reaction mixture was concentrated and triturated with diethyl ether and hexanes to obtain solid. The crude residue was loaded on celite and purified by reverse phase column chromatography using acetonitrile and 0.1% formic acid in water to give the pure title compound (0.40 g, 21%). LCMS: LCMS: Calc'd 439.4, ESI-MS m/z=440.5 [M+H]$^+$. $^1$H NMR (400 MHz, DMSO-d$_6$): δ 1.10 (s, 2H), 1.27 (s, 3H), 1.58-1.75 (m, 3H), 2.00-2.16 (m, 1H), 3.79 (s, 3H), 3.60-3.64 (m, 1H), 4.01 (bs, 1H), 7.26 (d, J=8.4, 1H), 7.54 (s, 1H), 7.67 (d, J=2.0 Hz, 1H), 10.36 (s, 1H), 12.40-12.65 (m, 1H).

Step-7: methyl 2-(1-(3, 4-dichlorobenzoyl)-3-methylpiperidin-3-yl)-5-hydroxy-1-methyl-6-oxo-1, 6-dihydropyrimidine-4-carboxylate A mixture of methyl 2-(1-(3,4-dichlorobenzoyl)-3-methylpiperidin-3-yl)-5-hydroxy-6-oxo-1,6-dihydropyrimidine-4-carboxylate (0.200 g, 0.454 mmol) was dissolved in DMSO (50 mL) and it was cooled to 0° C. To this, magnesium methoxide solution (1.30 mL, 0.908 mmol, 6 to 10% in methanol) was added dropwise at 0° C. The reaction mixture was stirred at room temperature for 1 h. Reaction mixture was concentrated to remove excess of methanol. The reaction mixture was cooled to 0° C. and MeI (0.116 mL, 1.81 mmol) was added dropwise. Reaction mixture was stirred at room temperature for 16 h, then cooled to 10° C. and quenched with 1N HCl slowly. The product was extracted with ethyl acetate (2×200 mL). The combined organic layer was dried over anhydrous Na$_2$SO$_4$ and concentrated under reduced pressure. The crude residue was loaded on celite and purified by reverse phase column chromatography using acetonitrile and 0.1% formic acid in water to give the pure title compound (0.20 g, 97%). LCMS: Calc'd 453.4, ESI-MS m/z=454.2 [M+H]$^+$. $^1$H NMR (400 MHz, DMSO-d6): δ 1.39 (s, 3H), 1.59 (bs, 1H), 1.75 (bs, 1H), 2.01-2.07 (m, 2H), 3.15-3.25 (m, 1H), 3.32-3.52 (m, 1H), 3.63 (s, 3H), 3.79 (s, 3H), 3.83-3.86 (m, 1H), 3.99-4.02 (m, 1H), 7.30 (d, J=8.4 Hz, 1H), 7.55 (s, 1H), 7.69 (d, J=2.0 Hz, 1H), 10.32 (s, 1H).

Step-8: methyl 2-(1-(3,4-dichlorobenzoyl)-3-methylpiperidin-3-yl)-5-methoxy-1-methyl-6-oxo-1,6-dihydropyrimidine-4-carboxylate To a stirred solution of methyl 2-(1-(3,4-dichlorobenzoyl)-3-methylpiperidin-3-yl)-5-hydroxy-1-methyl-6-oxo-1,6-dihydropyrimidine-4-carboxylate (0.20 g, 0.44 mmol) in DMF (1 mL) was added K$_2$CO$_3$ (0.121 g, 0.875 mmol) followed by the addition of MeI (0.042 mL, 0.660 mmol) at room temperature. Reaction mixture was stirred at room temperature for 4 h. After completion of reaction, it was diluted with water (20 mL) and the aqueous layer was extracted with ethyl acetate (2×20 mL). The combined organic layer was washed with brine (10 mL), dried over anhydrous Na$_2$SO$_4$ and concentrated under reduced pressure. The resulting residue was purified by column chromatography to give the pure title compound (0.14 g, 67%). LCMS: Calc'd 467.4, ESI-MS m/z=468.3 [M+H]$^+$ Step-9: 2-(1-(3,4-dichlorobenzoyl)-3-methylpiperidin-3-yl)-5-methoxy-1-methyl-6-oxo-1,6-dihydropyrimidine-4-carboxylic acid To a stirred solution of methyl 2-(1-(3,4-dichlorobenzoyl)-3-methylpiperidin-3-yl)-5-methoxy-1-methyl-6-oxo-1,6-dihydropyrimidine-4-carboxylate (0.140 g, 0.298 mmol) in a mixture of methanol:THF:water (1:1:1, 6 mL) was added NaOH (0.014 g, 0.36 mmol) at room temperature. The reaction mixture was stirred at room temperature for 3 h. After completion of reaction, the reaction mixture was concentrated under reduced pressure, diluted with ice cold water (10 mL) and extracted with ethyl acetate (2×10 mL). The combined aqueous layer was acidified with 1 N HCl at 0° C. and extracted with 10% methanol in dichloromethane (2×30 mL). The combine organic layer was washed with brine (20 mL), dried over anhydrous Na$_2$SO$_4$ and concentrated under reduced pressure to afford crude title compound. (0.130 g, 96%). LCMS: Calc'd 455.2, ESI-MS m/z=456.6 [M+H]$^+$ Step-10: 2-(1-(3,4-dichlorobenzoyl)-3-methylpiperidin-3-yl)-N-(isoxazol-4-yl)-5-methoxy-1-methyl-6-oxo-1,6-dihydropyrimidine-4-carboxamide To a stirred solution of 2-(1-(3,4-dichlorobenzoyl)-3-methylpiperidin-3-yl)-5-methoxy-1-methyl-6-oxo-1,6-dihydropyrimidine-4-carboxylic acid (0.140 g, 0.308 mmol) in dry DMF (1.4 mL) was added HATU (0.176 g, 0.462 mmol) at room temperature. The reaction mixture was stirred at room temperature for 1 h and then, DIPEA (0.17 mL, 0.99 mmol) and isoxazol-4-amine (0.038 g, 0.46 mmol) were added at room temperature. The reaction mixture was stirred at room temperature for 3 h, then diluted with water (20 mL) and extracted with ethyl acetate (2×20 mL). The combined organic layer was washed with brine (10 mL), dried over anhydrous Na$_2$SO$_4$ and concentrated under reduced pressure. The resulting residue was purified by column chromatography to give pure title compound (0.135 g, 84%) as a solid. LCMS: Calc'd 519.2, ESI-MS m/z=520.4 [M+H]$^+$. $^1$H NMR (400 MHz, DMSO-d$_6$): δ 1.16-1.19 (m, 3H), 1.19-1.23 (m, 2H), 1.42-1.56 (m, 2H), 3.32-3.52 (m, 2H) 3.62 (s, 3H), 4.01-4.02 (m, 1H), 4.03 (s, 3H), 4.70-4.77 (m, 1H), 7.25-7.27 (m, 1H), 7.59-7.67 (m, 2H), 8.74 (s, 1H), 9.27 (s, 1H), 10.58 (bs, 1H). Chiral HPLC: CHIRALPAK AD-H; 30% (MEOH) in Liquid CO2+0.1% DEA: FR-1 (Isomer-1): R$_T$=9.39; FR-2 (Isomer-2): R$_T$=14.82.

Step-11: 2-(1-(3,4-dichlorobenzoyl)-3-methylpiperidin-3-yl)-5-hydroxy-N-(isoxazol-4-yl)-1-methyl-6-oxo-1,6-dihydropyrimidine-4-carboxamide A stirred solution of 2-(1-(3,4-dichlorobenzoyl)-3-methylpiperidin-3-yl)-N-(isoxazol-4-yl)-5-methoxy-1-methyl-6-oxo-1,6-dihydropyrimidine-4-carboxamide FR-1 (0.030 g, 0.057 mmol) dissolved in dichloromethane (2 mL) was cooled to 0° C. and 1M BBr$_3$ in dichloromethane (0.28 mL, 0.29 mmol) was added dropwise. The reaction mixture was then stirred at room temperature for 3 h. After completion of reaction and then concentrated under vacuum. Methanol (1 mL) was added and stirred for 30 min and evaporated. The residue was azeotroped with Methanol (2×1 ml) to give the crude compound (120 mg). The crude residue was loaded on celite and purified by reverse phase column chromatography using acetonitrile and 0.1% formic acid in water to give Example 130 (0.015 g, 51%). LCMS: Calc'd 505.2, ESI-MS m/z=506.3 [M+H]$^+$. $^1$H NMR (400 MHz, DMSO-d6): δ 1.35-1.45 (m, 3H), 1.46-1.60 (m, 2H), 1.70-1.80 (m, 2H), 3.15-3.18 (m, 2H), 3.38-3.44 (m, 2H), 3.61 (s, 3H), 7.22-7.24 (m, 1H), 7.59-7.64 (m, 2H), 8.73 (s, 1H), 9.23 (s, 1H), 10.75 (bs, 1H), 11.58 (bs, 1H).

Synthesis of 5-hydroxy-N-(isoxazol-4-yl)-1-methyl-6-oxo-2-(1-phenethylpiperidin-3-yl)-1,6-dihydropyrimidine-4-carboxamide (Example 129)

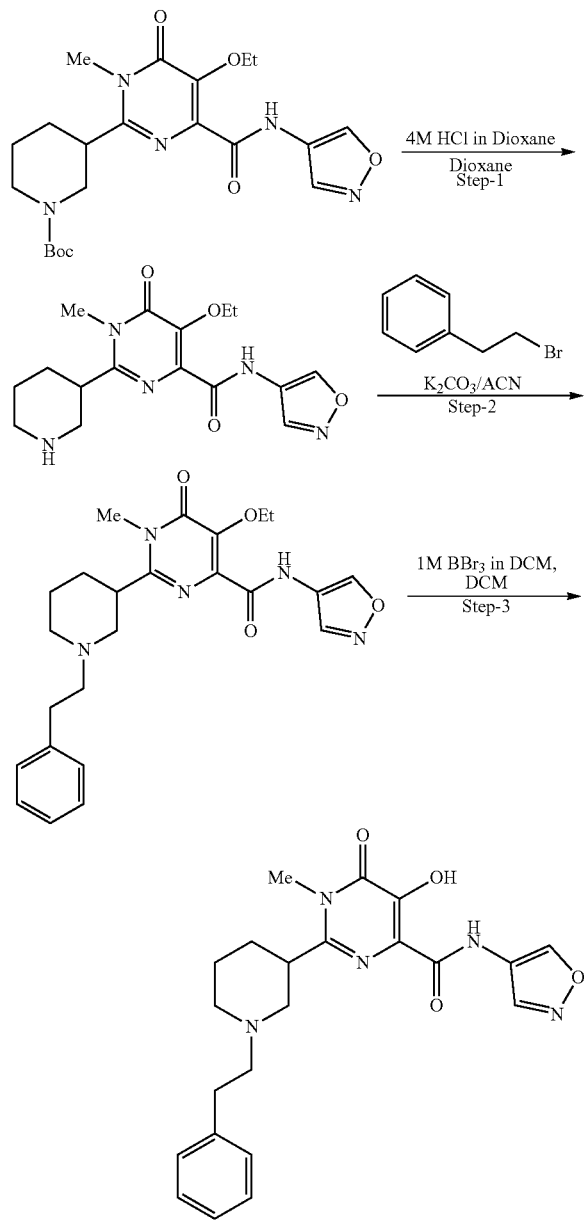

Example 129

Step-1: 5-ethoxy-N-(isoxazol-4-yl)-1-methyl-6-oxo-2-(piperidin-3-yl)-1,6-dihydropyrimidine-4-carboxamide hydrochloride salt To a stirred solution of tert-butyl 3-(5-ethoxy-4-(isoxazol-4-ylcarbamoyl)-1-methyl-6-oxo-1,6-dihydropyrimidin-2-yl)piperidine-1-carboxylate [from the synthesis of A1] (0.35 g, 0.78 mmol) in mixture of dichloromethane (3 mL) and Methanol (0.5 mL) was added 4M HCl in dioxane (3 mL) dropwise at 0° C. The reaction mixture was stirred at room temperature for 1 h and warmed to 40° C. for 10 min. The reaction mixture was concentrated to dryness and azeotroped twice with methanol to afford the title compound as solid (0.290 g, 97%) which was used in the next step without further purification. LCMS: Calc'd 347.5; ESI-MS m/z=348.5 [M+H]$^+$ Step-2: 5-ethoxy-N-(isoxazol-4-yl)-1-methyl-6-oxo-2-(1-phenethylpiperidin-3-yl)-1,6-dihydropyrimidine-4-carboxamide To a stirred solution of 5-ethoxy-N-(isoxazol-4-yl)-1-methyl-6-oxo-2-(piperidin-3-yl)-1,6-dihydropyrimidine-4-carboxamide hydrochloride salt (0.050 g, 0.130 mmol) in DMF (0.5 mL) was added triethylamine (0.055 mL, 0.391 mmol) and stirred at room temperature for 30 min. (2-bromoethyl)benzene (0.024 g, 0.130 mmol) was added and reaction mixture was stirred at room temperature for 4 h, then concentrated. The obtained crude product was triturated with hexanes (5 mL) and dried under vacuum to afford title compound (0.050 g). The crude title compound was used in the next step without further purification. LCMS: Calc'd 451.3; ESI-MS m/z=452.4 [M+H]$^+$ Step-3: 5-hydroxy-N-(isoxazol-4-yl)-1-methyl-6-oxo-2-(1-phenethylpiperidin-3-yl)-1,6-dihydropyrimidine-4-carboxamide A mixture of 5-ethoxy-N-(isoxazol-4-yl)-1-methyl-6-oxo-2-(1-phenethylpiperidin-3-yl)-1,6-dihydropyrimidine-4-carboxamide (0.05 g, 0.110 mmol) was dissolved in dichloromethane (1 mL). The resulting solution was cooled to 0° C. and 1M BBr$_3$ in dichloromethane (0.22 mL, 0.22 mmol) was added drop wise. The reaction mixture was stirred at room temperature for 5 h, then saturated sodium bicarbonate (0.5 mL) was added and further diluted with 10% methanol in dichloromethane. The residue was dried over Na$_2$SO$_4$ and concentrated to dryness. The crude residue was loaded on celite and purified by reverse phase column chromatography using acetonitrile and 0.1% formic acid in water to give pure title compound (0.01 g, 21%). LCMS: Calc'd 423.4: ESI-MS m/z=424.5 [M+H]$^+$ $^1$H NMR (400 MHz, DMSO-d6): δ 1.60-1.80 (m, 4H), 1.85-1.95 (m, 1H), 2.66-2.70 (m, 2H), 2.70-3.02 (m, 6H), 3.48 (s, 3H), 7.18-7.28 (m, 5H), 8.77 (s, 1H,), 9.13 (s, 1H), 10.25 (bs, 1H), 11.50 (bs, 1H).

The following examples and intermediates were synthesized using similar conditions as those described in the step, above, along with appropriate starting materials.

TABLE 8

| Example | Structure | Name | LCMS |
|---|---|---|---|
| 98 | (structure shown) | 5-hydroxy-N-(isoxazol-4-yl)-1-methyl-6-oxo-2-(1-(2,2,2-trifluoroethyl)piperidin-3-yl)-1,6-dihydropyrimidine-4-carboxamide | ESI-MS m/z = 402.3 [M + H]+. Calculated MW: 401.3 |
| 99 | Intentionally Omitted | | |

Synthesis of 5-hydroxy-N-(isoxazol-4-yl)-1-methyl-6-oxo-2-(piperidin-1-yl)-1,6-dihydropyrimidine-4-carboxamide (Example 28)

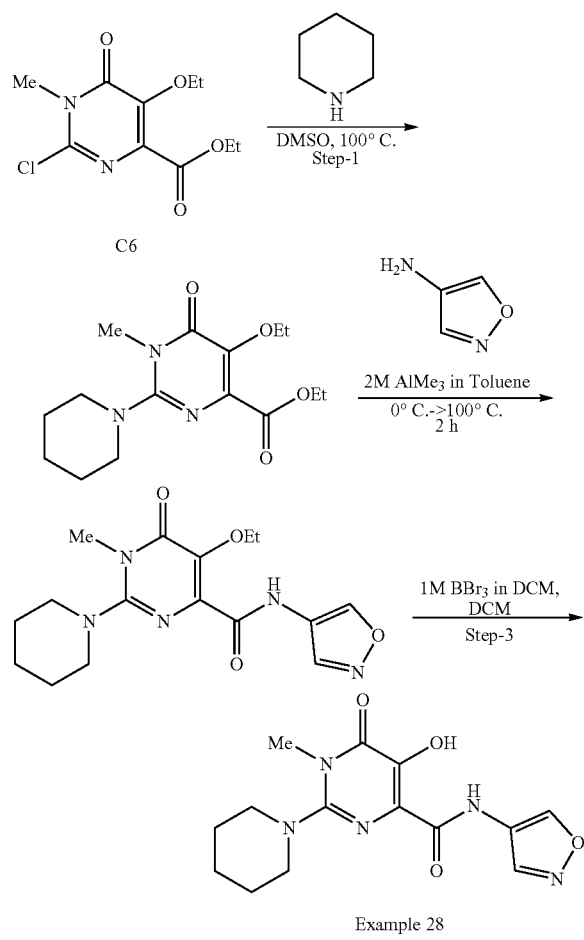

Step-1:
A mixture of C6 (200 mg, 0.769 mmol), Piperidine (0.76 ml, 7.69 mmol) and DMSO was heated at 110° C. for 1 h. Reaction progress was monitored by the TLC and it was cooled to room temperature upon consumption of C6. Reaction mixture was poured into mixture of ice water (25 ml) and stirred well for 15 min. The solid material was filtered out, washed with water (3×10 ml) and dried well under vacuum to afford pure product as a solid (172 mg, 72%). ESI-MS m/z=310.38 [M+H]+ Calculated MW: 309.37 $^1$H NMR (400 MHz, DMSO-$d_6$): δ 4.00 (q, 2H), 4.26 (q, 2H), 3.38 (s, 3H), 3.04-3.06 (m, 4H), 1.57-1.62 (m, 6H), 1.20-1.30 (m, 6H).

Step-2: To a stirred solution of ethyl 5-ethoxy-1-methyl-6-oxo-2-(piperidin-1-yl)-1,6-dihydropyrimidine-4-carboxylate (100 mg, 0.32 mmol), isoxazol-4-amine (35.3 mg, 0.42 mmol) in toluene (1 mL) was added 2M trimethyl aluminum in toluene (0.6 ml, 0.64 mmol) at 0° C. The reaction mixture was heated at 80° C. for 30 min under microwave irradiation. The reaction completion was confirmed by the TLC and reaction poured into a mixture of ice cold water and extracted with ethyl acetate (2×10 ml). The organic layer was washed with brine (2×10 mL). The combined organic layer was dried over $Na_2SO_4$ and evaporated under vacuum to get the crude compound as light brown solid (104 mg). Crude material was used in the next step without any purification. ESI-MS m/z=348.5 [M+H]+ Calculated MW: 347.3

Step-3: 5-ethoxy-N-(isoxazol-4-yl)-1-methyl-6-oxo-2-(piperidin-1-yl)-1,6-dihydropyrimidine-4-carboxamide (100 mg, 0.28 mmol) was dissolved in dichloromethane (1 mL). To the resulting solution, was cooled to 0° C. and 1M $BBr_3$ in dichloromethane (0.5 mL, 0.57 mmol) was added drop wise. The reaction mixture was stirred at room temperature for 2 h. Reaction was monitored by the TLC (10% Methanol in dichloromethane). Upon completion, solvent was removed under vacuum. Ice cold water was added to the residue, and solid was filtered to get crude product (83 mg). The crude product was further purified by RP-HPLC to give Example 28, 5-hydroxy-N-(isoxazol-4-yl)-1-methyl-6-oxo-2-(piperidin-1-yl)-1,6-dihydropyrimidine-4-carboxamide product (10 mg, 0.032 mmol, 11%). ESI-MS m/z=320.3 [M+H]+ Calculated MW: 319.3 $^1$H NMR (400 MHz, DMSO-$d_6$): δ 11.19 (s, 1H), 10.54 (s, 1H), 9.31 (s, 1H), 8.92 (s, 1H), 3.43 (s, 3H), 3.08 (s, 4H), 1.59-1.67 (m, 6H).

The following examples and intermediates were synthesized using similar conditions as those described in the step, above, along with appropriate starting materials.

TABLE 9

| Example | Structure | Name | LCMS |
|---|---|---|---|
| 100 | 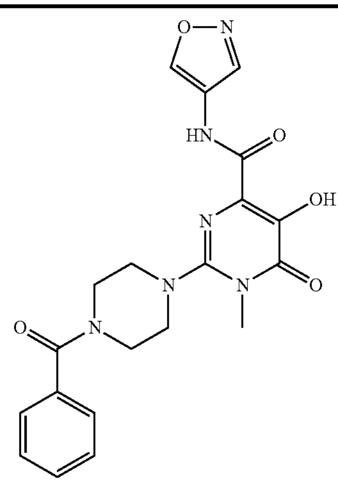 | 2-(4-benzoylpiperazin-1-yl)-5-hydroxy-N-(isoxazol-4-yl)-1-methyl-6-oxo-1,6-dihydropyrimidine-4-carboxamide | ESI-MS m/z = 425.6 [M + H]+. Calculated MW: 424.4 |

TABLE 9-continued

| Example | Structure | Name | LCMS |
|---|---|---|---|
| 101 | 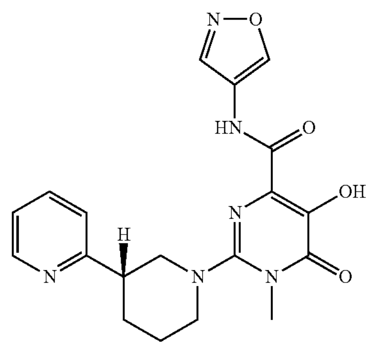 [SMILES: Cn1c(N2CCC[C@H](c3ccccn3)C2)nc(C(=O)Nc2cnoc2)c(O)c1=O] | (S)-5-hydroxy-N-(isoxazol-4-yl)-1-methyl-6-oxo-2-(3-(pyridin-2-yl)piperidin-1-yl)-1,6-dihydropyrimidine-4-carboxamide | ESI-MS m/z = 397.3 [M + H]+. Calculated MW: 396.4 |
| 102 | 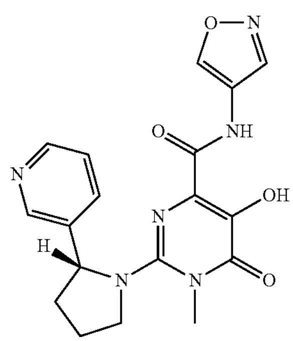 [SMILES: Cn1c(N2CCC[C@@H]2c2cccnc2)nc(C(=O)Nc2cnoc2)c(O)c1=O] | (R)-5-hydroxy-N-(isoxazol-4-yl)-1-methyl-6-oxo-2-(2-(pyridin-3-yl)pyrrolidin-1-yl)-1,6-dihydropyrimidine-4-carboxamide | ESI-MS m/z = 383.5 [M + H]+. Calculated MW: 382.4 |
| 103 | 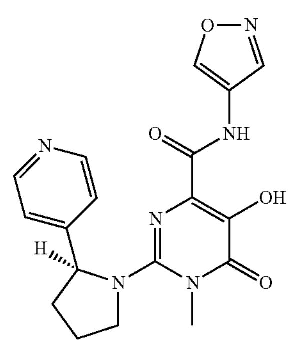 [SMILES: Cn1c(N2CCC[C@H]2c2ccncc2)nc(C(=O)Nc2cnoc2)c(O)c1=O] | (S)-5-hydroxy-N-(isoxazol-4-yl)-1-methyl-6-oxo-2-(2-(pyridin-4-yl)pyrrolidin-1-yl)-1,6-dihydropyrimidine-4-carboxamide | ESI-MS m/z = 383.5 [M + H]+. Calculated MW: 382.4 |
| 105 | Intentionally Omitted | | |
| 106 | 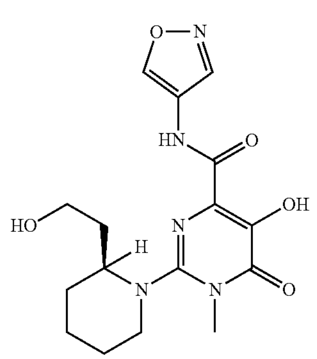 [SMILES: Cn1c(N2CCCC[C@H]2CCO)nc(C(=O)Nc2cnoc2)c(O)c1=O] | (S)-5-hydroxy-2-(2-(2-hydroxyethyl)piperidin-1-yl)-N-(isoxazol-4-yl)-1-methyl-6-oxo-1,6-dihydropyrimidine-4-carboxamide | ESI-MS m/z = 364.5 [M + H]+. Calculated MW: 363.4 |

TABLE 9-continued

| Example | Structure | Name | LCMS |
|---|---|---|---|
| 107 | 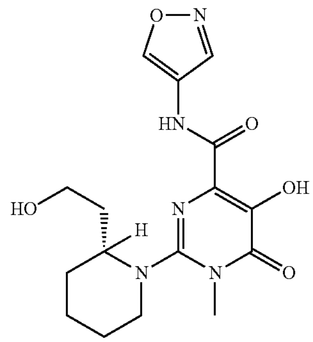 [SMILES: Cn1c(N2CCCC[C@@H]2CCO)nc(C(=O)Nc2cnoc2)c(O)c1=O] | (R)-5-hydroxy-2-(2-(2-hydroxyethyl)piperidin-1-yl)-N-(isoxazol-4-yl)-1-methyl-6-oxo-1,6-dihydropyrimidine-4-carboxamide | ESI-MS m/z = 364.3 [M + H]+. Calculated MW: 363.4 |
| 108 | 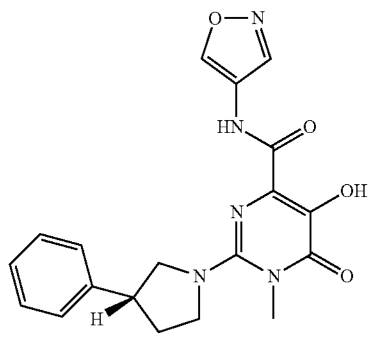 [SMILES: Cn1c(N2CC[C@H](c3ccccc3)C2)nc(C(=O)Nc2cnoc2)c(O)c1=O] | (R)-5-hydroxy-N-(isoxazol-4-yl)-1-methyl-6-oxo-2-(3-phenylpyrrolidin-1-yl)-1,6-dihydropyrimidine-4-carboxamide | ESI-MS m/z = 382.4 [M + H]+. Calculated MW: 381.4 |
| 109 | 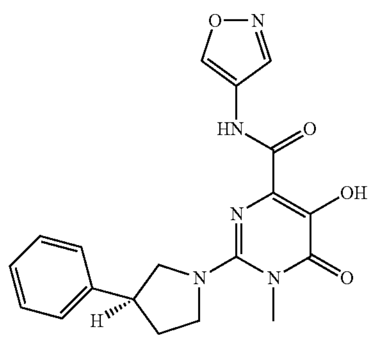 [SMILES: Cn1c(N2CC[C@@H](c3ccccc3)C2)nc(C(=O)Nc2cnoc2)c(O)c1=O] | (S)-5-hydroxy-N-(isoxazol-4-yl)-1-methyl-6-oxo-2-(3-phenylpyrrolidin-1-yl)-1,6-dihydropyrimidine-4-carboxamide | ESI-MS m/z = 382.4 [M + H]+. Calculated MW: 381.4 |
| 110 | 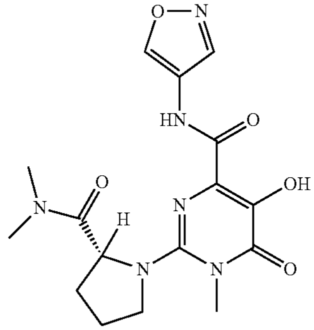 [SMILES: CN(C)C(=O)[C@H]1CCCN1c1nc(C(=O)Nc2cnoc2)c(O)c(=O)n1C] | (R)-2-(2-(dimethylcarbamoyl)pyrrolidin-1-yl)-5-hydroxy-N-(isoxazol-4-yl)-1-methyl-6-oxo-1,6-dihydropyrimidine-4-carboxamide | ESI-MS m/z = 377.2 [M + H]+. Calculated MW: 376.4 |

TABLE 9-continued

| Example | Structure | Name | LCMS |
|---|---|---|---|
| 111 | 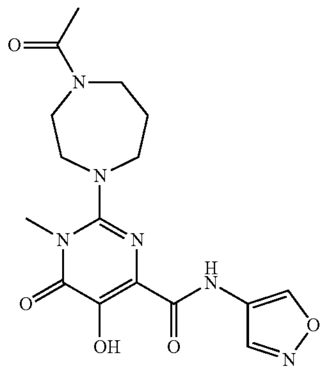 [SMILES: CC(=O)N1CCCN(c2nc(C(=O)Nc3cnoc3)c(O)c(=O)n2C)CC1] | 2-(4-acetyl-1,4-diazepan-1-yl)-5-hydroxy-N-(isoxazol-4-yl)-1-methyl-6-oxo-1,6-dihydropyrimidine-4-carboxamide | ESI-MS m/z = 377.4 [M + H]+. Calculated MW: 376.4 |
| 112 | 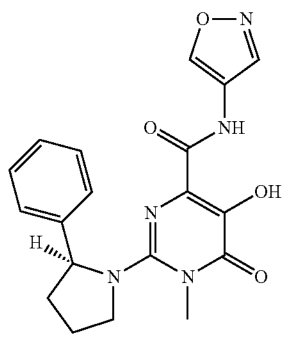 [SMILES: Cn1c(N2CCC[C@H]2c2ccccc2)nc(C(=O)Nc2cnoc2)c(O)c1=O] | (S)-5-hydroxy-N-(isoxazol-4-yl)-1-methyl-6-oxo-2-(2-phenylpyrrolidin-1-yl)-1,6-dihydropyrimidine-4-carboxamide | ESI-MS m/z = 382.3 [M + H]+. Calculated MW: 381.4 |
| 113 | 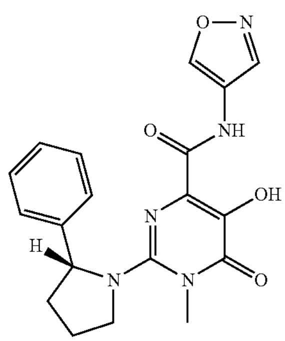 [SMILES: Cn1c(N2CCC[C@@H]2c2ccccc2)nc(C(=O)Nc2cnoc2)c(O)c1=O] | (R)-5-hydroxy-N-(isoxazol-4-yl)-1-methyl-6-oxo-2-(2-phenylpyrrolidin-1-yl)-1,6-dihydropyrimidine-4-carboxamide | ESI-MS m/z = 382.3 [M + H]+. Calculated MW: 381.4 |
| 49 | 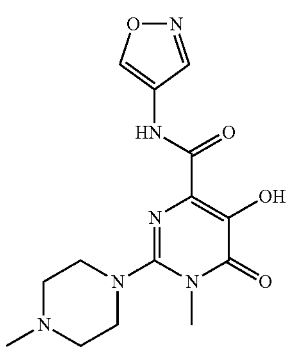 [SMILES: CN1CCN(c2nc(C(=O)Nc3cnoc3)c(O)c(=O)n2C)CC1] | 5-hydroxy-N-(isoxazol-4-yl)-1-methyl-2-(4-methylpiperazin-1-yl)-6-oxo-1,6-dihydropyrimidine-4-carboxamide | ESI-MS m/z = 335.4 [M + H]+. Calculated MW: 334.4 |

TABLE 9-continued

| Example | Structure | Name | LCMS |
|---|---|---|---|
| 116 | 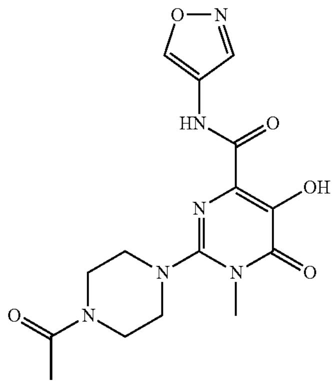 [SMILES: CC(=O)N1CCN(c2nc(C(=O)Nc3cnoc3)c(O)c(=O)n2C)CC1] | 2-(4-acetylpiperazin-1-yl)-5-hydroxy-N-(isoxazol-4-yl)-1-methyl-6-oxo-1,6-dihydropyrimidine-4-carboxamide | ESI-MS m/z = 363.3 [M + H]+. Calculated MW: 362.3 |
| 117 | 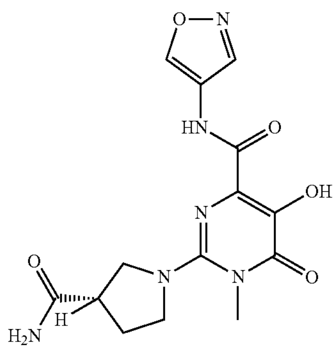 [SMILES: Cn1c(N2CC[C@H](C(N)=O)C2)nc(C(=O)Nc2cnoc2)c(O)c1=O] | (S)-2-(3-carbamoylpyrrolidin-1-yl)-5-hydroxy-N-(isoxazol-4-yl)-1-methyl-6-oxo-1,6-dihydropyrimidine-4-carboxamide | ESI-MS m/z = 349.2 [M + H]+. Calculated MW: 348.3 |
| 118 | 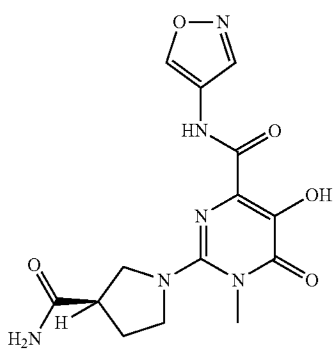 [SMILES: Cn1c(N2CC[C@@H](C(N)=O)C2)nc(C(=O)Nc2cnoc2)c(O)c1=O] | (R)-2-(3-carbamoylpyrrolidin-1-yl)-5-hydroxy-N-(isoxazol-4-yl)-1-methyl-6-oxo-1,6-dihydropyrimidine-4-carboxamide | ESI-MS m/z = 349.2 [M + H]+. Calculated MW: 348.3 |
| 119 | 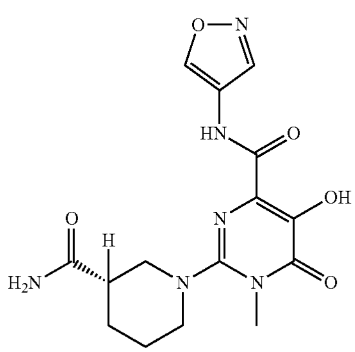 [SMILES: Cn1c(N2CCC[C@H](C(N)=O)C2)nc(C(=O)Nc2cnoc2)c(O)c1=O] | (S)-2-(3-carbamoylpiperidin-1-yl)-5-hydroxy-N-(isoxazol-4-yl)-1-methyl-6-oxo-1,6-dihydropyrimidine-4-carboxamide | ESI-MS m/z = 363.2 [M + H]+. Calculated MW: 362.3 |

TABLE 9-continued

| Example | Structure | Name | LCMS |
|---|---|---|---|
| 120 | 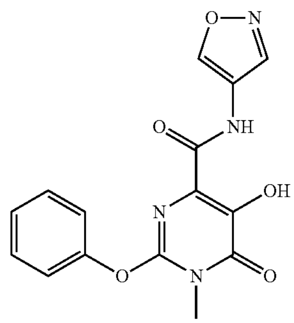 [SMILES: Cn1c(Oc2ccccc2)nc(C(=O)Nc2cnoc2)c(O)c1=O] | 5-hydroxy-N-(isoxazol-4-yl)-1-methyl-6-oxo-2-phenoxy-1,6-dihydropyrimidine-4-carboxamide | ESI-MS m/z = 329.1 [M + H]+. Calculated MW: 328.3 |
| 121 | 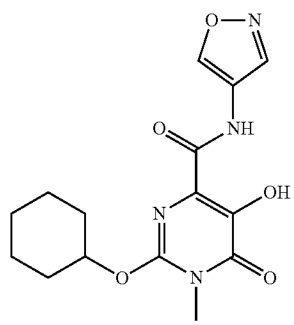 [SMILES: Cn1c(OC2CCCCC2)nc(C(=O)Nc2cnoc2)c(O)c1=O] | 2-(cyclohexyloxy)-5-hydroxy-N-(isoxazol-4-yl)-1-methyl-6-oxo-1,6-dihydropyrimidine-4-carboxamide | ESI-MS m/z = 335.1 [M + H]+. Calculated MW: 334.3 |
| 122 | 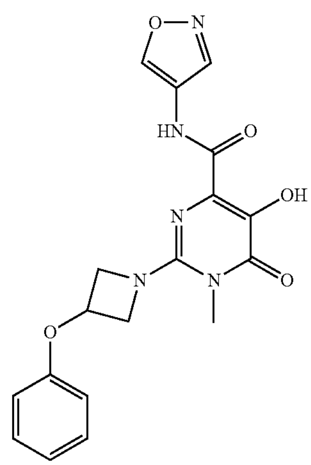 [SMILES: Cn1c(N2CC(Oc3ccccc3)C2)nc(C(=O)Nc2cnoc2)c(O)c1=O] | 5-hydroxy-N-(isoxazol-4-yl)-1-methyl-6-oxo-2-(3-phenoxyazetidin-1-yl)-1,6-dihydropyrimidine-4-carboxamide | ESI-MS m/z = 384.2 [M + H]+. Calculated MW: 383.4 |
| 123 | 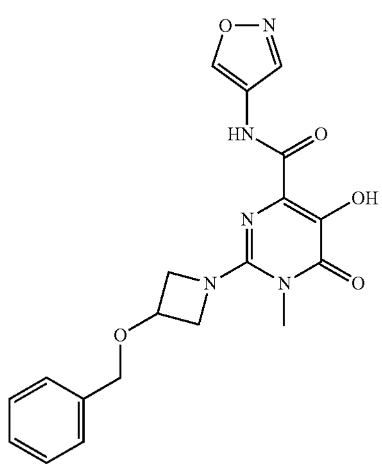 [SMILES: Cn1c(N2CC(OCc3ccccc3)C2)nc(C(=O)Nc2cnoc2)c(O)c1=O] | 2-(3-(benzyloxy)azetidin-1-yl)-5-hydroxy-N-(isoxazol-4-yl)-1-methyl-6-oxo-1,6-dihydropyrimidine-4-carboxamide | ESI-MS m/z = 398.2 [M + H]+. Calculated MW: 397.4 |

TABLE 9-continued

| Example | Structure | Name | LCMS |
|---|---|---|---|
| 124 | 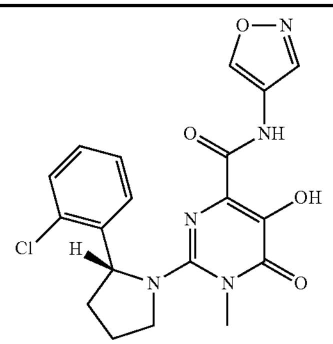 | (R)-2-(2-(2-chlorophenyl)pyrrolidin-1-yl)-5-hydroxy-N-(isoxazol-4-yl)-1-methyl-6-oxo-1,6-dihydropyrimidine-4-carboxamide | ESI-MS m/z = 416.2 [M + H]+. Calculated MW: 415.8 |
| 125 | 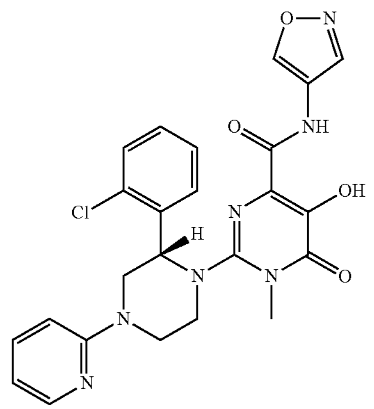 [SMILES: Cn1c(N2CCN(c3ccccn3)C[C@@H]2c2ccccc2Cl)nc(C(=O)Nc2cnoc2)c(O)c1=O] | (S)-2-(2-(2-chlorophenyl)-4-(pyridin-2-yl)piperazin-1-yl)-5-hydroxy-N-(isoxazol-4-yl)-1-methyl-6-oxo-1,6-dihydropyrimidine-4-carboxamide | ESI-MS m/z = 508.3 [M + H]+. Calculated MW: 507.9 |
| 126-127 | Intentionally Omitted | | |
| 128 | 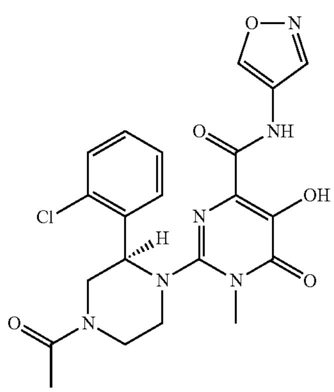 [SMILES: CC(=O)N1CCN(c2nc(C(=O)Nc3cnoc3)c(O)c(=O)n2C)[C@H](c2ccccc2Cl)C1] | (R)-2-(4-acetyl-2-(2-chlorophenyl)piperazin-1-yl)-5-hydroxy-N-(isoxazol-4-yl)-1-methyl-6-oxo-1,6-dihydropyrimidine-4-carboxamide | ESI-MS m/z = 473.3 [M + H]+. Calculated MW: 472.9 |

Biochemical Assays

1. Silencing TREX1 in Tumor Cells

Activation of the cGAS/STING pathway upon sensing of cytosolic DNA and subsequent type I IFN production can occur in both tumor cells and innate immune cells, particularly dendritic cells. To evaluate whether TREX1 keeps in check the production of type I IFN by a well described, cold syngeneic tumor model that undergoes immune-mediated rejection upon activation of type I IFN by STING agonists, TREX1 was knocked down in B16F10 tumor cells using CRISPR (FIG. 1A). Accumulation of cytosolic DNA via DNA transfection of the tumor cells resulted in an about 5-fold increase in IFNβ production by the TREX1 knockout B16F10 cells relative to the parental tumor cells, demonstrating that TREX1 attenuated the activation of the cGAS/STING pathway in B16F10 tumor cells (FIG. 1B).

2. Growth of TREX1-Competent and -Deficient B16F10 Tumor Cells In Vivo

Figure 2:
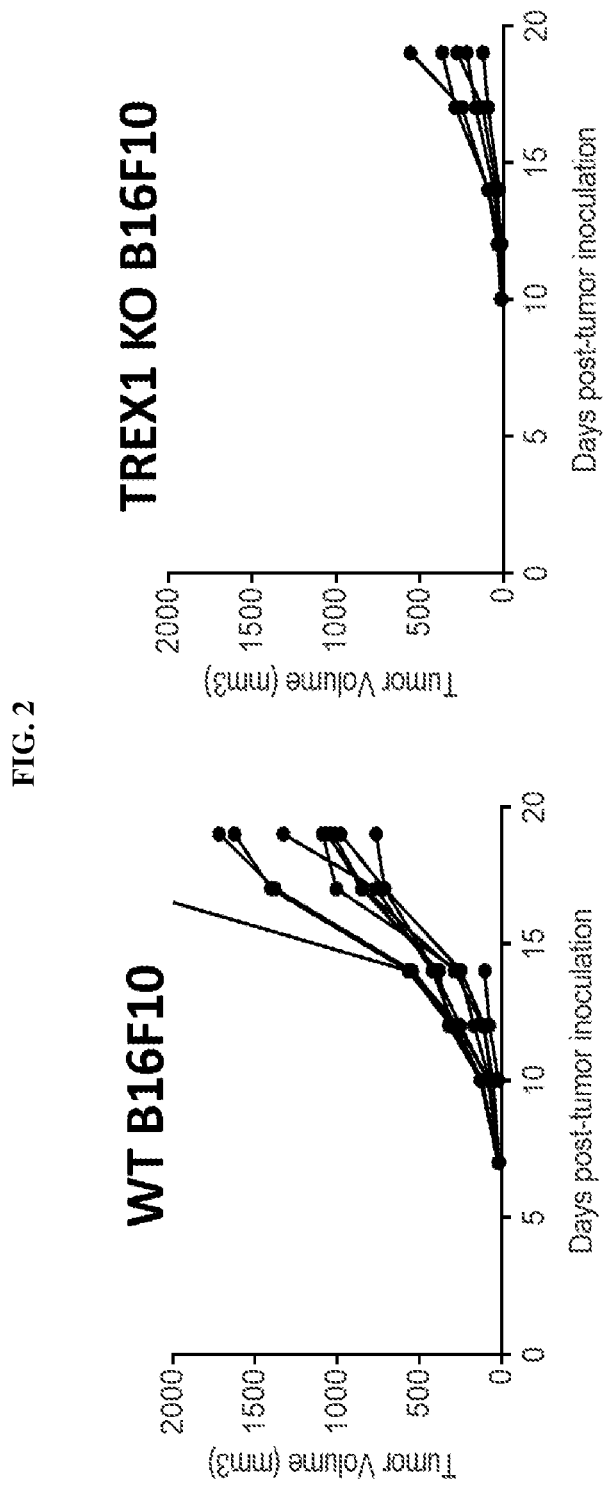
FIG. 2: illustrates that tumors in which TREX had been silenced had smaller volumes compared with parental B16F10 tumors.

The growth of TREX1-competent and -deficient B16F10 tumor cells in vivo was evaluated. C57BL/6J mice were inoculated subcutaneously on the right flank with 300,000 parental or TREX1 knockout B16F10 tumor cells. Body weights were collected two times per week, and tumor measurements, two to three times per week, starting when tumors became measurable and for the remaining duration of the study. Tumors in which TREX1 had been silenced presented with remarkably smaller volumes than the parental B16F10 tumors (FIG. 2).

Figure 3:
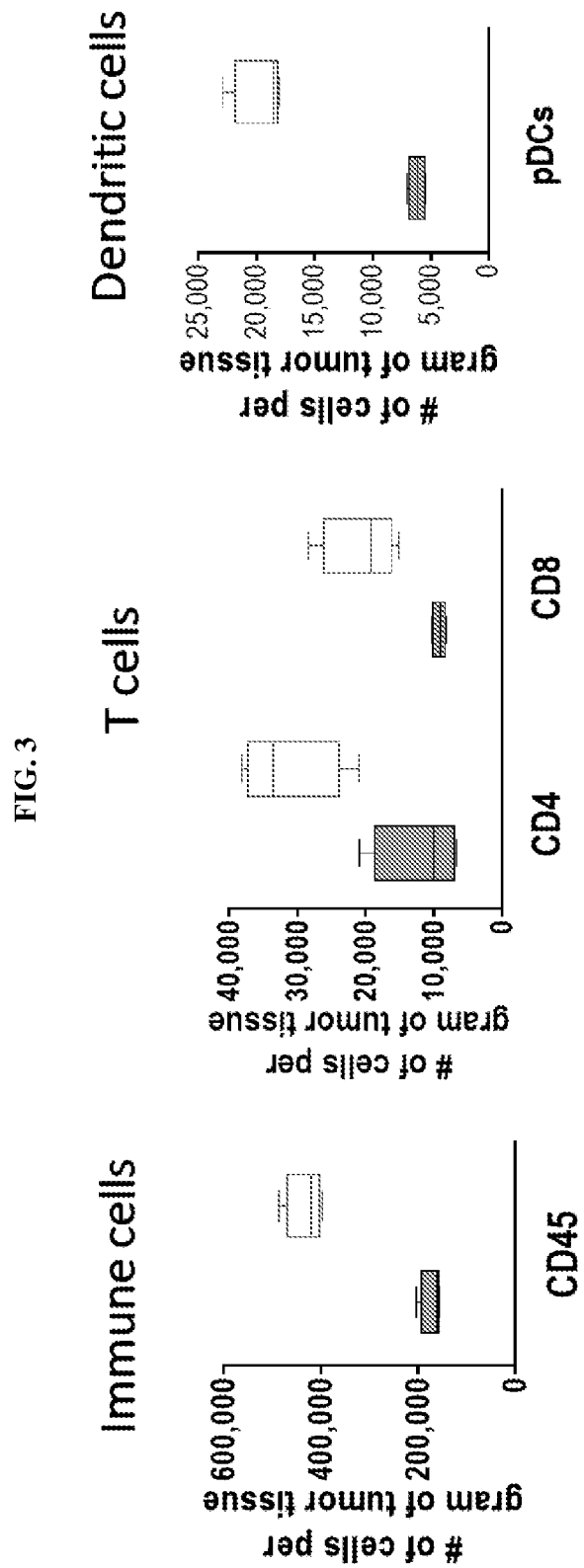
FIG. 3: shows that TREX1 knockout B16F10 tumors exhibited a significant increase in overall immune cells. This reflected an increase in the number of tumor infiltrating CD4 and CD8 T cells as well as in plasmacytoid dendritic cells (pDCs).
Figure 4:
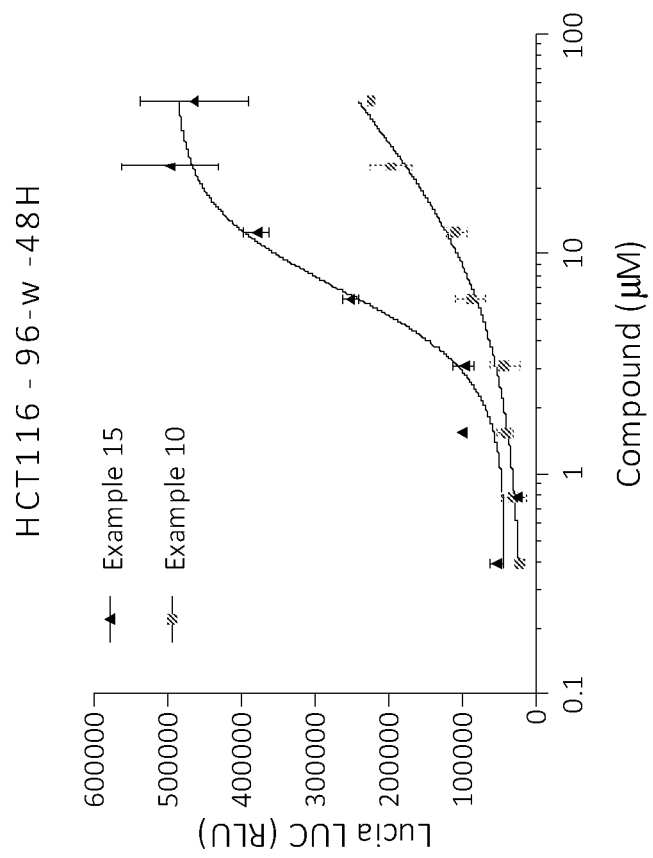
FIG. 4: shows the activity of certain inventive compounds in human HCT116 colorectal carcinoma cell line.

Tumors were harvested on day 19, upon termination of the study, and digested into single cell suspensions to enable flow cytometry quantification of tumor-infiltrating immune populations. TREX1 knockout B16F10 tumors were found to exhibit a significant increase in overall immune cells, which reflected an increase in the number of tumor infiltrating CD4 and CD8 T cells as well as in plasmacytoid dendritic cells (pDCs) (FIG. 3). pDCs are known to play a central role in the induction of antigen-specific anti-tumor immune responses whereas T cells are known to be major effectors of anti-tumor efficacy in mice and humans. The profound change in the immune infiltrate of the tumors deficient in TREX1 thus suggest that the inhibition of the growth of the latter tumors is at least in part immune-mediated.

TREX1 Biochemical Assay

Compound potency was assessed through a fluorescence assay measuring degradation of a custom dsDNA substrate possessing a fluorophore-quencher pair on opposing strands. Degradation of the dsDNA liberates free fluorophore to produce a fluorescent signal. Specifically, 7.5 µL of N-terminally His-Tev tagged full length human TREX1 (expressed in *E. coli* and purified in house) in reaction buffer (50 mM Tris (pH 7.4), 150 mM NaCl, 2 mM DTT, 0.1 mg/mL BSA, 0.01% (v/v) Tween-20 and 100 mM $MgCl_2$) were added to a 384-well Black ProxiPlate Plus (Perkin Elmer) which already contained compound (150 nL) at varying concentrations as a 10 point dose-response in DMSO. To this was added 7.5 µL of dsDNA substrate (Strand A: 5' TEX615/GCT AGG CAG 3'; Strand B: 5' CTG CCT AGC/IAbRQSp (Integrated DNA Technologies)) in reaction buffer. Final concentrations were 150 pM TREX1, 60 nM dsDNA substrate in reaction buffer with 1.0% DMSO (v/v). After 25 minutes at room temperature, reactions were quenched by the addition of 5 µL of stop buffer (same as reaction buffer plus 200 mM EDTA). Final concentrations in the quenched reaction were 112.5 pM TREX1, 45 nM DNA and 50 mM EDTA in a volume of 20 µL. After a 5-minute incubation at room temperature, plates were read in a laser sourced Envision (Perkin-Elmer), measuring fluorescence at 615 nm following excitation w/570 nm light. $IC_{50}$ values were calculated by comparing the measured fluorescence at 615 nm ratio relative to control wells pre-quenched w/stop buffer (100% inhibition) and no inhibitor (0% inhibition) controls as using non-linear least square four parameter fits and either Genedata or GraphPad Prism (GraphPad Software, Inc.).

TREX2 Biochemical Assay

Compound potency was assessed through a fluorescence assay measuring degradation of a custom dsDNA substrate possessing a fluorophore-quencher pair on opposing strands. Degradation of the dsDNA liberates free fluorophore to produce a fluorescent signal. Specifically, 7.5 µL of N-terminally His-Tev tagged human TREX2 (residues M44-A279, expressed in *E. coli* and purified in house) in reaction buffer (50 mM Tris (pH 7.4), 150 mM NaCl, 2 mM DTT, 0.1 mg/mL BSA, 0.01% (v/v) Tween-20 and 100 mM $MgCl_2$) was added to a 384-well Black ProxiPlate Plus (Perkin Elmer) which already contained compound (150 nL) at varying concentrations as a 10 point dose-response in DMSO. To this was added 7.5 µL of dsDNA substrate (Strand A: 5' TEX615/GCT AGG CAG 3'; Strand B: 5' CTG CCT AGC/IAbRQSp (IDT)) in reaction buffer. Final concentrations were 2.5 nM TREX2, 60 nM dsDNA substrate in reaction buffer with 1.0% DMSO (v/v). After 25 minutes at room temperature, reactions were quenched by the addition of 5 µL of stop buffer (same as reaction buffer plus 200 mM EDTA). Final concentrations in the quenched reaction mixture were 1.875 pM TREX2, 45 nM DNA and 50 mM EDTA in a volume of 20 µL. After a 5-minute incubation at room temperature, plates were read in a laser sourced Envision (Perkin-Elmer), measuring fluorescence at 615 nm following excitation w/570 nm light. $IC_{50}$ values were calculated by comparing the measured fluorescence at 615 nm ratio relative to control wells pre-quenched w/stop buffer (100% inhibition) and no inhibitor (0% inhibition) controls as using non-linear least square four parameter fits and either Genedata or GraphPad Prism (GraphPad Software, Inc.).

Results are shown in Table 1. TREX1 $IC_{50}$: A=<0.1 µM; B=0.1 to 1 µM; C=1 to 10 µM; D=>10 µM. TREX2 $IC_{50}$: A=<1 µM, B=1 to 10 µM, C=10 to 100 µM, D=>100 µM.

TABLE 10

| Example | TREX1 $IC_{50}$ | TREX2 $IC_{50}$ |
| --- | --- | --- |
| 1 | A | B |
| 2 | B | C |
| 3 | B | C |
| 4 | B | B |
| 5 | A | B |
| 6 | B | C |
| 7 | B | C |
| 8 | B | C |
| 9 | B | C |
| 10 | A | B |
| 11 | B | C |
| 12 | C | C |
| 13 | B | C |
| 14 | B | B |
| 15 | A | A |
| 16 | B | C |
| 17 | C | C |
| 18 | B | C |
| 19 | C | D |
| 20 | B | C |
| 21 | C | D |
| 22 | C | C |
| 23 | B | B |
| 24 | B | D |
| 25 | B | B |
| 26 | C | C |
| 27 | D | D |
| 28 | B | C |
| 29 | C | C |
| 30 | B | B |
| 31 | B | B |
| 32 | B | B |
| 33 | B | C |
| 34 | B | B |
| 35 | B | B |
| 36 | B | C |
| 37 | B | C |
| 38 | B | C |
| 39 | C | C |
| 40 | B | B |
| 41 | B | C |
| 42 | B | C |
| 43 | A | B |
| 44 | B | C |
| 45 | A | B |
| 46 | B | C |
| 47 | B | B |
| 48 | B | B |
| 49 | B | C |
| 50 | B | C |
| 51 | B | B |
| 52 | B | B |
| 53 | B | B |
| 54 | B | C |

TABLE 10-continued

| Example | TREX1 IC$_{50}$ | TREX2 IC$_{50}$ |
|---|---|---|
| 55 | A | B |
| 56 | B | C |
| 57 | B | C |
| 58 | B | B |
| 59 | B | B |
| 60 | C | C |
| 61 | B | B |
| 62 | B | B |
| 63 | B | B |
| 64 | B | C |
| 65 | B | B |
| 66 | B | C |
| 67 | C | C |
| 70 | A | B |
| 73 | B | C |
| 74 | C | C |
| 75 | D | D |
| 76 | B | C |
| 78 | A | B |
| 79 | A | B |
| 80 | A | B |
| 82 | C | C |
| 83 | C | C |
| 84 | A | B |
| 85 | B | C |
| 86 | B | C |
| 87 | C | C |
| 88 | A | B |
| 91 | B | C |
| 92 | B | C |
| 93 | B | B |
| 94 | B | C |
| 95 | B | C |
| 96 | B | C |
| 97 | A | A |
| 98 | B | C |
| 100 | B | C |
| 101 | B | C |
| 102 | B | C |
| 103 | B | C |
| 104 | C | D |
| 106 | B | C |
| 107 | A | B |
| 108 | A | C |
| 109 | A | C |
| 110 | B | C |
| 111 | B | C |
| 112 | A | B |
| 113 | A | B |
| 116 | B | C |
| 117 | B | C |
| 118 | A | C |
| 119 | B | C |
| 120 | A | B |
| 121 | A | B |
| 122 | B | C |
| 123 | B | C |
| 124 | A | B |
| 125 | A | A |
| 128 | A | A |
| 129 | D | D |
| 130 | B | B |
| 131 | A | A |

HCT116 Cell Assay

HCT116 dual cells (Invivogen, San Diego, CA, USA) are derived from the human HCT116 colorectal carcinoma cell line. Cells have been selected for the stable integration of SEAP and Luciferase reporter genes, which expression is under the control of 5 tandem response elements for NF-KB/AP1 and STAT1/STAT2, respectively. The cell line was used to monitor Type I interferon induction and subsequent signaling by measuring the activity of the Lucia luciferase secreted in the culture medium.

HCT116 cells were plated in 96-well plate(s) at 40,000 cells/well in 100 uL DMEM supplemented with 10% FBS and 25 mM Hepes (pH 7.2-7.5). After overnight settling, cells were treated with TREX1i for 4 h (maximum DMSO fraction was 0.1%) before 1 ug/mL pBR322/BstNI restriction digest (New England Biolabs, Ipswich, MA, USA) was transfected with Lipofectamine LTX (ThermoFisher, Grand Island, NY, USA), according to product manual recommendations. Briefly, Lipofectamine LTX (0.35 uL/well) was diluted in OptiMEM (5 uL/well). pBR322/BstNI (100 ng/well) was diluted in OptiMEM (5 uL/well) before Plus reagent (0.1 uL/100 ng DNA) was added. After 5 min incubation at room temperature, the DNA mixture was mixed dropwise with the diluted Lipofectamine LTX. After an additional 10 min incubation, the transfection mix (10 uL/well) was added to the cells. Cells were maintained at 37 C for 48 h before monitoring the Lucia Luciferase activity from the cell culture medium.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of having the Formula I:

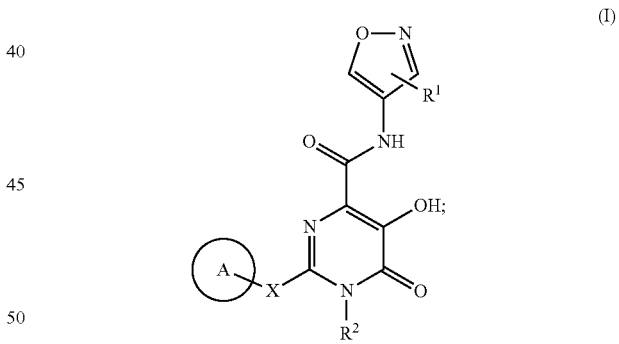

or a pharmaceutically acceptable salt thereof, wherein:
R$^1$ is hydrogen, (C$_1$-C$_4$)alkyl, halo(C$_1$-C$_4$)alkyl, 3- to 4-membered cycloalkyl, —OR$^f$, —SR$^f$, or —NR$^e$R$^f$;
R$^2$ is hydrogen, (C$_1$-C$_4$)alkyl, halo(C$_1$-C$_4$)alkyl, or 3- to 4-membered cycloalkyl;
X is a bond, NR$_3$, O, S, or (C$_1$-C$_4$)alkylene, wherein said (C$_1$-C$_4$)alkylene is optionally substituted with 1 to 2 groups selected from R$^4$;
R$^3$ is hydrogen, (C$_1$-C$_4$)alkyl, —C(O)R$^d$, or —C(S)R$^d$;
R$^4$ is halo, (C$_1$-C$_4$)alkyl, phenyl, —NHC(O)OR$^a$, —NHC(S)OR$^a$, —C(O)R$^b$, —NHC(O)NHR$^g$, —NHC(S)NHR$^g$, —NHS(O) 2NHR$^g$, —C(S)R$^b$, S(O)$_2$R$^c$, S(O)R$^e$, —C(O)OR$^4$, —C(S)OR$^4$, —C(O)NHR$^e$, —C(S)NHR$^e$, —NHC(O)R$^d$, —NHC(S)R$^d$, —OR$^e$, —SR$^e$, —O(C$_1$-C$_4$)alkylOR$^e$, or —NR$^e$R$^f$, wherein said phenyl for $R^4$ is optionally substituted with 1 or 2 groups selected from halo, $(C_1-C_4)$alkyl, halo$(C_1-C_4)$alkyl, $(C_1-C_4)$ alkoxy, and halo$(C_1-C_4)$ alkoxy;

Ring A is phenyl, 5- to 6-membered heteroaryl, 4- to 7-membered heterocyclyl, or 3- to 7-membered cycloalkyl, each of which are optionally and independently substituted with 1 or 2 groups selected from $R^5$;

$R^5$ is $(C_1-C_4)$alkyl, halo$(C_1-C_4)$alkyl, halo$(C_1-C_4)$ alkoxy, halo, phenyl, —NHC(O)OR$^a$, —NHC(S)OR$^a$, —C(O)R$^b$, —NHC(O)NHR$^g$, —NHC(S)NHR$^g$, —NHS(O)$_2$NHR$^g$, —C(S)R$^b$, S(O)$_2$R$^c$, S(O)R$^c$, —C(O)OR$^d$, —C(S)OR$^d$, —C(O)NR$^e$R$^f$, —C(S)NHR$^e$, —NHC(O)R$^d$, —NHC(S)R$^d$, —OR$^e$, —SR$^e$, —O(C$_1$-C$_4$)alkylOR$^e$, —NR$^e$R$^f$, 4- to 6-membered heteroaryl, or 4- to 7-membered heterocyclyl, wherein said phenyl for $R^5$ is optionally substituted with 1 or 2 groups selected from $R^g$, said $(C_1-C_4)$ alkyl for $R^5$ is optionally substituted with 1 or 2 groups selected from OR$^h$, —NR$^j$R$^k$, phenyl, and 5- to 6-membered heteroaryl, said 4- to 7-membered heterocyclyl and 4- to 6-membered heteroaryl are each optionally and independently substituted with 1 or 2 groups selected from R$^m$, and wherein said phenyl and 5- to 6-membered heteroaryl of the optional substituents listed for $(C_1-C_4)$alkyl in $R^5$ are each optionally and independently substituted with 1 or 2 groups selected from R$^g$;

R$^g$, R$^h$, R$^j$, R$^k$, and R$^m$ are each independently hydrogen, halo, $(C_1-C_4)$alkyl, halo$(C_1-C_4)$alkyl, $(C_1-C_4)$ alkoxy, halo$(C_1-C_4)$ alkoxy, phenyl, —$(C_1-C_4)$alkylphenyl, 3- to 4-membered cycloalkyl, 4- to 6-membered heteroaryl, or 4- to 7-membered heterocyclyl, and wherein said 4- to 7-membered heterocyclyl for R$^g$, R$^h$, R$^j$ and R$^k$ is further optionally substituted with =O, R$^a$, R$^b$, R$^c$, R$^d$, R$^e$ and R$^f$ are each independently hydrogen, halo, $(C_1-C_4)$alkyl, halo$(C_1-C_4)$alkyl, $(C_1-C_4)$ alkoxy, halo$(C_1-C_4)$ alkoxy, phenyl, 3- to 4-membered cycloalkyl, 4- to 6-membered heteroaryl, or 4- to 7-membered heterocyclyl, wherein i) said $(C_1-C_4)$alkyl for R$^a$, R$^b$, R$^c$, R$^d$, R$^e$ and R$^g$ is optionally substituted with 1 or 2 groups selected from phenyl, —OR$^h$, —NR$^j$R$^k$; ii) said phenyl, 4- to 6-membered heteroaryl, and 4- to 7-membered heterocyclyl for R$^a$, R$^b$, R$^c$, R$^d$, R$^e$, and R$^f$ are each optionally and independently substituted with 1 or 2 groups selected from R$^g$, and iii) said 4- to 7-membered heterocyclyl for R$^a$, R$^b$, R$^c$, R$^d$, R$^e$, and R$^f$ is further optionally substituted with =O.

2. The compound of claim 1, wherein the compound is of the Formula II:

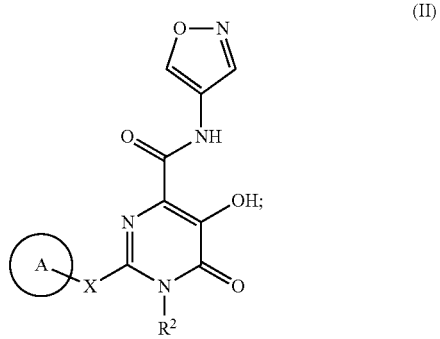

or a pharmaceutically acceptable salt thereof.

3. The compound of claim 1, wherein $R^2$ is $(C_1-C_4)$alkyl.

4. The compound of claim 1, wherein the compound is of the Formula III:

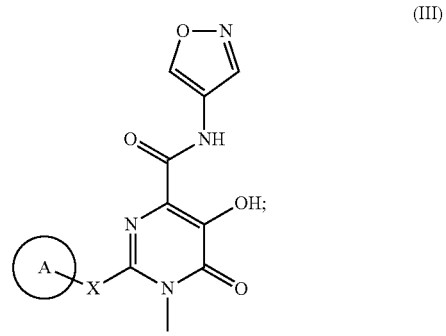

or a pharmaceutically acceptable salt thereof.

5. The compound of claim 1, wherein ring A is phenyl, pyridyl, pyrazolyl, cyclopropyl, cyclobutyl, azetidinyl, or piperidinyl, each of which being optionally and independently substituted with one or two $R^5$.

6. The compound of claim 1, wherein ring A is triazolyl, pyrrolidinyl, diazepanyl, or piperazinyl, each of which being optionally and independently substituted with one or two $R^5$.

7. The compound of claim 1, wherein $R^5$ is $(C_1-C_4)$alkyl, halo$(C_1-C_4)$alkyl, halo$(C_1-C_4)$ alkoxy, halo, phenyl, —NHC(O)OR$^a$, —C(O)R$^b$, S(O)$_2$R$^c$, S(O)R$^e$, —C(O)OR$^d$, —C(O)NR$^e$R$^f$, —NHC(O)R$^d$, —OR$^e$, —O(C$_1$-C$_4$)alkylOR$^e$, —NR$^e$R$^f$, 4- to 6-membered heteroaryl, or 4- to 7-membered heterocyclyl, wherein said phenyl for $R^5$ is optionally substituted with 1 or 2 groups selected from R$^g$, said $(C_1-C_4)$ alkyl for $R^5$ is optionally substituted with 1 or 2 groups selected from —OR$^h$, —NR$^j$R$^k$, phenyl, and 5- to 6-membered heteroaryl, said 4- to 6-membered heteroaryl and 4- to 7-membered heterocyclyl are each optionally and independently substituted with 1 or 2 groups selected from R$^m$, and wherein said phenyl and 5- to 6-membered heteroaryl of the optional substituents listed for $(C_1-C_4)$alkyl in $R^5$ are each optionally and independently substituted with 1 or 2 groups selected from R$^g$;

R$^a$ is $(C_1-C_4)$alkyl optionally substituted with phenyl;

R$^b$ is $(C_1-C_4)$alkyl, phenyl, 5- to 6-membered heteroaryl or 4- to 7-membered heterocyclyl, wherein said $(C_1-C_4)$alkyl is optionally substituted with 1 or 2 groups selected from phenyl, OR$^h$, and —NR$^j$R$^k$, wherein said phenyl, 5- to 6-membered heteroaryl, and 4- to 7-membered heterocyclyl are each optionally and independently substituted with 1 or 2 groups selected from R$^g$, and wherein said 4- to 7-membered heterocyclyl is further optionally substituted with =O;

each R$^c$ is independently phenyl or $(C_1-C_4)$alkyl;

each R$^d$ is hydrogen or $(C_1-C_4)$alkyl;

each R$^e$ is independently hydrogen or $(C_1-C_4)$alkyl optionally substituted with OR";

each R$^f$ is independently hydrogen, $(C_1-C_4)$alkyl, phenyl 3- to 4-membered cycloalkyl, 4- to 6-membered heteroaryl, or 5- to 6-membered heterocyclyl, wherein said phenyl, 3- to 4-membered cycloalkyl, 4- to 6-membered heteroaryl, and 5- to 6-membered heterocyclyl are each optionally and independently substituted with R$^g$;

each R$^g$ is independently $(C_1-C_4)$alkyl, halo$(C_1-C_4)$alkyl, $(C_1-C_4)$ alkoxy, halo$(C_1-C_4)$ alkoxy, or halo;

each $R^h$ is hydrogen, $(C_1-C_4)$alkyl, or —$(C_1-C_4)$alkylphenyl;

each $R^j$ is independently hydrogen or $(C_1-C_4)$alkyl;

each $R^k$ is independently hydrogen, $(C_1-C_4)$alkyl, or 3- to 4-membered cycloalkyl; and each $R^m$ is $(C_1-C_4)$alkyl.

8. The compound of claim 1, wherein $R^5$ is $(C_1-C_4)$alkyl, halo$(C_1-C_4)$alkyl, halo, phenyl, —NHC(O)OR$^a$, —C(O)R$^b$, S(O)$_2$R$^c$, —C(O)OR$^4$, —C(O)NR$^e$R$^f$, —NHC(O)R$^d$, —O($C_1-C_4$)alkylOR$^e$, —NR$^e$R$^f$, 4- to 6-membered heteroaryl, or 5- to 6-membered heterocyclyl, wherein said $(C_1-C_4)$alkyl for $R^5$ is optionally substituted with —OR$^h$, phenyl, or 5- to 6-membered heteroaryl, said 4- to 6-membered heteroaryl and 5- to 6-membered heterocyclyl are each optionally and independently substituted with 1 or 2 groups selected from R$^m$, and wherein said phenyl and 5- to 6-membered heteroaryl of the optional substituents listed for $(C_1-C_4)$alkyl in $R^5$ are each optionally and independently substituted with 1 or 2 groups selected from R$^g$.

9. The compound of claim 1, wherein $R^5$ is $(C_1-C_4)$alkyl, halo$(C_1-C_4)$alkyl, halo, phenyl, —NHC(O)OR$^a$, —C(O)R$^b$, S(O)$_2$R$^c$, —C(O)OR$^4$, —C(O)NR$^e$R$^f$, —NHC(O)R$^d$, or —O($C_1-C_4$)alkylOR$^e$, —NR$^e$R$^f$, morpholinyl, piperazinyl, or pyrazolyl, wherein said morpholinyl, piperazinyl, and pyrazolyl are each optionally substituted with 1 or 2 groups selected from R$^m$, said $(C_1-C_4)$alkyl for $R^5$ is optionally substituted with —OR$^h$, phenyl, pyrazolyl, pyrimidinyl, or pyridinyl, and wherein said phenyl, pyrazolyl, pyrimidinyl, and pyridinyl of the optional substituents listed for $(C_1-C_4)$alkyl in $R^5$ are each optionally and independently substituted with 1 or 2 groups selected from R$^g$.

10. The compound of claim 1, wherein each $R^f$ is independently hydrogen, $(C_1-C_4)$alkyl, phenyl pyrazolyl, pyridinyl, tetrahydropyranyl, piperidinyl, wherein said phenyl pyrazolyl, pyridinyl, tetrahydropyranyl, and piperidinyl are each optionally and independently substituted with $(C_1-C_4)$alkyl.

11. The compound of claim 1, wherein each R& is independently $(C_1-C_4)$alkyl, $(C_1-C_4)$ alkoxy, or halo.

12. The compound of claim 1, wherein $R^b$ is $(C_1-C_4)$alkyl, phenyl, 5- to 6-membered heteroaryl or 4- to 7-membered heterocyclyl, wherein said phenyl and 5- to 6-membered heteroaryl for $R^b$ are each optionally and independently substituted with 1 or 2 groups selected from halo and $(C_1-C_4)$ alkoxy, wherein said 4- to 7-membered heterocyclyl for $R^b$ is optionally substituted with =O, and wherein said $(C_1-C_4)$alkyl for $R^b$ is optionally substituted with 1 or 2 groups selected from phenyl, —OR$^h$, and —NR$^j$R$^k$.

13. The compound of claim 1, wherein each $R^k$ is independently hydrogen or $(C_1-C_4)$alkyl.

14. The compound of claim 1, wherein $R^b$ is $(C_1-C_4)$alkyl, phenyl, pyridinyl, pyrazolyl, pyrimidinyl, or piperidinyl, wherein said phenyl, pyridinyl, pyrazolyl, and pyrimidinyl for $R^b$ are each optionally and independently substituted with 1 or 2 groups selected from halo and $(C_1-C_4)$ alkoxy, wherein said $(C_1-C_4)$alkyl for $R^b$ is optionally substituted with 1 or 2 groups selected from phenyl, OH, and NMe$_2$, and wherein said piperidinyl for $R^b$ is optionally substituted with =O.

15. The compound of claim 1, wherein $R^3$ is hydrogen.

16. The compound of claim 1, wherein X is an unsubstituted $(C_1-C_4)$alkylene.

17. The compound of claim 1, wherein $R^4$ is phenyl or —NHC(O)OR$^a$.

18. The compound of claim 1, wherein X is a bond or CH$_2$.

19. A pharmaceutical composition comprising the compound of claim 1, or a pharmaceutically acceptable salt thereof; and a pharmaceutically acceptable carrier.

* * * * *

UNITED STATES PATENT AND TRADEMARK OFFICE
CERTIFICATE OF CORRECTION

PATENT NO. : 12,172,990 B2
APPLICATION NO. : 17/311526
DATED : December 24, 2024
INVENTOR(S) : Anna Gardberg et al.

Page 1 of 1

It is certified that error appears in the above-identified patent and that said Letters Patent is hereby corrected as shown below:

In the Claims

Column 116, Claim 1: Line 35, delete the text "having the"; Line 58, $NR_3$ should read "$NR^3$"; Line 64, -NHS(O) $2NHR^g$ should read "-$NHS(O)_2NHR^g$"; and Line 65, $S(O)R^e$ should read "$S(O)R^c$", $C(O)OR^4$ should read "$C(O)OR^d$", and $C(S)OR^4$ should read "$C(S)OR^d$".

Column 117, Claim 1: Line 14, $C(O)OR^4$ should read "$C(O)OR^d$" and $C(S)OR^4$ should read "$C(S)OR^d$"; Line 15, $NHC(O)R^4$ should read "$NHC(O)R^d$"; and Line 42, $R^g$ should read "$R^f$".

Column 118, Claim 7: Line 30, $S(O)R^e$ should read "$S(O)R^c$"; Line 55, $R^e$ should read "$R^c$"; and Line 58, OR" should read "$OR^h$".

Column 119, Claim 8: Line 9, $C(O)OR^4$ should read "$C(O)OR^d$"; and Claim 9: Line 23, $C(O)OR^4$ should read "$C(O)OR^d$".

Column 120, Claim 11: Line 4, R& should read "$R^g$"

Signed and Sealed this
Thirtieth Day of September, 2025

John A. Squires
*Director of the United States Patent and Trademark Office*